US012545935B1

(12) United States Patent
Nagata et al.

(10) Patent No.: US 12,545,935 B1
(45) Date of Patent: Feb. 10, 2026

(54) MODIFIED INDOLE-3-ACETIC ACID-AMIDO SYNTHETASE GH3.6 ENZYME HAVING N-ACYLATION ACTIVITY

(71) Applicant: AJINOMOTO CO., INC., Tokyo (JP)

(72) Inventors: Hidemi Nagata, Tokyo (JP); Uno Tagami, Tokyo (JP); Hiroyuki Nozaki, Tokyo (JP); Keiko Koenuma, Tokyo (JP); Daria Streltsova, Moscow (RU); Anna Khruscheva, Moscow (RU); Joanna Katashkina, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 747 days.

(21) Appl. No.: 17/713,841

(22) Filed: Apr. 5, 2022

Related U.S. Application Data

(63) Continuation of application No. PCT/JP2020/038340, filed on Oct. 9, 2020.

(30) Foreign Application Priority Data

Oct. 10, 2019 (RU) ................................ 2019131887

(51) Int. Cl.
*C12P 13/02* (2006.01)
*C12N 9/00* (2006.01)
*C12N 9/16* (2006.01)

(52) U.S. Cl.
CPC ................ *C12P 13/02* (2013.01); *C12N 9/16* (2013.01); *C12N 9/93* (2013.01); *C12Y 301/02014* (2013.01); *C12Y 602/01003* (2013.01); *C12Y 603/02* (2013.01)

(58) Field of Classification Search
None
See application file for complete search history.

(56) References Cited

U.S. PATENT DOCUMENTS

| | | | |
|---|---|---|---|
| 2018/0127791 A1 | 5/2018 | Schaffer et al. | |
| 2021/0071214 A1 | 3/2021 | Nagata et al. | |

FOREIGN PATENT DOCUMENTS

| | | | |
|---|---|---|---|
| JP | 06-022776 | A | 2/1994 |
| JP | 2018-085969 | A | 6/2018 |
| RU | 2019131887 | * | 10/2019 |
| WO | WO2008/131002 | A2 | 10/2008 |
| WO | WO2014/100525 | A2 | 6/2014 |
| WO | WO2015/028423 | A1 | 3/2015 |
| WO | WO2019/198367 | A1 | 10/2019 |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26: Unit26.7. (Year: 2011).*
Yoshikuni et al. Curr Opin Chem Biol. Apr. 2007; 11(2):233-9. (Year: 2007).*
Accession AEI14905, Jun. 15, 2007 (Year: 2007).*
Wada, E., et al., "Enzymatic Synthesis of N-Acyl-L-Amino Acids in a Glycerol-Water System Using Acylase I from Pig Kidney," JAOCS 2002;79(1):41-46.
Koreishi, M., et al., "A Novel Acylase from Streptomyces mobaraensis that Efficiently Catalyzes Hydrolysis/Synthesis of Capsaicins as Well as N-Acyl-L-amino acids and N-Acyl-peptides," J. Agric. Food Chem. 2006;54:72-78.
Voelker, T. A., et al., "Alteration of the Specificity and Regulation of Fatty Acid Synthesis of *Escherichia coli* by Expression of a Plant Medium-Chain Acyl-Acyl Carrier Protein Thioesterase," J. Bacteriol. 1994;176 (23):7320-7327.
International Search Report for PCT Patent App. No. PCT/JP2020/038340 (Dec. 15, 2020).
Westfall., C. S., et al., "Modulating plant hormones by enzyme action: the GH3 family of acyl acid amido synthetases," Plant Signal Behav. 2010, 5:12, pp. 1607-1612.
Staswick, P. E., et al., "Characterization of an Arabidopsis Enzyme Family That Conjugates Amino Acids to Indole-3-Acetic Acid," Plant Cell 2005;17:616-627.
Partial Supplementary European Search Report for European Patent App. No. 20873390.7 (Mar. 12, 2024).
Chen, Q., et al., "A liquid chromatography-tandem mass spectrometry-based assay for indole-3-acetic acid-amido synthetase," Analytical Biochem. 2009;390:149-154.
Database GenePept [Online]. Oct. 13, 2016, "Indole-3-acetic acid-amido synthetase GH3.6 [Brassica rapa]", XP093108052, retrieved from NCBI accession No. XP_009127083.1 on Dec. 1, 2023, Database accession No. XP_/009127083, 2 pp.
Wada, E., et al., "Enzymatic Synthesis of N-Acyl-L-Amino Acids in a Glycerol-Water System Using Acylase I from Pig Kidney," J. Am. Oil Chem. Soc. 2002;79(1):41-46.
Database Geneseq [Online], Nov. 28, 2019, "A. thaliana indole-3-acetic acid-amido synthetase GH3.5 (atGH3-5), SEQ 4.", XP093108066, retrieved from EBI accession No. GSP:BGW08876 on Dec. 1, 2023, Database accession No. BGW08876, 1 pg.

(Continued)

*Primary Examiner* — Christian L Fronda
(74) *Attorney, Agent, or Firm* — Cermak & McGowan LLP; Shelly Guest Cermak

(57) ABSTRACT

The present invention provides an enzyme useful for establishing an excellent N-acyl-amino group-containing compound production system, and the like. More specifically, the present invention provides a modified enzyme comprising: (A) a modified amino acid sequence consisting of an amino acid sequence comprising mutations of one or more certain amino acid residues in an amino acid sequence of a wild type enzyme having an N-acylation activity; (B) an amino acid sequence comprising substitution, deletion, insertion, or addition of one or several additional amino acid residues in the modified amino acid sequence; or (C) an amino acid sequence comprising additional mutations of one or more amino acid residues in the modified amino acid sequence and having 90% or more identity to the modified amino acid sequence, having an N-acylation activity, and having an improved N-acylation activity to L-glutamic acid or L-aspartic acid or an improved substrate specificity to L-glutamic acid as compared with the wild type enzyme, and the like.

27 Claims, 3 Drawing Sheets

Specification includes a Sequence Listing.

(56) References Cited

OTHER PUBLICATIONS

Extended European Search Report for European Patent App. No. 20873390.7 (Jul. 22, 2024).
Database Geneseq [Online], "*Arabidopsis lyrata* GH3 superfamily protein, A1GH3-4 SEQ ID: 70," Jun. 18, 2015, XP93183469, retrieved from EBI accession No. GSP:BBI80581 on Jul. 22, 2024, Database accession No. BBI80581, 2 pp.
"Sorghum bicolor GH3 superfamily protein, SbEES16535 SEQ ID: 42," Jun. 18, 2015, XP93183475, retrieved from EBI accession No. GSP:BBI80554 on Jul. 22, 2024, Database accession No. BBI80554, 2 pp.
"Auxin-responsive GH3 family protein [*Arabidopsis thaliana*]", NP_200262.1, Tabata, S., GenBank, Feb. 14, 2019; retrieved from the internet on May 15, 2025.
Office Action from Chinese Patent App. No. 202080070926.1 (May 17, 2025) with English language translation thereof.

* cited by examiner

MODIFIED INDOLE-3-ACETIC ACID-AMIDO SYNTHETASE GH3.6 ENZYME HAVING N-ACYLATION ACTIVITY

This application is a Continuation of, and claims priority under 35 U.S.C. § 120 to, International Application No. PCT/JP2020/038340, filed Oct. 9, 2020, and claims priority therethrough under 35 U.S.C. § 119 to Russian Patent Application No. 2019131887, filed Oct. 10, 2019, the entireties of which are incorporated by reference herein. Also, the Sequence Listing filed electronically herewith is hereby incorporated by reference (File name: 2022-04-05T_US-638_Seq_List; File size: 48 KB; Date recorded: Apr. 5, 2022).

TECHNICAL FIELD

The present invention relates to a modified enzyme having an N-acylation activity or the like.

BACKGROUND ART

N-acyl-amino group-containing compounds, such as Nα-acylamino acids, are typically used cosmetics, acting as a surfactant or the like. Chemical synthesis of N-acyl-amino group-containing compounds by, for example, the Schotten-Baumann reaction, is problematic due to the environmental burden caused by a by-product of this synthesis reaction. Therefore, enzymatic synthesis of the N-acyl-amino group-containing compound is required. Several documents of prior art related to the enzymatic synthesis of the N-acyl-amino group-containing compound have been reported.

Patent Literature 1 reports Nα-acylamino acid fermentation from a saccharide using a *Bacillus subtilis* surfactin biosynthetic enzyme. However, since the production amount of Nα-acylglutamic acid is as small as 116.8 mg/L, this fermentation is not suitable for production on an industrial scale.

Patent Literature 2 reports a method for synthesizing Nα-acylglycine from an amino acid and a fatty acid using a human-derived amino acid N-acyltransferase and an *E. coli*-derived acyl-CoA synthase. However, this method cannot directly bond the amino acid to the fatty acid and requires a two-step enzymatic reaction, and therefore is problemative because of the use of a control is complicated as compared with a reaction using a single enzyme.

Non-Patent Literature 1 reports a method for synthesizing an Nα-acylamino acid from an amino acid and a fatty acid in a solution containing glycerol using a porcine kidney-derived acylase. This method takes advantage of the fact that a hydrolysis reaction of an Nα-acylamino acid by acylase is greatly inhibited in a solution containing glycerol. However, this method is less efficient in industrial production in view of the requirement for use of a large amount of glycerol and a low yield in Nα-acylamino acid synthesis in an aqueous solvent containing no glycerol.

Non-Patent Literature 2 reports a method for synthesizing an Nα-acylamino acid from an amino acid and a fatty acid in a solution containing glycerol using a *Streptomyces mobaraensis*-derived acylase. However, since Nα-acylamino acid synthesis in an aqueous solvent containing no glycerol has not been previously reported, the efficiency of this method for industrial production has not been previously described.

PRIOR ART REFERENCES

Patent Literature

Patent Literature 1: WO 2008/131002 A
Patent Literature 2: WO 2015/028423 A

Non-Patent Literature

Non-Patent Literature 1: Wada et al., Journal of the American Oil Chemists' Society, 2002, 79 (1), pp 41-46

Non-Patent Literature 2: Koreishi et al., Journal of Agricultural and Food Chemistry, 2006, 54 (1), pp 72-78

SUMMARY

An aspect of the present invention is to provide an enzyme useful for establishing an excellent N-acyl-amino group-containing compound production system, a method for producing an N-acyl-amino group-containing compounds, and the like.

Described herein is production of a modified enzyme having an excellent ability to produce an N-acyl-amino group-containing compound by mutating an amino acid residue(s) of indole-3-acetic acid-amido synthetase GH3.6 (AtGH3-6) derived from *Arabidopsis thaliana*, and production of an N-acyl-amino group-containing compound.

It is an aspect of the present invention to provide a modified enzyme comprising an amino acid sequence selected from the group consisting of: (A) an amino acid sequence comprising a mutation of an amino acid residue selected from the group consisting of N101, R117, T122, I123, Y134, L137, V140, S161, V174, Q200, V231, V311, C335, T336, M337, A339, S340, Y344, R350, G379, K388, L390, S455, E483, Q533, C576, and combinations thereof in the amino acid sequence of SEQ ID NO: 1; (B) the amino acid sequence of (A), but comprising substitution, deletion, insertion, or addition of one or several additional amino acid residues; and (C) the amino acid sequence of (A), but comprising additional mutations of one or more amino acid residues and having 90% or more identity to the amino acid sequence of (A), and wherein said modified enzyme has an N-acylation activity comprising: (i) an N-acylation activity to L-glutamic acid and/or L-aspartic acid; and/or (ii) a substrate specificity to L-glutamic acid; wherein the N-acylation activity is improved over a non-modified enzyme consisting of the amino acid sequence of SEQ ID NO: 1.

It is a further aspect of the present invention to provide the modified enzyme as described above, wherein the mutation is selected from the group consisting of N101S, R117P, T122S, I123T, Y134F, Y134V, L137I, V140I, S161P, V174A, Q200E, V231A, V311A, C335S, T336S, M337G, M337A, A339G, S340A, Y344A, Y344G, Y344I, Y344V, R350T, G379D, K388N, L390P, S455T, E483D, Q533R, C576A, and combinations thereof.

It is a further aspect of the present invention to provide the modified enzyme as described above, wherein the N-acylation activity is to L-glutamic acid or L-aspartic acid.

It is a further aspect of the present invention to provide a polynucleotide encoding the modified enzyme as described above.

It is a further aspect of the present invention to provide an expression vector comprising the polynucleotide as described above.

It is a further aspect of the present invention to provide a host cell comprising an expression unit of a polynucleotide encoding the modified enzyme as described above.

It is a further aspect of the present invention to provide the host cell described above, wherein the host cell is a microorganism comprising at least one of the following genetic modifications: (1) enhancement of ability to supply a fatty acid; (2) enhancement of ability to supply an amino acid; (3) enhancement of ability to supply ATP; and (4) deficiency or attenuation of an N-acylamino acid degrading enzyme.

It is a further aspect of the present invention to provide the host cell as described above, wherein the enhancement of ability to supply a fatty acid is (a) deficiency or attenuation of acyl CoA synthetase; and/or (b) enhancement of acyl-ACP thioesterase.

It is a further aspect of the present invention to provide the host cell as described above, wherein the host cell is a bacterium belonging to the family Enterobacteriaceae.

It is a further aspect of the present invention to provide the host cell as described above, wherein the bacterium belonging to the family Enterobacteriaceae is a bacterium belonging to the genus *Escherichia* or a bacterium belonging to the genus *Pantoea*.

It is a further aspect of the present invention to provide the host cell as described above, wherein the bacterium belonging to the genus *Escherichia* is *Escherichia coli*, and the bacterium belonging to the genus *Pantoea* is *Pantoea ananatis*.

It is a further aspect of the present invention to provide a method for producing an N-acyl-amino group-containing compound or a salt thereof, the method comprising: reacting an amino group-containing compound and a carboxyl group-containing compound in the presence of a modified enzyme selected from the group consisting of: (A) an amino acid sequence comprising a mutation of an amino acid residue selected from the group consisting of N101, R117, T122, 1123, Y134, L137, V140, S161, V174, Q200, V231, V311, C335, T336, M337, A339, S340, Y344, R350, G379, K388, L390, S455, E483, Q533, C576, and combinations thereof in the amino acid sequence of SEQ ID NO: 1; (B) the amino acid sequence of (A), but comprising substitution, deletion, insertion, or addition of one or several additional amino acid residues; and (C) the amino acid sequence of (A), but comprising additional mutations of one or more amino acid residues and having 90% or more identity to the amino acid sequence of (A), wherein said modified enzyme has an N-acylation activity comprising: (i) an N-acylation activity to L-glutamic acid and/or L-aspartic acid; and/or (ii) a substrate specificity to L-glutamic acid; and wherein the N-acylation activity is improved over a non-modified enzyme consisting of the amino acid sequence of SEQ ID NO: 1.

It is a further aspect of the present invention to provide a method as described above, wherein the modified enzyme is a purified enzyme.

It is a further aspect of the present invention to provide a method as described above, wherein said reacting is performed using a transformed microorganism that produces the modified enzyme, or a treated product thereof.

It is a further aspect of the present invention to provide a method as described above, wherein the transformed microorganism comprises at least one genetic modification selected from: (1) enhancement of ability to supply a fatty acid; (2) enhancement of ability to supply an amino acid; (3) enhancement of ability to supply ATP; and (4) deficiency or attenuation of an N-acylamino acid degrading enzyme.

It is a further aspect of the present invention to provide a method as described above, wherein the amino group-containing compound and the carboxyl group-containing compound are produced in the transformed microorganism by culturing the transformed microorganism in the presence of a carbon source.

It is a further aspect of the present invention to provide a method for producing an N-acyl-amino group-containing compound in which an amino group-containing compound and a carboxyl group-containing compound are bonded to each other by an amide bond, or a salt thereof, the method comprising culturing, in the presence of a carbon source, a microorganism which comprises at least one of the following genetic modifications: (1) enhancement of ability to supply a fatty acid; (2) enhancement of ability to supply an amino acid; (3) enhancement of ability to supply ATP; and (4) deficiency or attenuation of an N-acylamino acid degrading enzyme, and wherein said microorganism comprises expression unita polynucleotide encoding an enzyme having an ability to bond a carboxyl group and an amino group to each other in an ATP-dependent manner to form an amide bond.

It is a further aspect of the present invention to provide a method as described above, wherein the enzyme is a GH3 protein or a PaaK protein.

It is a further aspect of the present invention to provide a method as described above, wherein the GH3 protein is (I) a modified enzyme comprising an amino acid sequence selected from the group consisting of: (A) an amino acid sequence comprising a mutation of an amino acid residue selected from the group consisting of N101, R117, T122, 1123, Y134, L137, V140, S161, V174, Q200, V231, V311, C335, T336, M337, A339, S340, Y344, R350, G379, K388, L390, S455, E483, Q533, C576, and combinations thereof in the amino acid sequence of SEQ ID NO: 1; (B) the amino acid sequence of (A), but comprising substitution, deletion, insertion, or addition of one or several additional amino acid residues; and (C) the amino acid sequence of (A), but comprising additional mutations of one or more amino acid residues and having 90% or more identity to the amino acid sequence of (A), and wherein said modified enzyme has an N-acylation activity comprising: (i) an N-acylation activity to L-glutamic acid and/or L-aspartic acid; and/or (ii) a substrate specificity to L-glutamic acid; wherein the N-acylation activity is improved over a non-modified enzyme consisting of the amino acid sequence of SEQ ID NO: 1, or (II) an enzyme selected from the group consisting of: (D) a protein comprising the amino acid sequence of SEQ ID NO: 1; (E) a protein comprising an amino acid sequence comprising substitution, deletion, insertion, or addition of one or several amino acids in the amino acid sequence of SEQ ID NO: 1 and having an N-acylation activity; and (F) a protein comprising an amino acid sequence having 90% or more identity to the amino acid sequence of SEQ ID NO: 1 and having an N-acylation activity.

It is a further aspect of the present invention to provide a method as described above, wherein the genetic modification of the enhancement of ability to supply a fatty acid is: (a) deficiency or attenuation of acyl CoA synthetase; and/or (b) enhancement of acyl-ACP thioesterase.

It is a further aspect of the present invention to provide a method as described above, wherein the acyl-ACP thioesterase has a thioesterase activity to lauroyl-ACP.

It is a further aspect of the present invention to provide a method as described above, wherein the acyl-ACP thioesterase is selected from the group consisting of: (i) a protein comprising (i-1) the amino acid sequence of SEQ ID NO: 3, or (i-2) the amino acid sequence consisting of amino acid residues at positions 84 to 382 in the amino acid sequence of SEQ ID NO: 3; (ii) a protein comprising an amino acid sequence comprising substitution, deletion, insertion, or addition of one or several amino acids in (ii-1) the amino acid sequence of SEQ ID NO: 3 or (ii-2) the amino acid sequence consisting of amino acid residues at positions 84 to 382 in the amino acid sequence of SEQ ID NO: 3, and having an acyl-ACP thioesterase activity; and (iii) a protein comprising an amino acid sequence having 90% or more identity to (iii-1) the amino acid sequence of SEQ ID NO: 3 or (iii-2) the amino acid sequence consisting of amino acid residues at positions 84 to 382 in the amino acid sequence of SEQ ID NO: 3, and having acyl-ACP thioesterase activity.

It is a further aspect of the present invention to provide a method as described above, wherein the carbon source is a saccharide.

It is a further aspect of the present invention to provide a method as described above, wherein the saccharide is glucose.

It is a further aspect of the present invention to provide a method as described above, wherein the microorganism is a bacterium belonging to the family Enterobacteriaceae.

It is a further aspect of the present invention to provide a method as described above, wherein the bacterium belonging to the family Enterobacteriaceae is a bacterium belonging to the genus *Escherichia* or a bacterium belonging to the genus *Pantoea*.

It is a further aspect of the present invention to provide a method as described above, wherein the bacterium belonging to the genus *Escherichia* is *Escherichia coli*, and the bacterium belonging to the genus *Pantoea* is *Pantoea ananatis*.

It is a further aspect of the present invention to provide a method as described above, wherein the carboxyl group-containing compound is a fatty acid.

It is a further aspect of the present invention to provide a method as described above, wherein the fatty acid has 8 to 18 carbon atoms.

It is a further aspect of the present invention to provide a method as described above, wherein the fatty acid has 12 carbon atoms.

It is a further aspect of the present invention to provide a method as described above, wherein the fatty acid is a saturated fatty acid.

It is a further aspect of the present invention to provide a method as described above, wherein the amino group-containing compound is an amino acid, and the enzyme has an N-acylation activity to the amino acid.

It is a further aspect of the present invention to provide a method as described above, wherein the amino acid is L-glutamic acid or L-aspartic acid.

It is a further aspect of the present invention to provide a method as described above, wherein the carboxyl group-containing compound is lauric acid, and the N-acyl-amino group-containing compound is Nα-lauroyl-L-glutamic acid or Nα-lauroyl-L-aspartic acid. It is a further aspect of the present invention to provide a surfactant comprising an N-acyl-amino group-containing compound or a salt thereof produced by the method as described above.

According to a method of the present invention, an N-acyl-amino group-containing compound is produced by a reaction of an amide bond between an amino group-containing compound and a carboxyl group-containing compound.

DETAILED DESCRIPTION OF THE EXEMPLARY EMBODIMENTS

Modified Enzyme

Figure 1:
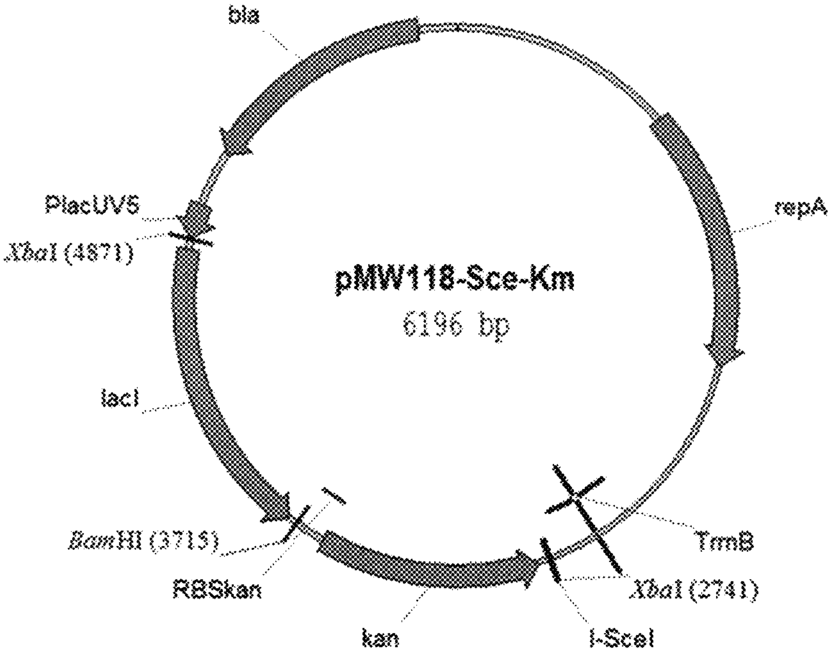
FIG. 1 is a diagram illustrating a structure of a plasmid pMW118-Sce-Km.

Described herein is a modified enzyme having an N-acylation activity.

The modified enzyme is modified based on indole-3-acetic acid-amido synthetase GH3.6 (Q9LSQ4, hereinafter referred to as "AtGH3-6") derived from *Arabidopsis thaliana*. AtGH3-6 was found as an enzyme that bonds a carboxyl group of indole-3-acetic acid and an amino group of a specific amino acid in an ATP-dependent manner to form an amide bond (Plant Cell 17:616-627 (2005)), and was also found to have an N-acylation activity including an ability to form an amide bond between a fatty acid and an amino acid. The modified enzyme has an N-acylation activity, the modified enzyme being obtained by modifying AtGH3-6 to improve a property related to the ability to produce an N-acyl-amino group-containing compound.

The modified enzyme has:

(A) a modified amino acid sequence that includes one or more mutations of predetermined amino acid residues in the amino acid sequence of SEQ ID NO: 1 (wild type AtGH3-6);

(B) an amino acid sequence that includes substitution, deletion, insertion, or addition of one or several additional amino acid residues in the modified amino acid sequence described above; or (C) an amino acid sequence that includes additional mutations of one or more amino acid residues in the modified amino acid sequence as described above, and having 90% or more identity to the modified amino acid sequence, and the modified enzyme has an N-acylation activity as follows: (i) an N-acylation activity to L-glutamic acid and/or L-aspartic acid, and/or a substrate specificity to L-glutamic acid, wherein the activity is improved over an enzyme having the amino acid sequence of SEQ ID NO: 1.

In another embodiment, the modified enzyme includes mutations of predetermined amino acid residues in any of (A') the amino acid sequence shown in SEQ ID NO: 1;

(B') an amino acid sequence that includes substitution, deletion, insertion, or addition of one or several amino acids in the amino acid sequence shown in SEQ ID NO: 1, and (C') an amino acid sequence having 90% or more identity to the amino acid sequence shown in SEQ ID NO: 1, and the modified having an N-acylation activity as follows: an N-acylation activity to L-glutamic acid and/or L-aspartic acid, and/or (ii) a substrate specificity to L-glutamic acid, wherein the activity is improved over an enzyme having the amino acid sequence of SEQ ID NO: 1.

In each of the amino acid sequences (B) and (B'), one or several amino acid residues can be modified by one, two, three, or four kinds of mutations such as deletion, substitution, addition, and insertion of amino acid residues. The mutations of the amino acid residues may be introduced into one region or a plurality of different regions in the amino acid sequence. The term "one or several amino acid residues" refers to the number of the amino acid residues which do not largely impair an activity of the modified enzyme, such as, for example, an N-acylation activity. The term "one or several" refers to the number of, for example, 1 to 60, 1 to 50, 1 to 40, 1 to 30, 1 to 20, 1 to 10, or 1 to 5 (e.g., 1, 2, 3, 4, or 5).

The identity percentage in each of the amino acid sequences (C) and (C') is 90% or more. The identity may be 91% or more, 92% or more, 93% or more, 94% or more, 95% or more, 96% or more, 97% or more, 98% or more, or 99% or more. Calculation of the identity percentage of polypeptides (proteins) can be performed by Algorithm blastp. More specifically, calculation percentage of the identity of polypeptides can be performed using Scoring Parameters (Matrix: BLOSUM62; Gap Costs: Existence=11 Extension=1; Compositional Adjustments: Conditional compositional score matrix adjustment) as default settings in Algorithm blastp provided in National Center for Biotechnology Information (NCBI). Calculation of the identity percentage of polynucleotides (genes) can be performed by Algorithm blastn. More specifically, calculation of the identity percentage of polynucleotides can be performed using Scoring Parameters (Match/Mismatch Scores=1,−2; Gap Costs=Linear) as default settings in Algorithm blastn provided in NCBI.

The "N-acylation activity" (also referred to as "N-acylase activity") refers to an activity of bonding an amino group-containing compound and a carboxyl group-containing compound as substrates to each other by an amide bond to produce an N-acyl-amino group-containing compound. The N-acylation activity may be, for example, an activity of producing an N-acylamino acid from an amino acid, e.g. an α-L-amino acid described below, and a fatty acid, e.g. a saturated fatty acid described below, and an activity of producing Nα-lauroyl-L-glutamic acid or Nα-lauroyl-L-aspartic acid from L-glutamic acid or L-aspartic acid, and lauric acid may be used as an index. The phrase "having an N-acylation activity" may mean having an activity of, for example, 60% or more, 70% or more, 80% or more, 85% or more, 90% or more, 94% or more, 96% or more, 98% or more, or an activity which is equivalent (that is, 100%) or more based on an activity of an enzyme having the amino acid sequence of SEQ ID NO: 1 when the activity is measured under specific measurement conditions. As such specific measurement conditions, the following conditions can be adopted. An enzyme to be measured is prepared as a purified enzyme. A 0.2 mL reaction solution having a pH of 8.0, the reaction solution containing 50 mM Tris-HCl, 5 mM amino acid (e.g., L-glutamic acid or L-aspartic acid), 5 mM sodium fatty acid (e.g., sodium laurate), 10 mM ATP, 10 mM $MgCl_2$, 1 mM DTT, and 50 μg/mL purified enzyme, is incubated at 25° C. for 24 hours. After completion of the reaction, 0.8 mL of a reaction stop solution (1.4% (w/v) phosphoric acid, 75% (v/v) methanol) is added to the reaction solution. The supernatant after centrifugation is subjected to UPLC-MS analysis, and a molecular weight signal that coincides with that of an N-acylamino acid, e.g. Nα-lauroyl-L-glutamic acid or Nα-lauroyl-L-aspartic acid, is measured to evaluate an N-acylation activity.

In each of the amino acid sequences (B), (B'), (C), and (C'), a mutation may be introduced into a site in a catalytic domain and into a site other than the catalytic domain as long as the modified enzyme can maintain the target property. The position of an amino acid residue into which a mutation may be introduced and at which the modified enzyme can maintain the target property is obvious to a person skilled in the art. Specifically, a person skilled in the art can 1) compare amino acid sequences of a plurality of proteins having homogeneous property with each other, 2) clarify a relatively conserved region and a relatively non-conserved region, and then 3) predict a region capable of playing an important role for a function and a region incapable of playing an important role for a function from the relatively conserved region and the relatively non-conserved region, respectively, and can thus recognize structure-function correlation. Therefore, a person skilled in the art can identify the position of an amino acid residue into which a mutation may be introduced in the amino acid sequence of the protein used.

When an amino acid residue is mutated by substitution, the substitution of the amino acid residue may be conservative substitution. The term "conservative substitution" when used in the present specification refers to replacing a certain amino acid residue with an amino acid residue having a similar side chain. Families of the amino acid residue having a similar side chain are known in the field concerned. Examples of such families include an amino acid having a basic side chain, e.g. lysine, arginine, or histidine, an amino acid having an acidic side chain, e.g. aspartic acid or glutamic acid, an amino acid having an uncharged polar side chain, e.g. asparagine, glutamine, serine, threonine, tyrosine, or cysteine, an amino acid having a nonpolar side chain, e.g. glycine, alanine, valine, leucine, isoleucine, proline, phenylalanine, methionine, or tryptophan, an amino acid having a β-position-branched side chain, e.g. threonine, valine, or isoleucine, an amino acid having an aromatic side chain, e.g. tyrosine, phenylalanine, tryptophan, or histidine, an amino acid having a hydroxy group, e.g. alcoholic- or phenolic-containing side chain, e.g. serine, threonine, or tyrosine, and an amino acid having a sulfur-containing side chain, e.g. cysteine or methionine. The conservative substitution of an amino acid may be a substitution between aspartic acid and glutamic acid, substitution among arginine, lysine, and histidine, substitution between tryptophan and phenylalanine, substitution between phenylalanine and valine, substitution among leucine, isoleucine, and alanine, or substitution between glycine and alanine.

The modified enzyme may also be a fusion protein linked to a heterologous moiety via a peptide bond. Examples of such a heterologous moiety include a peptide component that facilitates purification of a target protein, e.g. a tag portion such as a histidine tag or Strep tag II; or a protein used for purification of a target protein, such as glutathione-S-transferase, a maltose binding protein, or mutants thereof, a peptide component that improves a solubility of a target protein, e.g. Nus-tag, a peptide component that acts as a chaperon, e.g. a trigger factor, a peptide component recognized by a protease for cleaving the purification tag, e.g. a Thrombin recognition sequence or a TEV protease recognition sequence, a peptide component having other functions, e.g. a full-length protein or a part thereof, and a linker.

The "mutation of a predetermined amino acid residue" in the amino acid sequence shown in SEQ ID NO: 1 or any of the amino acid sequences (A'), (B'), and (C') is a mutation that improves a property related to an ability to produce an N-acyl-amino group-containing compound in the modified enzyme. Examples of the "mutation of a predetermined amino acid residue" include mutations of amino acid residues N101, R117, T122, 1123, Y134, L137, V140, S161, V174, Q200, V231, V311, C335, T336, M337, A339, S340, Y344, R350, G379, K388, L390, S455, E483, Q533, and C576. More specific examples of the "mutation of a predetermined amino acid residue" include substitutions of amino acid residues N101S, R117P, T122S, I123T, Y134F, Y134V, L137I, V140I, S161P, V174A, Q200E, V231A, V311A, C335S, T336S, M337G, M337A, A339G, S340A, Y344A, Y344G, Y344I, Y344V, R350T, G379D, K388N, L390P, S455T, E483D, Q533R, and C576A. The number of "mutations of predetermined amino acid residues" contained in the modified enzyme is 1 or more, and may be, for example, 1 to 26, 1 to 20, 1 to 15, or 1 to 10 (e.g., 1, 2, 3, 4, 5, 6, 7, 8, 9, or 10).

Examples of the property related to the ability to produce an N-acyl-amino group-containing compound, the property being improved by "mutation of a predetermined amino acid residue", include an N-acylation activity to a specific amino acid substrate and a substrate specificity to a specific amino acid substrate. The degree of improvement is indicated by comparison with an enzyme having the amino acid sequence of SEQ ID NO: 1, and may be measured as comparison between fusion proteins linked to a heterologous moiety via a peptide bond.

Examples of the N-acylation activity to a specific amino acid substrate include an N-acylation activity to L-glutamic acid and an N-acylation activity to L-aspartic acid. A carboxyl group-containing compound that is a substrate used for measuring the N-acylation activity may be, for example, a fatty acid, and is a saturated fatty acid, lauric acid. The N-acylation activity can be measured, for example, under the measurement conditions described above. The degree of improvement in the N-acylation activity to a specific amino acid substrate is not particularly limited as long as the N-acylation activity exceeds an N-acylation activity of an enzyme having the amino acid sequence of SEQ ID NO: 1, but is, for example, 1.1 times or more, 1.2 times or more, 1.3 times or more, 1.5 times or more, and at most 2 times or more.

Examples of the mutation that improves the N-acylation activity to L-glutamic acid or L-aspartic acid include mutations of amino acid residues N101, R117, T122, 1123, Y134, L137, V140, S161, V174, Q200, V231, V311, C335, T336, M337, A339, S340, Y344, R350, G379, K388, L390, S455, E483, Q533, and C576. More specific examples of the mutation that improves the N-acylation activity to L-glutamic acid or L-aspartic acid include substitutions of amino acid residues N101S, R117P, T122S, I123T, Y134F, Y134V, L137I, V140I, S161P, V174A, Q200E, V231A, V311A, C335S, T336S, M337G, M337A, A339G, S340A, Y344A, Y344G, Y344I, Y344V, R350T, G379D, K388N, L390P, S455T, E483D, Q533R, and C576A.

Examples of the substrate specificity to a specific amino acid substrate include a substrate specificity to L-glutamic acid. The substrate specificity to L-glutamic acid can be indicated as an activity ratio between an N-acylation activity to L-glutamic acid and an N-acylation activity to another amino acid (e.g., L-aspartic acid) when the same carboxyl group-containing compound substrate is used. The same carboxyl group-containing compound substrate may be, for example, a fatty acid, and is a saturated fatty acid, lauric acid. The N-acylation activity can be measured, for example, under the measurement conditions described above. The degree of improvement in the substrate specificity to a specific amino acid substrate is not particularly limited as long as the substrate specificity exceeds a substrate specificity of an enzyme having the amino acid sequence of SEQ ID NO: 1, but is, for example, 1.1 times or more, 1.2 times or more, 1.3 times or more, 1.5 times or more, or 2 times or more.

Examples of the mutation that improves the substrate specificity to L-glutamic acid include mutations of amino acid residues N101, R117, T122, 1123, Y134, L137, V140, S161, V174, Q200, V231, V311, C335, T336, M337, A339, S340, Y344, R350, G379, K388, L390, S455, E483, Q533, and C576. More specific examples of the mutation that improves the substrate specificity to L-glutamic acid include substitutions of amino acid residues N101S, R117P, T122S, I123T, Y134F, Y134V, L137I, V140I, S161P, V174A, Q200E, V231A, V311A, C335S, T336S, M337G, M337A, A339G, S340A, Y344A, Y344G, Y344I, Y344V, R350T, G379D, K388N, L390P, S455T, E483D, Q533R, and C576A.

Polynucleotide

The present invention also provides a polynucleotide encoding the modified enzyme as described herein. The polynucleotide may be DNA or RNA, but DNA is a particular example.

The polynucleotide encoding the enzyme may be a polynucleotide such as:

(a) a polynucleotide that includes the nucleotide sequence shown in SEQ ID NO: 2 (wild type AtGH3-6);

(b) a polynucleotide that hybridizes with a polynucleotide having a nucleotide sequence complementary to the nucleotide sequence shown in SEQ ID NO: 2 under stringent conditions;

(c) a polynucleotide that includes a nucleotide sequence having 90% or more identity to the nucleotide sequence shown in SEQ ID NO: 2; and (d) a degenerate variant of any of the polynucleotide described above, The polynucleotide may encode a modified enzyme, and the polynucleotide may include mutations of nucleotide sequences corresponding to mutations of the predetermined amino acid residues described above, and wherein the modified enzyme has an N-acylation activity as follows: (i) an N-acylation activity to L-glutamic acid and/or L-aspartic acid; and/or (ii) a substrate specificity to L-glutamic acid, wherein the activity is improved over an enzyme having the amino acid sequence of SEQ ID NO: 1. The nucleotide sequence of SEQ ID NO: 2 encodes the amino acid sequence of SEQ ID NO: 1.

In the polynucleotide (b), the term "stringent conditions" refers to conditions under which a so-called specific hybrid is formed and a non-specific hybrid is not formed. Examples of the stringent conditions include hybridization at about 45° C. in 6×SSC (sodium chloride/sodium citrate) followed by washing once or more at 50 to 65° C. in 0.2 × SSC and 0.1% SDS.

In the polynucleotide (c), the identity percentage of a nucleotide sequence to the nucleotide sequence of SEQ ID NO: 2 may be 90% or more, 91% or more, 92% or more, 93% or more, 94% or more, 95% or more, 96% or more, 97% or more, 98% or more, or 99% or more.

In the polynucleotide (d), the term "degenerate variant" refers to a polynucleotide mutant in which at least one codon encoding a certain amino acid residue in a polynucleotide before mutation has been changed into another codon encoding the same amino acid residue. Since such a degenerate variant is a variant based on a silent mutation, a protein (enzyme) encoded by the degenerate variant is the same as a protein (enzyme) encoded by a polynucleotide before mutation.

The degenerate variant is a polynucleotide mutant in which a codon has been changed so as to be adapted to a codon usage frequency of a host cell into which the degenerate variant is to be introduced. When a gene is expressed by a heterologous host cell, e.g. a microorganism, due to a difference in codon usage frequency, a corresponding tRNA molecular species is not sufficiently supplied, which may cause a reduction in translation efficiency and/or incorrect translation, e.g. stop of translation. In *Escherichia coli*, for example, low frequency codons listed in Table 1 are known.

TABLE 1

Low frequency codon in *Escherichia coli*

| Amino acid residue | Codon | Low frequency codon |
|---|---|---|
| Arg | AGG/AGA/CGG/CGA/CGU/CGC | AGG/AGA/CGG/CGA |
| Gly | GGG/GGA/GGU/GGC | GGA |
| Ile | AUA/AUU/AUC | AUA |
| Leu | UUG/UUA/CUG/CUA/CUU/CUC | CUA |
| Pro | CCG/CCA/CCU/CCC | CCC |

Therefore, the present invention can use a degenerate variant adapted to the codon usage frequency of a host cell described below. In the degenerate variant, for example, a codon or codons encoding one or more kinds of amino acid residues such as an arginine residue, a glycine residue, an isoleucine residue, a leucine residue, and a proline residue may be changed. More specifically, in the degenerate variant, one or more kinds of low frequency codons, e.g. AGG, AGA, CGG, CGA, GGA, AUA, CUA, and CCC, may be changed. The degenerate variant may contain changes of one or more kinds, e.g. one, two, three, four, or five kinds, of codons such as:

i) a change of at least one of four kinds of codons, AGG, AGA, CGG, and CGA encoding Arg into another codon, CGU or CGC encoding Arg;

ii) a change of one kind of codon, GGA encoding Gly into another codon, GGG, GGU, or GGC;

iii) a change of one kind of codon, AUA encoding Ile into another codon, AUU or AUC;

iv) a change of one kind of codon, CUA encoding Leu into another codon, UUG, UUA, CUG, CUU, or CUC; and v) a change of one kind of codon, CCC encoding Pro into another codon, CCG, CCA, or CCU.

When the degenerate variant is RNA, the nucleotide residue "U" should be used as described above, whereas when the degenerate variant is DNA, "T" should be used in place of the nucleotide residue "U". The number of mutations of nucleotide residues for being adapted to the codon usage frequency of a host cell, which is not particularly limited as long as the same protein is encoded before and after mutation, is, for example, 1 to 400, 1 to 300, 1 to 200, or 1 to 100.

A low frequency codon can be easily identified based on the kind and genome sequence information of any host cell by using techniques known in the field concerned. Therefore, the degenerate variant may contain a change of a low frequency codon into a non-low frequency codon, e.g. a high frequency codon. In addition, since a method for designing a mutant in consideration of a factor such as adaptability to the genomic GC content of a producing strain as well as a low frequency codon is known (Alan Villalobos et al., Gene Designer: a synthetic biology tool for constructing artificial DNA segments, BMC Bioinformatics. 2006 Jun. 6; 7:285), such a method may be used. Thus, the mutant described above can be appropriately prepared in accordance with any kind of host cell, e.g. a microorganism described below, into which the mutant can be introduced.

Expression Vector

Described herein is an expression vector. The expression vector contains the polynucleotide as described herein or a polynucleotide encoding the modified enzyme.

The term "expression unit" refers to a minimum unit that contains a certain polynucleotide to be expressed as a protein, and a promoter operably linked thereto, and enables transcription of the polynucleotide and consequently production of a protein encoded by the polynucleotide. The expression unit may further contain an element such as a terminator, a ribosome binding site, or a drug-resistant gene. The expression unit may be DNA or RNA, and DNA is a particular example. The expression unit may be homologous, that is, inherent, or heterologous, that is, non-inherent, relative to a host cell. The expression unit may be an expression unit containing one polynucleotide to be expressed as a protein and a promoter operably linked thereto, that is, an expression unit that enables expression of monocistronic mRNA, or an expression unit containing a plurality of polynucleotides to be expressed as a protein, e.g. 2 or more, 3 or more, 4 or more, 5 or more, or 10 or more polynucleotides, and a promoter operably linked thereto, that is, an expression unit that enables expression of polycistronic mRNA. The expression unit can be contained in a genomic region, e.g., a natural genomic region that is a natural locus in which a polynucleotide encoding the protein is inherently present, or a non-natural genomic region that is not the natural locus, or a non-genomic region, e.g. in a cytoplasm, in a microorganism or host cell. The expression unit may be contained in a genomic region at one or more, e.g. 1, 2, 3, 4, or 5, different positions. Examples of a specific form of the expression unit contained in the non-genomic region include a plasmid, a viral vector, a phage, and an artificial chromosome.

The promoter present in the expression unit is not particularly limited as long as the promoter can express a protein (enzyme) encoded by a polynucleotide linked to a downstream side thereof in a host cell. For example, the promoter may be homologous or heterologous relative to a host cell. For example, a constitutive or inducible promoter generally used for production of a recombinant protein can be used. Examples of such a promoter include a PhoA promoter, a PhoC promoter, a T7 promoter, a T5 promoter, a T3 promoter, a lac promoter, a trp promoter, a tre promoter, a tac promoter, a PR promoter, a PL promoter, an SP6 promoter, an arabinose-inducible promoter, a cold shock promoter, and a tetracycline-inducible promoter. A promoter having a strong transcription activity in a host cell can be used. Examples of the promoter having a strong transcription activity in a host cell include a promoter of a gene highly expressed in the host cell and a promoter derived from a virus.

The expression vector may further contain, as the expression unit, an element such as a terminator that functions in a host cell, a ribosome binding site, or a drug-resistant gene in addition to the minimum unit described above. Examples of the drug-resistant gene include a gene resistant against a drug such as tetracycline, ampicillin, kanamycin, hygromycin, phosphinothricin, or chloramphenicol.

The expression vector may further contain a region which enables homologous recombination with a genome of a host cell for homologous recombination with the genome DNA of the host cell. For example, the expression vector may be designed such that an expression unit contained therein is positioned between a pair of homologous regions, e.g., homology arms homologous to a specific sequence in a genome of a host cell, loxP or FRT. The genome region, such as a target of the homologous region, of the host cell into which the expression unit is to be introduced is not particularly limited, but may be a locus of a gene having a large amount of expression in the host cell.

The expression vector may be a plasmid, a virus vector, a phage, or an artificial chromosome. The expression vector may be an integrative vector or a non-integrative vector. The integrative vector may be a vector the entire of which is incorporated into a genome of a host cell. Alternatively, the integrative vector may be a vector only a part of which is incorporated into a genome of a host cell, such as an expression unit. Furthermore, the expression vector may be a DNA vector or an RNA vector (e.g., a retrovirus). The expression vector may be a generally used expression vector. Examples of such an expression vector include pUC, e.g. pUC19 or pUC18, pSTV, pBR, e.g. pBR322, pHSG, e.g., pHSG299, pHSG298, pHSG399, or pHSG398, RSF, e.g. RSF1010, pACYC, e.g. pACYC177 or pACYC184, pMW, e.g. pMW119, pMW118, pMW219, or pMW218, pQE, e.g. pQE30, pET, e.g. pET28a, and derivatives thereof.

Host Cell

Described herein is a host cell. The host cell contains an expression unit of a polynucleotide encoding the modified enzyme. The host cell contains an expression unit containing a polynucleotide encoding the modified enzyme and a promoter operably linked thereto. The host cell is a microorganism.

The host cell is a transformed microorganism. Examples of the host cell include a bacterium such as a bacterium belonging to the family Enterobacteriaceae, and fungi. The bacterium may also be a Gram-positive bacterium or a Gram-negative bacterium. Examples of the gram-positive bacterium include a bacterium belonging to the genus *Bacillus* and a bacterium belonging to the genus *Corynebacterium*. The bacterium belonging to the genus *Bacillus* can be *Bacillus subtilis*. The bacterium belonging to the genus *Corynebacterium* can be *Corynebacterium glutamicum*. Examples of the Gram-negative bacterium include a bacterium belonging to the genus *Escherichia* and a bacterium belonging to the genus *Pantoea*. The bacterium belonging to the genus *Escherichia* can be *Escherichia coli*. The bacterium belonging to the genus *Pantoea* can be *Pantoea ananatis*. The fungus can be a microorganism belonging to the genus *Saccharomyces* or belonging to the genus *Schizosaccharomyces*. The microorganism belonging to the genus *Saccharomyces* can be *Saccharomyces cerevisiae*. The microorganism belonging to the genus *Schizosaccharomyces* can be *Schizosaccharomyces pombe*. The host cell is a bacterium belonging to the family Enterobacteriaceae, a bacterium belonging to the genus *Escherichia* or belonging to the genus *Pantoea*, and *Escherichia coli* or *Pantoea ananatis*.

In one embodiment, the host cell can be used for producing an N-acyl-amino group-containing compound or a salt thereof by the modified enzyme produced in the host cell using the host cell itself, e.g. a cultured product of the host cell, or a treated product thereof, e.g. a disrupted product, a lysate, or a lyophilizate of the host cell. In another embodiment, the host cell can be used for obtaining the modified enzyme as an unpurified, crude, or purified enzyme.

When the host cell is used for producing an N-acyl-amino group-containing compound or a salt thereof, the host cell may be, for example, a host having enhanced ability to incorporate an amino acid and/or a fatty acid in order to improve supply efficiency of a substrate of an enzymatic reaction to improve production efficiency. Examples of the host having the enhanced incorporating ability include a host that produces or enhances a protein such as an enzyme related to the incorporating ability. Examples of the host that produces or enhances a protein such as an enzyme related to the incorporating ability include a host into which an expression unit of the protein is introduced by transformation, a host containing a mutation that enhances the amount of expression of the protein in a host genome, and a host containing a mutation that enhances an activity of the protein in the host genome. Such a host cell can be used for producing an N-acyl-amino group-containing compound, e.g., an N-acylamino acid, or a salt thereof by culturing the host cell in a culture solution containing an amino group-containing compound, e.g. an amino acid and/or a carboxyl group-containing compound, e.g., a fatty acid. Furthermore, such a host cell can be used for producing (direct fermentation method) an N-acyl-amino group-containing compound, e.g. an N-acylamino acid, or a salt thereof by culturing the host cell in a culture solution containing a carbon source, e.g. a saccharide such as glucose.

In order to suppress a loss of a substrate of an enzymatic reaction and/or to promote supply of the substrate of the enzymatic reaction or to suppress a loss of a product, the host cell may be, for example, a host cell having at least one genetic modification such as:

(1) enhancement of ability to supply a fatty acid;
(2) enhancement of ability to supply an amino acid;
(3) enhancement of ability to supply ATP; and
(4) deficiency or attenuation of an N-acylamino acid degrading enzyme.

The host cell having a genetic modification effective for enhancement of ability to supply a fatty acid may be a host cell in which a fatty acid degradation system is attenuated or deficient and/or a fatty acid synthesis system is enhanced.

Examples of the host cell in which the fatty acid degradation system is attenuated or deficient include a host cell in which a protein such as an enzyme related to the degradation system is attenuated or deficient and a host cell that produces an inhibitor of a protein such as an enzyme related to the degradation system.

Examples of the host cell in which a protein such as an enzyme related to the fatty acid degradation system is attenuated or deficient include a host cell containing a mutation that reduces or deletes the amount of expression of the protein in a host cell genome and a host cell containing a mutation that reduces or deletes an activity of the protein in the host cell genome.

Examples of the host cell that produces or enhances an inhibitor of a protein such as an enzyme related to the fatty acid degradation system include a host cell into which an expression unit of the inhibitor is introduced by transformation, a host cell containing a mutation that enhances the amount of expression of the inhibitor in a host cell genome, and a host cell containing a mutation that enhances an activity of the inhibitor in the host cell genome.

More specifically, examples of the protein such as an enzyme related to the fatty acid degradation system include acyl CoA synthetase (fadD), acyl CoA dehydrogenase (fadE), enoyl CoA hydratase (fadB and fadJ), 3-hydroxyacyl CoA dehydrogenase (fadB and fadJ), and 3-ketoacyl CoA thiolase (fadA and fadI). Note that the name in the parenthesis after the enzyme name is a gene name thereof and the same applies to the following description. Among these enzymes, for example, acyl CoA synthetase is preferable.

Examples of the host cell in which the fatty acid synthesis system is enhanced include a host cell that produces or enhances a protein such as an enzyme related to the synthesis system.

Examples of the host cell that produces or enhances a protein such as an enzyme related to the synthesis system include a host cell into which an expression unit of the protein is introduced by transformation, a host cell containing a mutation that enhances the amount of expression of the protein in a host cell genome, and a host cell containing a mutation that enhances an activity of the protein in the host cell genome.

More specifically, examples of the protein such as an enzyme related to the fatty acid synthesis system include acyl-ACP thioesterase, acetyl COA carboxylase (accABCD), malonyl CoA-ACP transacylase (fabD), β-ketoacyl ACP synthase III (fabH), β-ketoacyl ACP reductase (fabG), β-hydroxyacyl ACP dehydratase (fabZ), enoyl ACP reductase (fabI), β-ketoacyl ACP synthase I (fabB), and β-ketoacyl ACP synthase II (fabF). Among these enzymes, for example, acyl-ACP thioesterase is a particular example.

The genetic modification for enhancement of ability to supply a fatty acid may be.

(a) deficiency or attenuation of acyl CoA synthetase; and/or (b) enhancement of acyl-ACP thioesterase.

Examples of the deficiency or attenuation of acyl CoA synthetase include deletion or mutagenesis of a fadD gene on a host cell genome.

Examples of the enhancement of acyl-ACP thioesterase include introduction of an acyl-ACP thioesterase expression unit into a host cell.

The acyl-ACP thioesterase may be, for example, an acyl-ACP thioesterase having a thioesterase activity to lauroyl-ACP. In addition, the acyl-ACP thioesterase may be, for example, a protein as follows:

(i) a protein including (i-1) an amino acid sequence of SEQ ID NO: 3 or (i-2) the amino acid sequence having the amino acid residues at positions 84 to 382 in the amino acid sequence of SEQ ID NO: 3;

(ii) a protein including an amino acid sequence that includes substitution, deletion, insertion, or addition of one or several amino acids in (ii-1) the amino acid sequence of SEQ ID NO: 3 or (ii-2) the amino acid sequence having amino acid residues at positions 84 to 382 in the amino acid sequence of SEQ ID NO: 3, and having an acyl-ACP thioesterase activity; and (iii) a protein including an amino acid sequence having 90% or more identity to (iii-1) the amino acid sequence of SEQ ID NO: 3 or (iii-2) the amino acid sequence having amino acid residues at positions 84 to 382 in the amino acid sequence of SEQ ID NO: 3, and having acyl-ACP thioesterase activity.

The host cell having a genetic modification effective for enhancement of ability to supply an amino acid may be a host cell in which an amino acid degradation system is attenuated or deficient and/or an amino acid synthesis system is enhanced.

Examples of the host cell in which an amino acid degradation system is attenuated or deficient include a host cell in which a protein such as an enzyme related to the amino acid degradation system is attenuated or deficient and a host cell that produces an inhibitor of a protein such as an enzyme related to the amino acid degradation system.

Examples of the host cell in which a protein such as an enzyme related to the amino acid degradation system is attenuated or deficient include a host cell containing a mutation that reduces or deletes the amount of expression of the protein in a host cell genome and a host cell containing a mutation that reduces or deletes an activity of the protein in the host cell genome.

Examples of the host cell that produces or enhances an inhibitor of a protein such as an enzyme related to the amino acid degradation system include a host cell into which an expression unit of the inhibitor is introduced by transformation, a host cell containing a mutation that enhances the amount of expression of the inhibitor in a host cell genome, and a host cell containing a mutation that enhances an activity of the inhibitor in the host cell genome.

More specifically, the protein such as an enzyme related to the amino acid degradation system may be an enzyme that catalyzes a reaction of branching from a biosynthetic pathway of a target amino acid, e.g. L-glutamic acid to produce a compound other than the target amino acid. Examples of such an enzyme include α-ketoglutarate dehydrogenase (sucA), isocitrate lyase (aceA), succinate dehydrogenase (sdhABCD), phosphotransacetylase (pta), acetate kinase (ack), acetohydroxyate synthase (ilvG), acetolactate synthase (ilvI), formate acetyltransferase (pfl), lactate dehydrogenase (ldh), glutamate decarboxylase (gadAB), and 1-pyrroline-5-carboxylate dehydrogenase (putA). Among these enzymes, for example, «-ketoglutarate dehydrogenase is a particular example.

Examples of the host cell in which the amino acid synthesis system is enhanced include a host cell that produces or enhances a protein such as an enzyme related to the amino acid synthesis system.

Examples of the host cell that produces or enhances a protein such as an enzyme related to the amino acid synthesis system include a host cell into which an expression unit of a protein of the amino acid is introduced by transformation, a host cell containing a mutation that enhances the amount of expression of the protein in a host cell genome, and a host cell containing a mutation that enhances an activity of the protein in the host cell genome.

More specifically, examples of the protein such as an enzyme related to the amino acid, e.g. glutamic acid synthesis system include glutamate dehydrogenase (gdhA), glutamine synthetase (glnA), glutamate synthase (gltBD), isocitrate dehydrogenase (icdA), aconitate hydratase (acnA and acnB), citrate synthase (gltA), methyl citrate synthase (prpC), phosphoenolpyruvate carboxylase (ppc), pyruvate carboxylase (pyc), pyruvate kinase (pykA and pykF), pyruvate dehydrogenase (aceEF and lpdA), phosphoenolpyruvate synthase (ppsA), enolase (eno), phosphoglyceromutase (pgmA and pgmI), phosphoglycerate kinase (pgk), glyceraldehyde-3-phosphate dehydrogenase (gapA), triosphosphate isomerase (tpiA), fructose bisphosphate aldolase (fbp), phosphofructokinase (pfkA and pfkB), glucose phosphate isomerase (pgi), 6-phosphogluconate dehydratase (edd), 2-keto-3-deoxy-6-phosphogluconate aldolase (eda), and transhydrogenase.

The host cell having a genetic modification effective for enhancement of ability to supply ATP may be a host cell in which an ATP degradation system is attenuated or deficient and/or an ATP synthesis system is enhanced.

Examples of the host cell in which the ATP degradation system is attenuated or deficient include a host cell in which a protein such as an enzyme related to the ATP degradation system is attenuated or deficient.

Examples of the host cell in which a protein such as an enzyme related to the ATP degradation system is attenuated or deficient include a host cell containing a mutation that reduces or deletes the amount of expression of the protein in a host cell genome and a host cell containing a mutation that reduces or deletes an activity of the protein in the host cell genome.

Examples of the host cell in which the ATP synthesis system is enhanced include a host cell that produces or enhances a protein such as an enzyme related to the synthesis system.

Examples of the host cell that produces or enhances a protein such as an enzyme related to the ATP synthesis system include a host cell into which an expression unit of the protein is introduced by transformation, a host cell containing a mutation that enhances the amount of expression of the protein in a host cell genome, and a host cell containing a mutation that enhances an activity of the protein in the host cell genome.

Examples of a genetic modification effective for deficiency or attenuation of an N-acylamino acid degrading enzyme include deficiency or attenuation of acylase. Examples of the deficiency or attenuation of acylase include deletion or mutagenesis of an acylase gene on a host cell genome.

Such a host cell can be used for producing, such as by e.g. an enzyme method, an N-acyl-amino group-containing compound, e.g. an N-acylamino acid, or a salt thereof in a reaction solution containing an amino group-containing compound, e.g. an amino acid, and a carboxyl group-containing compound, e.g. a fatty acid, as a transformed microorganism, e.g. a cultured product of the microorganism, that produces the enzyme or a treated product thereof, e.g. a disrupted product, a lysate, or a lyophilizate of the microorganism. Such a host cell can be used for producing an N-acyl-amino group-containing compound, e.g. an N-acylamino acid, or a salt thereof by culturing the host cell in a culture solution containing an amino group-containing compound, e.g. an amino acid, and/or a carboxyl group-containing compound, e.g. a fatty acid. Furthermore, such a host cell has an enhanced metabolic pathway for producing an amino group-containing compound, e.g. an amino acid, and/or a carboxyl group-containing compound, e.g. a fatty acid, from a carbon source, e.g. a saccharide such as glucose, and therefore can be used for producing, such as by a direct fermentation method, an N-acyl-amino group-containing compound, e.g. an N-acylamino acid, or a salt thereof by culturing the host cell in a culture solution containing a carbon source.

The transformed microorganism can be produced by any method known in the field concerned. For example, such a transformed microorganism as described above can be produced by a method using an expression vector, such as by, e.g. a competent cell method or an electroporation method, or a genome modification technique. When the expression vector is an integrative vector that causes homologous recombination with the genome DNA of a host cell, an expression unit can be incorporated into the genome DNA of the host cell by transformation. On the other hand, when the expression vector is a non-integrative vector that does not cause homologous recombination with the genome DNA of the host cell, the expression unit is not incorporated into the genome DNA of the host cell by transformation, and can exist independently of the genome DNA in the host cell in the state of the expression vector. Alternatively, according to genome editing technology, such as e.g. CRISPR/Cas system, Transcription Activator-Like Effector Nucleases (TALEN), it is possible to incorporate an expression unit into the genome DNA of a host cell and to modify an expression unit inherently contained in the host cell.

Method for Producing N-Acyl-Amino Group-Containing Compound or Salt Thereof

Described herein is a method for producing an N-acyl-amino group-containing compound or a salt thereof. The method includes producing an N-acyl-amino group-containing compound or a salt thereof by reacting an amino group-containing compound and a carboxyl group-containing compound in the presence of a modified enzyme having an N-acylation activity.

The modified enzyme used in the method may be the modified enzyme described above.

Amino Group-Containing Compound

The amino group-containing compound that can be used in the method may be either an organic compound containing an amino group in which a nitrogen atom is bonded to one or two hydrogen atoms, or an organic compound containing an amino group in which a nitrogen atom is not bonded to a hydrogen atom. The amino group-containing compound is a compound containing an amino group in which a nitrogen atom is bonded to one or two hydrogen atoms, andcan be a compound containing an amino group in which a nitrogen atom is bonded to two hydrogen atoms from a viewpoint of a substrate specificity of the enzyme, and the like.

The amino group-containing compound that can be used in the method can be an amino group-containing compound having an anionic group. Examples of the anionic group include a carboxyl group, a sulfonic acid group, a sulfuric acid group, and a phosphoric acid group.

Examples of the amino group-containing compound having a carboxyl group as an anionic group include an amino acid and a peptide.

Examples of the amino acid include an α-amino acid, a β-amino acid, and a Y-amino acid. Examples of the x-amino acid include glycine, alanine, valine, leucine, isoleucine, proline, methionine, phenylalanine, tryptophan, serine, threonine, asparagine, glutamine, tyrosine, cysteine, aspartic acid, glutamic acid, histidine, lysine, and arginine. Examples of the β-amino acid include β-alanine. Examples of the γ-amino acid include γ-aminobutyric acid. The amino group of the amino acid may be any of an amino group in which a nitrogen atom is bonded to two hydrogen atoms, an amino group in which a nitrogen atom is bonded to one hydrogen atom, and an amino group in which a nitrogen atom is not bonded to a hydrogen atom. Examples of the amino acid containing an amino group in which a nitrogen atom is bonded to one hydrogen atom include sarcosine, N-methyl-β-alanine, N-methyltaurine, and proline. The amino acid may be either an L-amino acid or a D-amino acid.

The peptide is a compound having a structure in which the above-described amino acids are linked to each other by an amide bond. Examples of the peptide include an oligopeptide, e.g. dipeptide, tripeptide, tetrapeptide, pentapeptide, hexapeptide, heptapeptide, or octapeptide, having a structure in which 2 to 10 amino acids are linked to each other by an amide bond, and a polypeptide (protein) having a structure in which 11 or more amino acids are linked to each other by an amide bond. Examples of the dipeptide include aspartylphenylalanine, glycylglycine, β-alanylhistidine, and alanylglutamine.

Examples of the amino group-containing compound having a sulfonic acid group as an anionic group include taurine, N-methyl taurine, and cysteic acid.

Examples of the amino group-containing compound having a sulfuric acid group as an anionic group include O-sulfoserine and O-sulfothreonine.

Examples of the amino group-containing compound having a phosphoric acid group as an anionic group include ethanolamine phosphate, phosphoserine, and phosphothreonine.

The amino group-containing compound that can be used in the method can be an acidic amino acid. The “acidic amino acid” refers to an amino acid having an acidic side chain. Examples of the acidic amino acid include glutamic acid and aspartic acid, and glutamic acid is preferable.

Carboxyl Group-Containing Compound

The carboxyl group-containing compound that can be used in the method is a compound containing a carboxyl group without a substituent, such as e.g. a free form, an ion, or a salt. Examples of the carboxyl group-containing compound include a fatty acid, an aromatic carboxylic acid, an indole carboxylic acid, and a mixture thereof. The carboxyl group-containing compound can be a fatty acid.

The fatty acid may be, for example, a fatty acid having 8 to 18 carbon atoms, and can be a fatty acid having 12 carbon atoms. Examples of the fatty acid having 6 to 18 carbon atoms include caproic acid (C6), enanthic acid (C7), caprylic acid (C8), pelargonic acid (C9), capric acid (C10), decenoic acid (C10: 1), undecylic acid (C11), lauric acid (C12), dodecenoic acid (C12: 1), tridecylic acid (C13), myristic acid (C14), tetradecenoic acid (C14: 1) (e.g., myristoleic acid), pentadecylic acid (C15), palmitic acid (C16), hexadecenoic acid (C16: 1) (e.g., palmitoleic acid or sapienic acid), margaric acid (C17), stearic acid (C18), octadecenoic acid (C18:1) (e.g., oleic acid or vaccenic acid), linoleic acid (C18: 2), and linolenic acid (C18: 3), e.g. α-linolenic acid or γ-linolenic acid. The number in parentheses indicates the number of carbon atoms. In addition to these, a mixed fatty acid such as a coconut oil fatty acid, a palm fatty acid, or a hydrogenated beef tallow fatty acid can also be used.

The fatty acid may be a saturated fatty acid. Among the fatty acids, examples of the saturated fatty acid include caproic acid, enanthic acid, caprylic acid, pelargonic acid, capric acid, undecylic acid, lauric acid, tridecylic acid, myristic acid, pentadecylic acid, palmitic acid, margaric acid, and stearic acid. The saturated fatty acid can be lauric acid. The fatty acid may be an unsaturated saturated fatty acid. Among the fatty acids, examples of the unsaturated fatty acid include decenoic acid (C10: 1), dodecenoic acid (C12: 1), tetradecenoic acid (C14: 1), e.g. myristoleic acid, hexadecenoic acid (C16: 1), e.g. palmitoleic acid or sapienic acid, octadecenoic acid (C18: 1), e.g. oleic acid or vaccenic acid, linoleic acid (C18: 2), and linolenic acid (C18: 3), e.g. α-linolenic acid or γ-linolenic acid. The number in parentheses indicates the number of carbon atoms. The unsaturated fatty acid can be dodecenoic acid (C12: 1) or hexadecenoic acid (C16: 1). A mixture of these fatty acids may be used as the fatty acid.

Examples of the aromatic carboxylic acid include benzoic acid, phthalic acid, isophthalic acid, terephthalic acid, salicylic acid, gallic acid, cinnamic acid, and a mixture thereof.

N-Acyl-Amino Group-Containing Compound or Salt Thereof

The N-acyl-amino group-containing compound or a salt thereof produced by the method is a compound having a structure in which an amino group of the amino group-containing compound and a carboxyl group of the carboxyl group-containing compound form an amide bond. The N-acyl-amino group-containing compound or a salt thereof is produced by a reaction between the amino group-containing compound and the carboxyl group-containing compound in the presence of the enzyme. The amino group that reacts with a carboxyl group may be at any position of the amino group-containing compound, and may be, for example, at any of an α-position, a β-position, a γ-position, a δ-position, and an ε-position. The N-acyl-amino group-containing compound or a salt thereof produced by the method can be Nα-acyl-L-glutamic acid or Nα-acyl-L-aspartic acid, or a salt thereof, or Nα-lauroyl-L-glutamic acid or Nα-lauroyl-L-aspartic acid, or a salt thereof. Examples of the salt of the N-acyl-amino group-containing compound include an inorganic salt and an organic salt. Examples of the inorganic salt include a salt of a metal, e.g., a monovalent metal such as lithium, sodium, potassium, rubidium, or cesium, or a divalent metal such as calcium, magnesium, or zinc, and a salt of an inorganic base, e.g. ammonia. Examples of the organic salt include a salt of an organic base, e.g. ethylenediamine, propylenediamine, ethanolamine, monoalkylethanolamine, dialkylethanolamine, diethanolamine, triethanolamine, lysine, arginine, histidine, or ornithine.

The “acyl having n carbon atoms” refers to an acyl represented by $C_{n-1}H_m$—CO—, in which a hydrogen atom may be replaced. Here, “m” is appropriately determined according to the number of carbon atoms and the presence or absence of an unsaturated bond.

The “N-monounsaturated acyl-amino group-containing compound, wherein the unsaturated acyl is a monounsaturated acyl having 10 to 16 carbon atoms” refers to a compound represented by $C_{n-1}H_m$—CO—NH—CHR—COOH, in which the hydrogen atom represented by $H_m$ may be replaced, “m” is as defined above, and R represents a side chain of an acidic amino acid, as a free form. That is, the “N-monounsaturated acyl-amino group-containing compound” refers to a compound in which one hydrogen atom on an amino group of an acidic amino acid is replaced with an unsaturated acyl group. The “N-monounsaturated acyl-amino group-containing compound” may be a free form of an N-monounsaturated acyl-amino group-containing compound or a salt of the N-monounsaturated acyl-amino group-containing compound.

The N-monounsaturated acyl-amino group-containing compound may be derived from a fatty acid represented by $C_{n-1}H_m$—COOH or a derivative thereof for convenience. In addition, in the present specification, an “unsaturated acyl having n carbon atoms” and a fatty acid and the like from which the unsaturated acyl having n carbon atoms is derived may be represented by “Cn: m”. For example, “N-dodecenonyl acidic amino acid (C12: 1)” refers to a compound in which one hydrogen atom on an amino group of an acidic amino acid is replaced with a dodecenonyl group which is an acyl group derived from dodecenoic acid (C12: 1), $C_{11}H_{21}$CO—NH—CHR—COOH in which R represents a side chain of the acidic amino acid.

When the N-acyl-amino group-containing compound or a salt thereof produced by the method contains an N-monounsaturated acyl-amino group-containing compound or a salt thereof, examples of the N-monounsaturated acyl-amino group-containing compound include N-decenoyl acidic amino acid (C10: 1), N-dodecenoyl acidic amino acid (C12: 1), N-tetradecenoyl acidic amino acid (C14: 1), and N-hexadecenoyl acidic amino acid (C16: 1). N-dodecenoyl acidic amino acid (C12: 1) or N-hexadecenoyl acidic amino acid (C16: 1) is preferable. N-dodecenoyl glutamic acid (C12: 1) or N-hexadecenoyl glutamic acid (C16: 1) are particular examples.

The N-monounsaturated acyl-amino group-containing compound may include one kind of N-monounsaturated acyl-amino group-containing compound, or two or more kinds of N-monounsaturated acyl-amino group-containing compounds. That is, the N-monounsaturated acyl-amino group-containing compound may include one or more of N-decenoyl acidic amino acid (C10: 1), N-dodecenoyl acidic amino acid (C12: 1), N-tetradecenoyl acidic amino acid (C14: 1), and N-hexadecenoyl acidic amino acid (C16:

1). When two or more kinds of N-monounsaturated acyl-amino group-containing compounds are used, a combination of N-dodecenoyl acidic amino acid (C12: 1) and one or more of N-decenoyl acidic amino acid (C10: 1), N-tetradecenoyl acidic amino acid (C14: 1), and N-hexadecenoyl acidic amino acid (C16: 1) is a particular example, and a combination of N-dodecenoyl acidic amino acid (C12: 1) and N-hexadecenoyl acidic amino acid (C16: 1) is a particular example from the viewpoint of improving foam quality.

The N-monounsaturated acyl-amino group-containing compound is a compound represented by the following general formula (A):

(A)

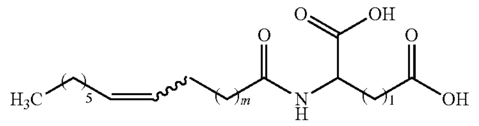

In general formula (A), "1" is an integer of 1 or 2, and "m" is an integer of 0 to 6.

The stereochemistry (unsaturated double bond site) of the N-monounsaturated acyl-amino group-containing compound may be either in a cis or trans conformation. However, cis is a particular example from the viewpoint of suppressing an increase in viscosity and achieving a low viscosity with high handleability.

Production of N-Acyl-Amino Group-Containing Compound by Enzyme Method

As the enzyme used in the method, a recombinant protein can be used. The recombinant protein can be obtained, for example, using a cell-free vector or from a microorganism that produces the enzyme. The enzyme can be an unpurified, crude, or purified enzyme. These enzymes may be used as a solid-phase protein immobilized on a solid phase in a reaction. The enzyme used can be used in a form of a transformed microorganism, e.g., a cultured product of the microorganism, that produces the enzyme or a treated product thereof, e.g., a disrupted product, a lysate, or a lyophilizate of the microorganism.

The enzyme used in the method is isolated by a known method, and further purified as necessary to obtain a desired enzyme. As the microorganism that produces the enzyme, a transformed microorganism is preferable from a viewpoint of obtaining a large amount of the enzyme, and the like. The term "transformation" is intended not only for introduction of a polynucleotide into a host cell but also for modification of a genome in the host cell.

Culture conditions of the transformed microorganism are not particularly limited, and standard cell culture conditions can be used depending on a host. A medium for culturing the transformed microorganism is known, and for example, a carbon source, a nitrogen source, a vitamin source, or the like can be added to a nutrient medium such as an LB medium or a minimum medium such as an M9 medium.

Culture temperature is 4 to 40° C., or 10 to 37° C. Culture time is 5 to 168 hours, or 8 to 72 hours. As a gas composition, a $CO_2$ concentration is about 6% to about 84%, and a pH of about 5 to 9 is preferable. In addition, culture is performed under aerobic, anoxic, or anaerobic conditions depending on the properties of a host cell.

As a culturing method, any appropriate method can be used. Depending on a host cell, either shaking culture or static culture is possible, but stirring may be performed as necessary, or aeration may be performed. Examples of such a culture method include a batch culture method, a fed-batch culture method, and a continuous culture method. When expression of a specific protein produced by the transformant microorganism is under control of an inducible promoter such as a lac promoter, an inducer such as isopropyl-β-thiogalactopyranoside (IPTG) may be added to a culture medium to induce the expression of the protein.

The produced target enzyme can be purified and isolated from the extract of the transformed microorganism by known salting out, a precipitation method such as an isoelectric point precipitation method or a solvent precipitation method, a method using a molecular weight difference, such as dialysis, ultrafiltration, or gel filtration, a method using specific affinity, such as ion exchange chromatography, a method using a difference in hydrophobicity, such as hydrophobic chromatography or reverse phase chromatography, affinity chromatography, SDS polyacrylamide electrophoresis, isoelectric point electrophoresis, or the like, or a combination thereof. When the target enzyme is secreted and expressed, a culture supernatant containing the target enzyme can be obtained by removing bacterial cells from a culture solution obtained by culturing the transformed microorganism by centrifugation or the like. The target enzyme can also be purified and isolated from the culture supernatant.

The amino group-containing compound and the carboxyl group-containing compound which are substrates used in the method can be added to a reaction system containing the enzyme, such as e.g. an aqueous solution containing the enzyme, a culture solution containing a transformed microorganism that produces the enzyme, or a treated product of the transformed microorganism that produces the enzyme. Alternatively, in the method, an amino group-containing compound or a carboxyl group-containing compound produced in another reaction system can also be used as a substrate.

When the method is performed using the enzyme itself, such as e.g. purified enzyme, an aqueous solution containing the enzyme can be used as the reaction system. The aqueous solution can be a buffer. Examples of the buffer include a phosphate buffer, a Tris buffer, a carbonate buffer, an acetate buffer, and a citrate buffer. The aqueous solution has a pH of, for example, about 5 to 10. The amounts of the enzyme, and the amino group-containing compound and the carboxyl group-containing compound (substrates) in the reaction system, and reaction time can be appropriately adjusted depending on the amount of the N-acyl-amino group-containing compound to be produced. Reaction temperature is not particularly limited as long as the reaction proceeds, but can be 20 to 40° C.

The method may be performed in combination with an ATP regeneration system. When the method is performed using the enzyme itself, such as e.g. a purified enzyme, examples of the combination with the ATP regeneration system include a reaction by a combination with an ATP regeneration enzyme, such as by e.g. mixing. Examples of the ATP regeneration enzyme include polyphosphate kinase, a combination of polyphosphate: AMP phosphate transferase and polyphosphate kinase, and a combination of polyphosphate: AMP phosphate transferase and adenylate kinase. When the method is performed using a transformed microorganism that produces the enzyme or a treated product thereof, examples of the combination with the ATP regeneration system include use of a microorganism having enhanced ability to supply ATP as a host. Examples of the microorganism having enhanced ability to supply ATP include a microorganism that produces or enhances the above-described ATP regeneration enzyme. Examples of the microorganism that produces or enhances the ATP regeneration enzyme include a host into which an expression unit of the ATP regeneration enzyme is introduced by transformation, a host containing a mutation that enhances the amount of expression of the ATP regeneration enzyme in a host genome, and a host containing a mutation that enhances an activity of the ATP regeneration enzyme in the host genome.

Production of N-Acyl-Amino Group-Containing Compound by Microorganism Culture Method In the method, the reaction in the presence of the enzyme may be performed using a transformed microorganism, e.g. a cultured product of the microorganism, that produces the enzyme.

When the method is performed using a cultured product of the transformed microorganism, the transformed microorganism may be, for example, a host having enhanced ability to incorporate an amino acid and/or a fatty acid in order to improve supply efficiency of a substrate of an enzymatic reaction to improve production efficiency. Examples of the host having the enhanced incorporating ability include those described above. In this case, by culturing the transformed microorganism in a culture solution containing an amino group-containing compound, e.g. an amino acid, and/or a carboxyl group-containing compound, e.g. a fatty acid, both substrates are incorporated into the transformed microorganism, and an amide bond is formed by an enzyme produced in the transformed microorganism. As a result, a target N-acyl-amino group-containing compound, e.g. an N-acylamino acid, can be produced.

In addition, in order to suppress a loss of the substrate in the enzymatic reaction and/or to promote supply of the substrate in the enzymatic reaction or to suppress a loss of a product, the transformed microorganism may have, for example, at least one of the following genetic modifications:

(1) enhancement of ability to supply a fatty acid;
(2) enhancement of ability to supply an amino acid;
(3) enhancement of ability to supply ATP; and
(4) deficiency or attenuation of an N-acylamino acid degrading enzyme.

Such a transformed microorganism may have a genetic modification effective for enhancement of ability to supply a fatty acid, and such a transformed microorganism may be a transformed microorganism in which a fatty acid degradation system is attenuated or deficient and/or its synthesis system is enhanced. Examples of the transformed microorganisms (host) in which the degradation system is attenuated or deficient and/or the synthesis system is enhanced include those described above. Preferable examples of such a transformed microorganism include a microorganism which includes at least one genetic modification:

(a) deficiency or attenuation of acyl-CoA synthetase; and
(b) enhancement of acyl-ACP thioesterase.

Details of the genetic modifications of (a) and (b) are as described above.

When the N-acyl-amino group-containing compound is produced by culturing the transformed microorganism, culture conditions of the transformed microorganism are not particularly limited, and for example, culture conditions for performing culture in a medium further containing a predetermined amount of an amino group-containing compound and/or carboxyl group-containing compound under the culture conditions described above can be used.

Production of N-Acyl-Amino Group-Containing Compound by Direct Fermentation Method Described herein is a method for producing an N-acyl-amino group-containing compound by a direct fermentation method. The "direct fermentation method" refers to a method for producing an N-acyl-amino group-containing compound, e.g. an N-acylamino acid, by culturing a transformed microorganism in a culture solution containing a carbon source as a raw material to produce a target N-acyl-amino group-containing compound, e.g. an N-acylamino acid, from the carbon source. This method is based on a principle that a carbon source is incorporated into a microorganism, the carbon source is metabolized into a carboxyl group-containing compound, e.g. a fatty acid and an amino group-containing compound, e.g. an amino acid in the microorganism, and the carboxyl group-containing compound, e.g. a fatty acid and the amino group-containing compound, e.g. an amino acid produced by metabolism are bonded to each other by an amide bond due to an action of an enzyme having an N-acylation activity in the microorganism, thereby producing a target N-acyl-amino group-containing compound, e.g. an N-acylamino acid.

For example, the direct fermentation method can be expressed as a method for producing an N-acyl-amino group-containing compound in which an amino group-containing compound and a carboxyl group-containing compound are bonded to each other by an amide bond, the method including culturing, in the presence of a carbon source, a microorganism which includes at least one of the following genetic modifications:

(1) enhancement of ability to supply a fatty acid;
(2) enhancement of ability to supply an amino acid;
(3) enhancement of ability to supply ATP; and
(4) deficiency or attenuation of an N-acylamino acid degrading enzyme, and which includes an expression unit of a polynucleotide encoding an enzyme having an N-acylation activity. Details of the above (1) to (4) are similar to those described above (other portions are also similar).

The direct fermentation method can be expressed as a method for producing an N-acyl-amino group-containing compound in which an amino group-containing compound and a carboxyl group-containing compound are bonded to each other by an amide bond, the method including culturing, in the presence of a carbon source, a microorganism which includes at least one of the following genetic modifications:

(a) deficiency or attenuation of acyl-CoA synthetase; and
(b) enhancement of acyl-ACP thioesterase, and which includes an expression unit of a polynucleotide encoding an enzyme having an N-acylation activity. Details of the above (a) and (b) are similar to those described above (other portions are also similar).

Examples of the carbon source include a saccharide, a lipid, a protein, and an alcohol, e.g. glycerin, and a saccharide is preferable. Examples of the saccharide include glucose, galactose, mannose, fructose, sucrose, maltose, lactose, starch hydrolysate, and molasses, and glucose is a particular example.

Details of the genetic modifications of (a) and (b) are as described above. At least one genetic modification of (a) and (b) suppresses a loss of a substrate in the enzymatic reaction and/or promotes supply of the substrate in the enzymatic reaction, thereby enhancing the metabolism from the carbon source to the carboxyl group-containing compound, e.g. a fatty acid in the microorganism.

An amino group-containing compound, e.g. an amino acid, and a carboxyl group-containing compound, e.g. a fatty acid, produced by metabolism are bonded to each other by an amide bond due to an action of an enzyme having an N-acylation activity to produce an N-acyl-amino group-containing compound, e.g. an N-acylamino acid, as a target product.

The "enzyme having an N-acylation activity" refers to an enzyme having ability to bond a carboxyl group and an amino group to each other in an ATP-dependent manner to form an amide bond. As the enzyme having an N-acylation activity, the above-described modified enzyme having an N-acylation activity, such as the modified enzyme as described herein, may be used, and a protein found to have ability to bond a carboxyl group and an amino group to each other in an ATP-dependent manner to form an amide bond, a protein containing an amino acid sequence including substitution, deletion, insertion, or addition of one or several amino acids in an amino acid sequence of the protein and having an N-acylation activity, and a protein containing an amino acid sequence having 90% or more identity to an amino acid sequence of the protein and having an N-acylation activity may be used. Examples of the protein found to have ability to bond a carboxyl group and an amino group to each other in an ATP-dependent manner to form an amide bond include a GH3 protein, such as AtGH3-6, OsGH3-8, AtJAR1 (AtGH3-11), AtGH3-5, AtGH3-10, AtGH3-12, AtGH3-17, SsGH3, or CfHP (WP_002626336)) and a PaaK protein (PsIAAL or PaHP (WP_031591948)) described in PCT/JP2019/007681. AtGH3-6 (SEQ ID NO: 1) may be used. The GH3 protein and the PaaK protein also include mutants thereof, such as a protein containing an amino acid sequence containing substitution, deletion, insertion, or addition of one or several amino acids in an amino acid sequence of the protein and having an N-acylation activity, and a protein containing an amino acid sequence having 90% or more identity to an amino acid sequence of the protein and having an N-acylation activity.

Examples of the amino group-containing compound produced by metabolism include those described above as examples of the amino group-containing compound, but an amino acid is a particular example, and L-glutamic acid or L-aspartic acid is further examples. Examples of the carboxyl group-containing compound produced by metabolism include those described above as examples of the carboxyl group-containing compound, but a fatty acid, such as e.g. a saturated fatty acid, a fatty acid having 8 to 18 carbon atoms, e.g. a saturated fatty acid, a fatty acid having 12 carbon atoms, and lauric acid.

When the N-acyl-amino group-containing compound is produced by culturing the transformed microorganism, culture conditions of the transformed microorganism are not particularly limited, and for example, culture conditions for performing culture in a medium further containing a predetermined amount of a carbon source, e.g. a saccharide such as glucose, can be used.

Production of the N-acyl-amino group-containing compound can be appropriately confirmed. For example, such confirmation can be performed by adding a reaction stop solution, e.g. an aqueous solution of 1.4% (w/v, phosphoric acid and 75% (v/v, methanol, to the reaction system and subjecting the supernatant after centrifugation to UPLC-MS analysis.

Surfactant

The N-acyl-amino group-containing compound, e.g. an N-acyl-amino group-containing compound produced by the method, or a salt thereof may be used for various applications, and for example, may be used as a component contained in a composition such as a cosmetic material, e.g. a surfactant. The N-acyl-amino group-containing compound or a salt thereof contained in such a composition may contain, for example, an N-monounsaturated acyl-amino group-containing compound or a salt thereof. Examples of the N-monounsaturated acyl-amino group-containing compound or a salt thereof include those described above.

When the N-acyl-amino group-containing compound or a salt thereof is used as a component of a surfactant, the surfactant may include an N-monounsaturated acyl-amino group-containing compound having a monounsaturated acyl group having 10 to 16 carbon atoms or a salt thereof. In such a case, since an acyl moiety of the N-monounsaturated acyl-amino group-containing compound is a monounsaturated acyl, an effect that the N-monounsaturated acyl-amino group-containing compound suppresses an increase in viscosity, has a low viscosity with high handleability, and has good solubility is exhibited. In addition, since the acyl moiety has 10 to 16 carbon atoms, good foaming and foam quality are obtained.

Examples of the salt of the N-acyl-amino group-containing compound include those described above.

When the N-acyl-amino group-containing compound is obtained from a monounsaturated fatty acid, the N-acyl-amino group-containing compound may be that obtained, for example, by reacting a monounsaturated fatty acid derivative represented by $C_{n-1}H_m$—COX, wherein X represents any monovalent group, for example, a halogen atom selected from the group consisting of fluorine, chlorine, bromine, and iodine, with an acidic amino acid salt. Examples of the salt include inorganic salts and organic salts as described above.

Examples of the monounsaturated fatty acid from which the N-monounsaturated acyl-amino group-containing compound is derived include decenoic acid (C10: 1), dodecenoic acid (C12: 1), tetradecenoic acid (C14: 1), e.g. myristoleic acid, and hexadecenoic acid (C16: 1, e.g. palmitoleic acid.

The "acidic amino acid" in the "N-acyl-amino group-containing compound" refers to an amino acid having an acidic side chain. Examples of the acidic amino acid include glutamic acid and aspartic acid.

Examples of the N-monounsaturated acyl-amino group-containing compound include N-decenoyl acidic amino acid (C10: 1), N-dodecenoyl acidic amino acid (C12: 1), N-tetradecenoyl acidic amino acid (C14: 1), and N-hexadecenoyl acidic amino acid (C16: 1).

The N-monounsaturated acyl-amino group-containing compound may include one kind of N-monounsaturated acyl-amino group-containing compound, or two or more kinds of N-monounsaturated acyl-amino group-containing compound. That is, the N-monounsaturated acyl-amino group-containing compound may include one or more of N-decenoyl acidic amino acid (C10: 1), N-dodecenoyl acidic amino acid (C12: 1), N-tetradecenoyl acidic amino acid (C14: 1), and N-hexadecenoyl acidic amino acid (C16: 1). When two or more kinds of N-monounsaturated acyl-amino group-containing compound are used, a combination of N-dodecenoyl acidic amino acid (C12: 1) and one or more of N-decenoyl acidic amino acid (C10: 1), N-tetradecenoyl acidic amino acid (C14: 1), and N-hexadecenoyl acidic amino acid (C16: 1) is preferable, and a combination of N-dodecenoyl acidic amino acid (C12: 1) and N-hexadecenoyl acidic amino acid (C16: 1) is more preferable from the viewpoint of improving foam quality.

A unsaturated bond site of the N-monounsaturated acyl acidic amino acid is not particularly limited, and the unsaturated bond may be present at a carbon chain terminal of an acyl moiety, between carbon atoms separated by several carbon atoms from the carbon chain terminal of the acyl moiety, or at an «-position of a carbonyl group of the acyl moiety. In particular, the unsaturated bond can be present between carbon atoms separated by 6 or 7 carbon atoms from the carbon chain terminal of the acyl moiety. That is, the N-monounsaturated acyl acidic amino acid is a compound represented by the following general formula (A).

(A)

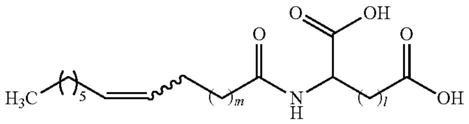

In general formula (A), "1" is an integer of 1 or 2, and "m" is an integer of 0 to 6.

The stereochemistry (unsaturated double bond site) of the N-monounsaturated acyl acidic amino acid may be either in a cis or trans conformation. However, a cis conformation is preferable from a viewpoint of suppressing an increase in viscosity and achieving a low viscosity with high handleability.

Composition

The composition includes component (A) an N-monounsaturated acyl acidic amino acid or a salt thereof, wherein the unsaturated acyl is an acyl having 10 to 16 carbon atoms, and component (B) an N-saturated acyl acidic amino acid or a salt thereof.

The composition includes component (A), and therefore has good foaming action, foam quality, and solubility even when weakly acidic having a pH equivalent to that of the skin, and has a low viscosity with high handleability. In addition, the composition is a composition also including component (B) and having variations in an acyl group, and therefore has an effect of improving oil cleansing power.

Component (A)

Details of component (A) are as described in the N-monounsaturated acyl acidic amino acid of the surfactant.

Component (B)

The "N-saturated acyl acidic amino acid" refers to a compound represented by $C_{n-1}H_m$—CO—NH—CHR—COOH, in which the hydrogen atom represented by $H_m$ may be replaced, m is as defined above, and R represents a side chain of an acidic amino acid, as a free form. That is, the "N-saturated acyl acidic amino acid" refers to a compound in which one hydrogen atom on an amino group of an acidic amino acid is replaced with a saturated acyl group. The "N-saturated acyl acidic amino acid" may be a free form of an N-saturated acyl acidic amino acid or a salt of the N-saturated acyl acidic amino acid.

Note that the same as the salt of the N-monounsaturated acyl acidic amino acid applies to the salt of the N-saturated acyl acidic amino acid.

The N-saturated acyl acidic amino acid may be derived from a fatty acid represented by $C_{n-1}H_m$—COOH or a derivative thereof for convenience. In addition, a "saturated acyl having n carbon atoms" and a fatty acid and the like from which the saturated acyl having n carbon atoms is derived may be represented by "Cn". For example, "N-lauroyl acidic amino acid (C12," refers to a compound in which one hydrogen atom on an amino group of an acidic amino acid is replaced with a lauroyl group which is an acyl group derived from lauric acid (C12), $C_{11}H_{23}$CO—NH—CHR—COOH in which R represents a side chain of the acidic amino acid.

When the N-saturated acyl acidic amino acid is obtained from a saturated fatty acid, the N-saturated acyl acidic amino acid can be obtained, for example, by reacting a saturated fatty acid derivative represented by $C_{n-1}H_m$—COX, wherein X represents any monovalent group, for example, a halogen atom of fluorine, chlorine, bromine, and iodine, with an acidic amino acid or a salt thereof. Examples of the salt include inorganic salts and organic salts as described above.

Examples of the N-saturated acyl acidic amino acid include N-capryloyl acidic amino acid (C8), N-caproyl acidic amino acid (C10), N-lauroyl acidic amino acid (C12), N-myristoyl acidic amino acid (C14), N-palmitoyl acidic amino acid (C16), and N-stearoyl acidic amino acid (C18).

The "acidic amino acid" in the "N-saturated acyl acidic amino acid" refers to an amino acid having an acidic side chain. Examples of the acidic amino acid include glutamic acid and aspartic acid.

As the N-saturated acyl acidic amino acid, N-capryloyl acidic amino acid (C8), N-caproyl acidic amino acid (C10), N-lauroyl acidic amino acid (C12), N-myristoyl acidic amino acid (C14), or N-palmitoyl acidic amino acid (C16) is examples.

Component (B) may include one kind of N-saturated acyl acidic amino acid or a salt thereof, or two or more kinds of N-saturated acyl acidic amino acids or salts thereof. That is, component (B) may include one or more of N-capryloyl acidic amino acid (C8), N-caproyl acidic amino acid (C10), N-lauroyl acidic amino acid (C12), N-myristoyl acidic amino acid (C14), N-palmitoyl acidic amino acid (C16), and N-stearoyl acidic amino acid (C18). When component (B) includes two or more kinds of N-saturated acyl acidic amino acids, component (B) can include N-lauroyl acidic amino acid (C12), or includes N-lauroyl acidic amino acid (C12) and one or more of N-capryloyl acidic amino acid (C8), N-caproyl acidic amino acid (C10), N-myristoyl acidic amino acid (C14), and N-palmitoyl acidic amino acid (C16) in combination.

When component (B) includes N-lauroyl acidic amino acid (C12), the content of N-lauroyl acidic amino acid (C12) in component (B) is, for example, 30% by mass or more, 40% by mass or more, 50% by mass or more, or 60% by mass or more. More specifically, the content of N-lauroyl acidic amino acid in component (B) is, for example, 30 to 100% by mass, 40 to 100% by mass, 50 to 100% by mass, or 60 to 100% by mass.

A mass ratio of component (A) to the total of component (A) and component (B) (A/(A+B)) is usually 0.001 or more, 0.002 or more, 0.003 or more, or 0.004 or more from the viewpoint of improving solubility at a low pH by component (A), and the like. The mass ratio of component (A) to the total of component (A) and component (B) (A/(A+B)) is usually 1.00 or less, less than 1.00, 0.80 or less, 0.60 or less, or 0.50 or less from the viewpoint of contribution to oil cleansing power due to a large content of component (B), and the like. More specifically, the mass ratio of component (A) to the total of component (A) and component (B) (A/(A+B)) is usually 0.001 to 1.00, 0.001 or more and less than 1.00, 0.002 to 0.80, 0.003 to 0.60, or 0.004 to 0.50.

The composition may further include component (C) an N-unsaturated fatty acid or a salt thereof.

When the composition includes component (C), the foam quality is better, and the oil cleansing power is further improved.

Component (C)

The number of carbon atoms of the unsaturated fatty acid can be 6 to 22, or 8 to 18. Examples of the unsaturated fatty acid include hexenoic acid (C6: 1), octenoic acid (C8: 1), decenoic acid (C10: 1), dodecenoic acid (C12: 1), tetradecenoic acid (C14: 1), e.g. myristoleic acid, hexadecenoic acid (C16: 1), e.g. palmitoleic acid), octadecenoic acid (C18: 1), e.g. oleic acid, icosenoic acid (C20: 1), e.g. eicosenoic acid, and docosenoic acid (C22: 1).

Examples of the salt of the unsaturated fatty acid include an inorganic salt such as a sodium salt, a potassium salt, a calcium salt, a magnesium salt, or an aluminum salt; an organic amine salt such as an ammonium salt, a monoethanolamine salt, a diethanolamine salt, or a triethanolamine salt; and an organic salt such as a basic amino acid salt including an arginine salt and a lysine salt. Among these salts, a triethanolamine salt, a sodium salt, and a potassium salt are particular examples.

Component (C) may include one kind of unsaturated fatty acid or a salt thereof, or two or more kinds of unsaturated fatty acids or salts thereof. That is, component (C) may include one or more of hexenoic acid (C6: 1), octenoic acid (C8: 1), decenoic acid (C10: 1), dodecenoic acid (C12: 1), tetradecenoic acid (C14: 1), e.g. myristoleic acid, hexadecenoic acid (C16: 1), e.g. palmitoleic acid, octadecenoic acid (C18: 1), e.g. oleic acid, icosenoic acid (C20: 1), e.g. eicosenoic acid, and docosenoic acid (C22: 1). When component (C) includes two or more kinds of unsaturated fatty acids or salts thereof, component (C) includes dodecenoic acid (C12: 1), and can include dodecenoic acid (C12: 1) and one or more of octenoic acid (C8: 1), decenoic acid (C10: 1), tetradecenoic acid (C14: 1), and hexadecenoic acid (C16: 1) in combination.

When component (C) includes dodecenoic acid (C12: 1), the amount of dodecenoic acid (C12: 1) in component (C) is, for example, 30% by mass or more, 40% by mass or more, 50% by mass or more, 60% by mass or more, 70% by mass or more, or 80% by mass or more. More specifically, the amount of dodecenoic acid (C12: 1) in component (C) is, for example, 30 to 100% by mass, 40 to 100% by mass, 50 to 100% by mass, 60 to 100% by mass, 70 to 100% by mass, or 80 to 100% by mass.

A mass ratio of component (C) to the total of component (A) and component (B) (C/(A+B)) may be 0 or more. When the mass ratio of component (C) to the total of component (A) and component (B) (C/(A+B)) is 0, component (C) is not present. The mass ratio can be 0.01 or more, and can be 0.1 or more, 0.2 or more, 0.4 or more, or 0.5 or more from the viewpoint of contribution of component (C) to improvement of foam quality (density), and the like. The mass ratio of component (C) to the total of component (A) and component (B) (C/(A+B)) is usually 20 or less, 15 or less, 13 or less, 11 or less, or 10 or less from the viewpoint of contribution of an effect of component (A) and component (B), and the like. More specifically, the mass ratio of component (C) to the total of component (A) and component (B) (C/(A+B)) is usually 0.01 to 20, 0.1 to 15, 0.4 to 11, or 0.5 to 10.

The composition may include component (A), component (B), and an optional component (C) in (D) a water-soluble medium. As the water-soluble medium, any water-soluble solvent can be used. Examples of the water-soluble medium include an aqueous solution. The aqueous solution may have buffering ability or does not have to have buffering ability. Examples of the aqueous solution include water, e.g. distilled water, sterilized distilled water, purified water, physiological saline, or tap water such as city water, a phosphoric acid buffer, a Tris-hydrochloric acid buffer, a TE (Tris-EDTA, buffer, a carbonic acid buffer, a boric acid buffer, a tartaric acid buffer, a glycine buffer, a citric acid buffer, and an acetic acid buffer.

The amount of component (A) varies depending on various conditions such as the kinds and concentrations of other components included in the composition and a pH, and therefore is not particularly limited. When the composition is in a form of an aqueous solution, the amount of component (A) is, for example, 0.001% by mass or more, 0.002% by mass or more, and 0.003% by mass or more from the viewpoint of improving solubility at a low pH, and the like. The amount of component (A) can be, for example, 60% by mass or less, and can be 40% by mass or less. More specifically, the amount of component (A) is, for example, 0.001 to 60% by mass, 0.001 to 40% by mass, 0.002 to 40% by mass, and 0.003 to 40% by mass.

The content of component (B) varies depending on various conditions such as the kinds and concentrations of other components included in the composition and the pH, and therefore is not particularly limited. When the composition is in a form of an aqueous solution, the content of component (B) is, for example, 0.01% by mass or more, 0.02% by mass or more, and 0.03% by mass or more from a viewpoint of improving solubility at a low pH, and the like. The amount of component (B) can be, for example, 60% by mass or less, 40% by mass or less, or 10% by mass or less. More specifically, the amount of component (B) is, for example, 0.01 to 60% by mass, 0.02 to 40% by mass, or 0.03 to 10% by mass.

The amount of component (C) varies depending on various conditions such as the kinds and concentrations of other components included in the composition and the pH, and therefore is not particularly limited, but may be 0% by mass or more. When the amount of component (C) is 0% by mass, component (C) is not present. When the composition is in a form of an aqueous solution, the amount of component (C) is, for example, 0.001% by mass or more, 0.002% by mass or more, and 0.003% by mass or more from the viewpoint of contribution to improvement of foam quality (density), and the like. The content of component (C) can be, for example, 5% by mass or less, 3% by mass or less, or 1% by mass or less from the viewpoint of inhibiting the effect when the component (C) is included in a large amount, and the like. More specifically, the amount of component (C) is, for example, 0.001 to 5% by mass, 0.002 to 3% by mass, or 0.003 to 1% by mass.

The composition is weakly acidic from the viewpoint of storage stability due to suppression of growth of various bacteria (antiseptic effect) and low irritation to the skin due to a pH equivalent to that of the skin (weakly acidic). The pH of the composition is, for example, 3.0 to 9.0 and can be 3.0 to 8.0 or 3.0 to 7.0. An upper limit of the pH is 8.0 or less, or 7.0 or less. In addition, a lower limit is 4.0 or more, or 4.5 or more. The pH of the composition is 4.0 to 8.0, 4.0 to 7.0, 4.5 to 8.0, or 4.5 to 7.0 from the viewpoint of achieving a pH equivalent to that of the skin. The composition has excellent solubility even at a low pH, and therefore suppresses precipitation. It can be said that the composition has excellent storage stability also in this respect. Furthermore, in general, when the pH of an anionic surfactant decreases, foaming tends to decrease. However, the composition has good foaming even at a low pH. The pH can be adjusted using a pH adjusting agent. Examples of the pH adjusting agent include an aqueous solution (buffer) as described above, an acidic substance, e.g. hydrochloric acid, sulfuric acid, nitric acid, or citric acid, and an alkaline substance, e.g. a hydroxide of an alkali metal including sodium and potassium or an alkaline earth metal including calcium.

The composition has a low viscosity from a viewpoint of handleability. The viscosity of the composition is, for example, 1.5 Pas or less, 1.0 Pa's or less, 0.80 Pa's or less, 0.70 Pa's or less, or 0.50 Pa's or less. The composition has excellent handleability, and therefore can be said to be useful as a cosmetic as a personal care.

The viscosity is a value obtained by measuring an aqueous solution of a composition having a concentration of 10% by mass with a B-type viscometer (DVB-10: B-type viscometer manufactured by Toyo Seiki Seisaku-sho, Ltd., rotor Nos. 20 to 23, 6 to 30 rpm, 25° C., after 30 seconds).

The composition may also include another component such as an additional cleansing component, a polyhydric alcohol, a thickener, a stabilizer, a preservative, a fragrance, or a pigment. Specific kinds and amounts of these components can be appropriately set.

Examples of the additional cleansing component include a surfactant such as an anionic surfactant, an amphoteric surfactant, or a nonionic surfactant, and a microsolid, e.g. a microsphere or a scrub.

The anionic surfactant includes one or more anionic groups. Examples of the anionic group include a carboxyl group, a sulfonic acid group, a sulfuric acid group, and a phosphoric acid group. Examples of the anionic surfactant include a higher fatty acid, an N-acylamino acid, an N-acyltaurine, an alkyl ether carboxylic acid, an alkyl phosphoric acid, a polyoxyethylene alkyl ether phosphoric acid, an alkyl sulfuric acid, a polyoxyethylene alkyl ether sulfuric acid, a sulfonic acid compound having an alkyl chain, and salts thereof.

The amphoteric surfactant includes one or more anionic groups as described above and one or more cationic groups. Examples of the cationic group include an ammonium group, a primary amino group, a secondary amino group, a tertiary amino group, and a quaternary amino group. Examples of the amphoteric surfactant include an amide betaine amphoteric surfactant, a betaine acetate amphoteric surfactant, a sulfobetaine amphoteric surfactant, and an imidazoline amphoteric surfactant, e.g. lauroamphoacetic acid or a salt thereof.

Examples of the nonionic surfactant include an ester type surfactant such as a glycerin fatty acid ester, a sorbitan fatty acid ester, or a sucrose fatty acid ester, an ether type surfactant such as an alkyl polyethylene glycol or a polyoxyethylene alkyl phenyl ether, and a nonionic surfactant such as an alkyl glycoside in which a saccharide and a higher alcohol are bonded to each other by a glycosidic bond or an alkyl polyglycoside.

Examples of the polyhydric alcohol include a dihydric alcohol, e.g. ethylene glycol, propylene glycol, 1,3-propanediol, 1,2-butylene glycol, 1,3-butylene glycol, 2,3-butylene glycol, 1,4-butanediol, 2-butene-1,4-diol, 1,5-pentanediol, 1,2-pentanediol, isoprene glycol, hexylene glycol, diethylene glycol, dipropylene glycol, or monoglyceride such as monoacylglycerol, a trihydric alcohol, e.g. glycerin, trimethylolpropane, or 1,2,6-hexanetriol, a tetrahydric alcohol, e.g. diglycerin or pentaerythritol, an alcohol having a higher valence, and salts thereof, e.g. inorganic salts and organic salts as described above. Examples of the alcohol having a higher valence include a sugar alcohol optionally having a substituent. e.g. a monosaccharide alcohol such as sorbitol, mannitol, sucrose, glucose, or mannose, a disaccharide alcohol such as trehalose, and a polysaccharide alcohol such as hyaluronic acid or xanthan gum, a polymer of a dihydric to tetrahydric alcohol as described above, e.g. polyglycol or polyglycerin, and salts thereof, e.g. inorganic salts and organic salts as described above. The polyhydric alcohol is a dihydric to tetrahydric alcohol, or a dihydric or trihydric alcohol.

Examples of the thickener include carrageenan, dextrin, methyl cellulose, ethyl cellulose, hydroxyethyl cellulose, hydroxypropyl cellulose, hydroxypropyl methyl cellulose, polyacrylic acid, polymethacrylic acid, carboxyvinyl polymer such as carbomer, acrylic acid/alkyl acrylate (C10-30, copolymer, and xanthan gum.

Examples of the stabilizer include ascorbic acid, sodium pyrosulfite, and EDTA.

Examples of the preservative include ethyl parahydroxybenzoate, sodium benzoate, salicylic acid, sorbic acid, paraben, such as methylparaben, propylparaben, or the like, and sodium bisulfite.

Examples of the fragrance include a natural fragrance and a synthetic fragrance. Examples of the natural fragrance include rose oil, jasmine oil, neroli oil, lavender oil, ylang-ylang oil, tubellows oil, clary sage oil, clove oil, peppermint oil, geranium oil, patulie oil, sandalwood oil, cinnamon oil, coriander oil, nutmeg oil, pepper oil, lemon oil, orange oil, bergamot oil, opoponax oil, vetiver oil, oris oil, and oak moss oil. Examples of the synthetic fragrance include limonene (orange), β-caryophyllene (woody), cis-3-hexenol (young green leaves), linalool (lily of the valley), farnesol (floral with fresh green notes), β-phenylethyl alcohol (rose), 2,6-nonadienal (violet or cucumber), citral (lemon), α-hexyl cinnamic aldehyde (jasmine), β-ionone (violet when being diluted), t-carboxylic (spearmint), cyclopentadecanone (musk), linalyl acetate (bergamot or lavender), benzyl benzoate (balsam), γ-undecalactone (peach), eugenol (clove), rose oxide (green floral), indole (jasmine when being diluted), phenylacetaldehyde dimethyl acetal (hyacinth), auranthiol (orange flower), and menthol (peppermint). The word in the parentheses indicates an aroma.

Examples of the pigment include an organic pigment, e.g. a red pigment such as Red No. 201, a blue pigment such as Blue No. 404, an orange pigment such as Orange No. 203, a yellow pigment such as Yellow No. 205, a green pigment such as Green No. 3, an organic lake pigments such as zirconium lake, or a natural pigment such as chlorophyll, and an inorganic pigment, e.g. a white pigment such as titanium oxide, a colored pigment such as iron oxide, an extender pigment such as talc, or a pearl pigment such as mica.

The composition can be provided in various forms such as powder, liquid, gel, paste, cream, and foam. Note that the composition can be produced by a usual method.

The composition can be a cosmetic in any form applicable to, for example, the skin, hair, or scalp according to a usual method. The cosmetic is suitable for applications such as a body shampoo, a hand soap, a facial cleanser, a cleansing lotion, a cleansing cream, a massage cream, and a hair shampoo as a cleanser for animals such as humans. Properties of the cosmetic, e.g. pH, is similar to that of the composition described above.

In addition, the composition can also be used as an additive such as an excipient.

EXAMPLES

The present invention will be described in more detail by describing the following Examples, but the present invention is not limited to the following Examples.

Example 1: Construction of Mutant AtGH3-6 Expression Plasmid by Site-Directed Mutagenesis (1) A mutation was introduced into AtGH3-6 using, as a template, pET-28a-AtGH3-6 (PCT/JP2019/007681) that expresses *Arabidopsis thaliana*-derived indole-3-acetic acid-amido synthetase GH3.6 (AtGH3-6, Q9LSQ4, SEQ ID NO: 1 for an amino acid sequence, SEQ ID NO: 2 for a nucleotide sequence encoding the amino acid sequence in which a codon is optimized for expression in *E. coli*) in which a His-tag and a thrombin recognition sequence were fused to an N-terminal side. In addition, into some samples of mutant AtGH3-6, a mutation was further introduced using, as a template, a mutant AtGH3-6 expression plasmid obtained below. A method for constructing an expression plasmid of mutant AtGH3-6 (Mutant No. 31) is described in Example 1 (2). Mutagenesis was performed using PrimeSTAR Max DNA Polymerase (Takara Bio Inc.) under the following conditions.

1 cycle 98° C., 30 sec
30 cycles 98° C., 10 sec
55° C., 15 sec
72° C., 40 sec
1 cycle 72° C., 5 min
4° C., hold Primers used are as follows. WT in Table indicates wild type AtGH3-6.

TABLE 2-1

Primer for site-directed mutagenesis used in preparation of mutant AtGH3-6 (1)

| Mutant No. | Template | Introduced mutation point | Nucleotide sequence (5' to 3') | SEQ ID NO |
|---|---|---|---|---|
| R18 | WT | Y134F | CGTCGGAGTCTGCTGTTTTCACTCCTTAT GCCC | 7 |
| | | | GGGCATAAGGAGTGAAAACAGCAGACT CCGACG | 8 |
| R20 | WT | Y134V | CGTCGGAGTCTGCTGGTGTCACTCCTTAT GCCC | 9 |
| | | | GGGCATAAGGAGTGACACCAGCAGACT CCGACG | 10 |
| R30 | WT | S161P | TTCCTCTTCATCAAGCCGGAATCGAAAA CCCCT | 11 |
| | | | AGGGGTTTTCGATTCCGGCTTGATGAAG AGGAA | 12 |
| R32 | WT | V174A | CTGCCTGCACGTCCCGCGCTGACCTCGT ATTAC | 13 |
| | | | GTAATACGAGGTCAGCGCGGGACGTGCA GGCAG | 14 |
| R39 | WT | V231A | CTGCGTGTTGGCGCGGCGTTTGCCAGCG GGTTT | 15 |
| | | | AAACCCGCTGGCAAACGCCGCGCCAACA CGCAG | 16 |
| R55 | WT | T336S | TTACCGTTAGTCTGCAGCATGTATGCGA GCAGT | 17 |
| | | | ACTGCTCGCATACATGCTGCAGACTAAC GGTAA | 18 |
| R56 | WT | M337G | CCGTTAGTCTGCACGGGCTATGCGAGCA GTGAA | 19 |
| | | | TTCACTGCTCGCATAGCCCGTGCAGACT AACGG | 20 |
| R59 | WT | A339G | GTCTGCACGATGTATGGCAGCAGTGAAT GCTAC | 21 |
| | | | GTAGCATTCACTGCTGCCATACATCGTG CAGAC | 22 |
| R61 | WT | S340A | TGCACGATGTATGCGGCGAGTGAATGCT ACTTT | 23 |
| | | | AAAGTAGCATTCACTCGCCGCATACATC GTGCA | 24 |
| R68 | WT | Y344G | GCGAGCAGTGAATGCGGCTTTGGAGTGA ATCTC | 25 |
| | | | GAGATTCACTCCAAAGCCGCATTCACTG CTCGC | 26 |
| R69 | WT | Y344A | GCGAGCAGTGAATGCGCGTTTGGAGTGA ATCTC | 27 |
| | | | GAGATTCACTCCAAACGCGCATTCACTG CTCGC | 28 |

TABLE 2-1-continued

Primer for site-directed mutagenesis used in preparation of mutant AtGH3-6 (1)

| Mutant No. | Template | Introduced mutation point | Nucleotide sequence (5' to 3') | SEQ ID NO |
|---|---|---|---|---|
| R70 | WT | Y344V | GCGAGCAGTGAATGCGTGTTTGGAGTGA ATCTC | 29 |
| | | | GAGATTCACTCCAAACACGCATTCACTG CTCGC | 30 |
| R78 | WT | S455T | GTTCTCTCCATTGACACCGACAAGACGG ATGAA | 31 |
| | | | TTCATCCGTCTTGTCGGTGTCAATGGAG AGAAC | 32 |
| R1002 | WT | T122S/ I123T | CGCAAACTTATGCCGAGCACCGAGGAAG AACTGGAT | 33 |
| | | | ATCCAGTTCTTCCTCGGTGCTCGGCATAA GTTTGCG | 34 |
| R1005 | WT | R117P | ACCTCAGGCGGAGAACCGAAACTTATGC CGACG | 35 |
| | | | CGTCGGCATAAGTTTCGGTTCTCCGCCTG AGGT | 36 |
| | R117P | Q533R | AATAGCGTGTATCGCCGTGGCCGTGTGT CCGAC | 37 |
| | | | GTCGGACACACGGCCACGGCGATACACG CTATT | 38 |

TABLE 2-2

Primer for site-directed mutagenesis used in preparation of mutant AtGH3-6 (2)

| Mutant No. | Template | Introduced mutation point | Nucleotide sequence (5' to 3') | SEQ ID NO |
|---|---|---|---|---|
| 4 | WT | C576A | TACAAAACACCAAGAGCGGTCAAATTCG CGCCG | 39 |
| | | | CGGCGCGAATTTGACCGCTCTTGGTGTTT TGTA | 40 |
| 7 | R32 | S161P | TTCCTCTTCATCAAGCCGGAATCGAAAA CCCCT | 41 |
| | | | AGGGGTTTTCGATTCCGGCTTGATGAAG AGGAA | 42 |
| 8 | R39 | S161P | TTCCTCTTCATCAAGCCGGAATCGAAAA CCCCT | 43 |
| | | | AGGGGTTTTCGATTCCGGCTTGATGAAG AGGAA | 44 |
| 9 | R56 | S161P | TTCCTCTTCATCAAGCCGGAATCGAAAA CCCCT | 45 |
| | | | AGGGGTTTTCGATTCCGGCTTGATGAAG AGGAA | 46 |
| 10 | R70 | S161P | TTCCTCTTCATCAAGCCGGAATCGAAAA CCCCT | 47 |
| | | | AGGGGTTTTCGATTCCGGCTTGATGAAG AGGAA | 48 |
| 11 | R39 | V174A | CTGCCTGCACGTCCCGCGCTGACCTCGT ATTAC | 49 |
| | | | GTAATACGAGGTCAGCGCGGGACGTGCA GGCAG | 50 |
| 12 | R32 | M337G | CCGTTAGTCTGCACGGGCTATGCGAGCA GTGAA | 51 |
| | | | TTCACTGCTCGCATAGCCCGTGCAGACT AACGG | 52 |

TABLE 2-2-continued

Primer for site-directed mutagenesis used in preparation of mutant AtGH3-6 (2)

| Mutant No. | Template | Introduced mutation point | Nucleotide sequence (5' to 3') | SEQ ID NO |
|---|---|---|---|---|
| 13 | R32 | Y344V | GCGAGCAGTGAATGCGTGTTTGGAGTGA ATCTC | 53 |
| | | | GAGATTCACTCCAAACACGCATTCACTG CTCGC | 54 |
| 14 | R39 | M337G | CCGTTAGTCTGCACGGGCTATGCGAGCA GTGAA | 55 |
| | | | TTCACTGCTCGCATAGCCCGTGCAGACT AACGG | 56 |
| 15 | R39 | Y344V | GCGAGCAGTGAATGCGTGTTTGGAGTGA ATCTC | 57 |
| | | | GAGATTCACTCCAAACACGCATTCACTG CTCGC | 58 |
| 16 | R56 | Y344V | GCGAGCAGTGAATGCGTGTTTGGAGTGA ATCTC | 59 |
| | | | GAGATTCACTCCAAACACGCATTCACTG CTCGC | 60 |
| 17 | R1005 | S161P | TTCCTCTTCATCAAGCCGGAATCGAAAA CCCCT | 61 |
| | | | AGGGGTTTTCGATTCCGGCTTGATGAAG AGGAA | 62 |
| 18 | R1005 | V174A | CTGCCTGCACGTCCCGCGCTGACCTCGT ATTAC | 63 |
| | | | GTAATACGAGGTCAGCGCGGGACGTGCA GGCAG | 64 |
| 19 | R1005 | V231A | CTGCGTGTTGGCGCGGCGTTTGCCAGCG GGTTT | 65 |
| | | | AAACCCGCTGGCAAACGCCGCGCCAACA CGCAG | 66 |
| 20 | R1005 | M337G | CCGTTAGTCTGCACGGGCTATGCGAGCA GTGAA | 67 |
| | | | TTCACTGCTCGCATAGCCCGTGCAGACT AACGG | 68 |
| 21 | R1005 | Y344V | GCGAGCAGTGAATGCGTGTTTGGAGTGA ATCTC | 69 |
| | | | GAGATTCACTCCAAACACGCATTCACTG CTCGC | 70 |
| 24 | WT | Y344I | GAATGCATTTTTGGAGTGAATCTCAGG | 71 |
| | | | TCCAAAAATGCATTCACTGCTCGCATA | 72 |

TABLE 2-3

Primer for site-directed mutagenesis used in preparation of mutant AtGH3-6 (3)

| Mutant No. | Template | Introduced mutation point | Nucleotide sequence (5' to 3') | SEQ ID NO |
|---|---|---|---|---|
| 30 | 18 | V231A | CTGCGTGTTGGCGCGGCGTTTGCCAGCG GGTTT | 73 |
| | | | AAACCCGCTGGCAAACGCCGCGCCAACA CGCAG | 74 |
| 32 | 18 | Y344V | GCGAGCAGTGAATGCGTGTTTGGAGTGA ATCTC | 75 |
| | | | GAGATTCACTCCAAACACGCATTCACTG CTCGC | 76 |

TABLE 2-3-continued

Primer for site-directed mutagenesis used in preparation of mutant AtGH3-6 (3)

| Mutant No. | Template | Introduced mutation point | Nucleotide sequence (5' to 3') | SEQ ID NO |
|---|---|---|---|---|
| 34 | 19 | Y344V | GCGAGCAGTGAATGCGTGTTTGGAGTGA ATCTC | 77 |
| | | | GAGATTCACTCCAAACACGCATTCACTG CTCGC | 78 |
| 37 | 31 | G379D | GTCCATCGTAACTCAGACGTAACTAGCA GCATT | 79 |
| | | | AATGCTGCTAGTTACGTCTGAGTTACGA TGGAC | 80 |
| | 31 + G379D | R350T | TTTGGAGTGAATCTCACGCCACTATGCA AACCA | 81 |
| | | | TGGTTTGCATAGTGGCGTGAGATTCACT CCAAA | 82 |
| 38 | 31 | V311A | ACCAAATATGTTGACGCGATTGTCACTG GCACC | 83 |
| | | | GGTGCCAGTGACAATCGCGTCAACATAT TTGGT | 84 |
| 39 | 31 | L137I | CTGCTGTACTCACTCATTATGCCCGTCAT GGAT | 85 |
| | | | ATCCATGACGGGCATAATGAGTGAGTAC AGCAG | 86 |
| 40 | 31 | Q200E | TATACCAGTCCGAATGAGACGATCTTGT GTTCC | 87 |
| | | | GGAACACAAGATCGTCTCATTCGGACTG GTATA | 88 |
| 42 | 31 | I123T | AAACTTATGCCGACGACCGAGGAAGAA CTGGAT | 89 |
| | | | ATCCAGTTCTTCCTCGGTCGTCGGCATAA GTTT | 90 |
| 43 | 31 | N101S | CAGGTTCTGTGTTCGAGCCCGATAAGCG AGTTT | 91 |
| | | | AAACTCGCTTATCGGGCTCGAACACAGA ACCTG | 92 |
| 44 | 40 | I123T | AAACTTATGCCGACGACCGAGGAAGAA CTGGAT | 93 |
| | | | ATCCAGTTCTTCCTCGGTCGTCGGCATAA GTTT | 94 |
| 45 | 40 | N101S | CAGGTTCTGTGTTCGAGCCCGATAAGCG AGTTT | 95 |
| | | | AAACTCGCTTATCGGGCTCGAACACAGA ACCTG | 96 |
| 46 | 42 | N101S | CAGGTTCTGTGTTCGAGCCCGATAAGCG AGTTT | 97 |
| | | | AAACTCGCTTATCGGGCTCGAACACAGA ACCTG | 98 |
| 48 | 37 | Q200E | TATACCAGTCCGAATGAGACGATCTTGT GTTCC | 99 |
| | | | GGAACACAAGATCGTCTCATTCGGACTG GTATA | 100 |
| 49 | 37 | I123T | AAACTTATGCCGACGACCGAGGAAGAA CTGGAT | 101 |
| | | | ATCCAGTTCTTCCTCGGTCGTCGGCATAA GTTT | 102 |
| 50 | 37 | N101S | CAGGTTCTGTGTTCGAGCCCGATAAGCG AGTTT | 103 |
| | | | AAACTCGCTTATCGGGCTCGAACACAGA ACCTG | 104 |
| 54 | 49 | N101S | CAGGTTCTGTGTTCGAGCCCGATAAGCG AGTTT | 105 |
| | | | AAACTCGCTTATCGGGCTCGAACACAGA ACCTG | 106 |

TABLE 2-3-continued

Primer for site-directed mutagenesis used in preparation of mutant AtGH3-6 (3)

| Mutant No. | Template | Introduced mutation point | Nucleotide sequence (5' to 3') | SEQ ID NO |
|---|---|---|---|---|
| 55 | 49 | Q200E | TATACCAGTCCGAATGAGACGATCTTGT GTTCC | 107 |
| | | | GGAACACAAGATCGTCTCATTCGGACTG GTATA | 108 |
| 56 | 49 | C576A | TACAAAACACCAAGAGCGGTCAAATTCG CGCCG | 109 |
| | | | CGGCGCGAATTTGACCGCTCTTGGTGTTT TGTA | 110 |

The obtained PCR product was digested with DpnI. Thereafter, *E. coli* JM109 was transformed with the reaction solution, and a target plasmid was extracted from a kanamycin resistant strain. This plasmid was defined as a mutant AtGH3-6 expression plasmid.

(2) A mutation was introduced into AtGH3-6 using pET-28a-AtGH3-6 (PCT/JP2019/007681) as a template. In addition, into some samples of mutant AtGH3-6, a mutation was further introduced using, as a template, a mutant AtGH3-6 expression plasmid obtained above or below. Mutagenesis was performed using PrimeSTAR GXL DNA Polymerase (Takara Bio Inc.) under the following conditions.

1 cycle 98° C., 30 sec 30 cycles 98° C., 10 sec

60° C., 15 sec

68° C., 7.5 min 1 cycle 72° C., 5 min

4° C., hold

Primers used are as follows.

TABLE 3

Primers for site-directed mutagenesis used in preparation of mutant AtGH3-6

| Mutant No. | Template | Introduced mutation point | Nucleotide sequence (5' to 3') | SEQ ID NO |
|---|---|---|---|---|
| 26 | 18 | S161P | TTCCTCTTCATCAAGCCGGAATCGAA AACCCCT | 111 |
| | | | AGGGGTTTTCGATTCCGGCTTGATGA AGAGGAA | 112 |
| 27 | 19 | S161P | TTCCTCTTCATCAAGCCGGAATCGAA AACCCCT | 113 |
| | | | AGGGGTTTTCGATTCCGGCTTGATGA AGAGGAA | 114 |
| 29 | 21 | S161P | TTCCTCTTCATCAAGCCGGAATCGAA AACCCCT | 115 |
| | | | AGGGGTTTTCGATTCCGGCTTGATGA AGAGGAA | 116 |
| 31 | 18 | M337G | CCGTTAGTCTGCACGGGCTATGCGAG CAGTGAA | 117 |
| | | | TTCACTGCTCGCATAGCCCGTGCAGA CTAACGG | 118 |
| 33 | 19 | M337G | CCGTTAGTCTGCACGGGCTATGCGAG CAGTGAA | 119 |
| | | | TTCACTGCTCGCATAGCCCGTGCAGA CTAACGG | 120 |
| 41 | 31 | K388N | TAGCTTGCCTAATGCACTGACCG | 121 |
| | | | CGGTCAGTGCATTAGGCAAGCTA | 122 |
| 47 | 31 | C576A | TACAAAACACCAAGAGCGGTCAAATT CGCGCCG | 123 |
| | | | CGGCGCGAATTTGACCGCTCTTGGTGT TTTGTA | 124 |

TABLE 3-continued

Primers for site-directed mutagenesis used in preparation of mutant AtGH3-6

| Mutant No. | Template | Introduced mutation point | Nucleotide sequence (5' to 3') | SEQ ID NO |
|---|---|---|---|---|
| 57 | 49 | K388N | TAGCTTGCCTAATGCACTGACCG | 125 |
| | | | CGGTCAGTGCATTAGGCAAGCTA | 126 |
| 58 | 56 | N101S | CAGGTTCTGTGTTCGAGCCCGATAAG CGAGTTT | 127 |
| | | | AAACTCGCTTATCGGGCTCGAACACA GAACCTG | 128 |
| 59 | 56 | Q200E | TATACCAGTCCGAATGAGACGATCTT GTGTTCC | 129 |
| | | | GGAACACAAGATCGTCTCATTCGGAC TGGTATA | 130 |

The obtained PCR product was digested with DpnI. Thereafter, *E. coli* JM109 was transformed with the reaction solution, and a target plasmid was extracted from a kanamycin resistant strain. This plasmid was defined as a mutant AtGH3-6 expression plasmid. As a result of confirming the sequence, a mutation of M337A was also introduced into Mutant No. 26 in addition to the introduced mutation point.

(3) A mutation was further introduced into AtGH3-6 using pET-28a-mutant AtGH3-6 (Mutant No. 56) as a template. PCR was performed using PrimeSTAR Max DNA Polymerase (Takara Bio Inc.) under the following conditions.

1 cycle 98° C., 30 sec 30 cycles 98° C., 10 sec

60° C., 15 sec

72° C., 5 sec/kb 1 cycle 72° C., 5 min

4° C., hold

Primers used are as follows.

TABLE 4

Primers for site-directed mutagenesis used in preparation of mutant AtGH3-6

| Mutant No. | Introduced mutation point | PCR | Nucleotide sequence (5' to 3') | SEQ ID NO |
|---|---|---|---|---|
| 60 | K388N | 1 | CGACGACCGAGGAAGAACTGGATCG TCG | 131 |
| | | | TCAGTGCATTAGGCAAGCTAATGCTG CT | 132 |
| | | 2 | TGCCTAATGCACTGACCGAAAAAGA ACA | 133 |
| | | | CTTCCTCGGTCGTCGGCATAAGTTTG CG | 134 |
| 61 | N101S/Q200E | 1 | GTTCGAGCCCGATAAGCGAGTTTCTC AC | 135 |
| | | | AGATCGTCTCATTCGGACTGGTATAG TT | 136 |
| | | 2 | CGAATGAGACGATCTTGTGTTCCGAC TC | 137 |
| | | | TTATCGGGCTCGAACACAGAACCTG CGA | 138 |
| 62 | N101S/K388N | 1 | GTTCGAGCCCGATAAGCGAGTTTCTC AC | 139 |
| | | | TCAGTGCATTAGGCAAGCTAATGCTG CT | 140 |
| | | 2 | TGCCTAATGCACTGACCGAAAAAGA ACA | 141 |
| | | | TTATCGGGCTCGAACACAGAACCTG CGA | 142 |
| 63 | Q200E/K388N | 1 | CGAATGAGACGATCTTGTGTTCCGAC TC | 143 |
| | | | TCAGTGCATTAGGCAAGCTAATGCTG CT | 144 |
| | | 2 | TGCCTAATGCACTGACCGAAAAAGA ACA | 145 |
| | | | AGATCGTCTCATTCGGACTGGTATAG TT | 146 |

TABLE 4-continued

Primers for site-directed mutagenesis used in preparation of mutant AtGH3-6

| Mutant No. | Introduced mutation point | PCR | Nucleotide sequence (5' to 3') | SEQ ID NO |
|---|---|---|---|---|
| 64 | N101S/Q200E/K388N | 1 | GTTCGAGCCCGATAAGCGAGTTTCTCAC | 147 |
| | | | AGATCGTCTCATTCGGACTGGTATAGTT | 148 |
| | | 2 | CGAATGAGACGATCTTGTGTTCCGACTC | 149 |
| | | | TCAGTGCATTAGGCAAGCTAATGCTGCT | 150 |
| | | 3 | TGCCTAATGCACTGACCGAAAAAGAACA | 151 |
| | | | TTATCGGGCTCGAACACAGAACCTGCGA | 152 |

The obtained PCR product was separated by agarose gel electrophoresis, then DNA having a target size was extracted from the agarose gel, and an In-Fusion reaction was performed using In-Fusion (registered trademark) HD Cloning Kit (Takara Bio Inc.). *E. coli* JM109 was transformed with the reaction solution, and a target plasmid was extracted from a kanamycin resistant strain. This plasmid was defined as a mutant AtGH3-6 expression plasmid.

(4) A plasmid in which a gene of mutant AtGH3-6 (SEQ ID NOs: 185 and 186) was inserted into NdeI and XhoI sites in a multiple cloning site of pET-28a (+), pET-28a-mutant AtGH3-6 (Mutant No. 36) was purchased from Eurofins Genomics.

Example 2: Construction of Mutant AtGH3-6 Expression Plasmid by Random Mutagenesis A mutation was introduced into AtGH3-6 using pET-28a-AtGH3-6 (PCT/JP2019/007681) as a template. Mutagenesis was performed using Gene Morph II Random Mutagenesis Kit (Agilent technology) under the following conditions.

1 cycle 95° C., 2 min
30 cycles 95° C., 30 sec
60° C., 30 sec
72° C., 1.2 min
1 cycle 72° C., 10 min
4° C., hold Primers used are as follows.

TABLE 5

Primer for random mutagenesis used in preparation of mutant AtGH3-6

| Nucleotide sequence (5' to 3') | SEQ ID NO |
|---|---|
| TAATACGACTCACTATAGGG | 153 |
| ATGCTAGTTATTGCTCAGCGG | 154 |

The obtained DNA fragment of about 2.1 kb was subjected to restriction enzyme treatment with NdeI and XhoI, and ligated with a vector-side DNA fragment of pET-28a-AtGH3-6 similarly treated with NdeI and XhoI. *E. coli* JM109 was transformed with this ligation solution, and a plasmid was extracted from a kanamycin resistant strain. This plasmid was defined as a mutant AtGH3-6 expression plasmid library. The obtained plasmid library was introduced into *E. coli* BL21 (DE3) to obtain a transformant having a mutant AtGH3-6 expression plasmid from a kanamycin resistant strain. A plasmid was extracted from the obtained transformant, and the sequence of AtGH3-6 was confirmed. As a result, the following amino acid substitutions were introduced.

TABLE 6

Mutation point of mutant AtGH3-6 obtained by random mutagenesis

| Mutant No. | Mutation point |
|---|---|
| R1_3-F11 | R350T/G379D |
| R1_5-H9 | V311A |
| R3_5-C8 | L137I |
| R4_1-A6 | Q200E |
| R5_5-D3 | K388N |
| R5_5-E7 | I123T |
| R6_2-H7 | C335S/L390P |
| R6_5-B7 | V140I |
| R7_2-C2 | N101S |
| R9_3-D4 | E483D |

Example 3: Purification of Mutant AtGH3-6

The mutant AtGH3-6 expression plasmids were each introduced into *E. coli* BL21 (DE3) to obtain a transformant having the plasmid from a kanamycin resistant strain. This strain was inoculated into 50 mL of an LB medium containing 50 mg/L kanamycin, and cultured by shaking using a Sakaguchi flask at 37° C. When OD610 reached 0.6, 1 mM IPTG was added, and cultured by shaking at 15° C. for 24 hours. After completion of the culture, bacterial cells were collected from 20 mL of the culture solution by centrifugation and suspended in 4 mL xTractor (trademark) Buffer (Takara Bio Inc.). 8 μL of 5 units/μL DNase I solution and 40 μL of 100× lysozyme solution attached to xTractor (trademark) Buffer Kit (Takara Bio Inc.) were added, and the resulting mixture was stirred by inversion and then left to stand at room temperature for 20 minutes. The supernatant obtained by centrifugation was subjected to TALON (registered trademark) Spin Column (Takara Bio Inc.), and purification was performed according to the manufacturer's protocol. As an equilibration buffer, 20 mM Tris-HCl (pH 8.0), 300 mM NaCl, and 10 mM imidazole were used. As an elution buffer, 20 mM Tris-HCl (pH 8.0), 300 mM NaCl, and 150 mM imidazole were used. The obtained eluate was collected, concentrated using Amicon Ultra-0.5 10 kDa (Merck), and subjected to buffer exchange in 20 mM Tris-HCl (pH 8.0) and 1 mM DTT to obtain a purified enzyme solution. The protein concentration of the obtained purified enzyme solution was measured using a protein assay CBB solution (5-fold concentration) (Nacalai Tesque) and using Quick Start BSA Standard Set (Bio-rad) as a standard sample.

Example 4: Measurement of Activity of Mutant AtGH3-6 to Each Amino Acid Substrate A 0.2 mL reaction solution having a pH of 8.0, the reaction solution containing 50 mM Tris-HCl, 5 mM L-glutamic acid or L-aspartic acid, 5 mM sodium laurate, 10 mM ATP, 10 mM $MgCl_2$, 1 mM DTT, and 50 μg/mL purified enzyme, was incubated at 25° C. for 24 hours. After completion of the reaction, 0.8 mL of a reaction stop solution (1.4% (w/v) phosphoric acid, 75% (v/v) methanol) was added, and the supernatant after centrifugation was subjected to UPLC-MS analysis. A signal of a molecular weight of Nα-lauroyl-L-glutamic acid (C12-L-Glu) or Nα-lauroyl-L-aspartic acid (C12-L-Asp) was extracted by a selected ion recording (SIR) method to confirm a peak area value, and the amount of production was quantified using a calibration curve of a sample.

UPLC-MS analysis conditions are as follows.

Analysis condition 1:

Apparatus: ACQUITY UPLC (Waters)

Column: ACQUITY UPLC BEH C18 1.7 μm 2.1×50 mm Column (Waters)

Mobile phase A: 0.1% formic acid

Mobile phase B: acetonitrile

Gradient:

A: B 60:40 to 20:80 Gradient 1.2 min

A: B 20:80 to 60:40 Gradient 0.01 min

A: B 60:40 Isocratic 0.29 min

Flow rate: 0.6 ml/min

Injection amount: 2 μL

Column temperature: 40° C.

Ionization method: ESI-negative

SIR: C12-L-Glu m/z328$^-$

C12-L-Asp m/z314$^-$

Analysis condition 2:

Apparatus: ACQUITY UPLC (Waters)

Column: ACQUITY UPLC BEH C18 1.7 μm 2.1×100 mm Column (Waters)

Mobile phase A: 0.1% formic acid

Mobile phase B: acetonitrile

Gradient:

A: B 60:40 to 20:80 Gradient 2.4 min

A: B 20:80 to 60:40 Gradient 0.1 min

A: B 60:40 Isocratic 0.5 min

Flow rate: 0.6 ml/min

Injection amount: 2 μL

Column temperature: 40° C.

Ionization method: ESI-negative

SIR: C12-L-Glu m/z328$^-$

C12-L-Asp m/z314$^-$

As a result of UPLC-MS analysis, it was confirmed that the production amount of Nα-lauroyl-L-glutamic acid (C12-L-Glu) and/or a substrate specificity to L-glutamic acid, production amount of C12-L-Glu/production amount of C12-L-Asp, was improved in the mutant AtGH3-6 as compared with the wild type AtGH3-6. WT in Table indicates wild type AtGH3-6.

TABLE 7-1

N-acylamino acid synthesis activity of each mutant AtGH3-6 to L-glutamic acid and L-aspartic acid as substrate (1)

| | | Product (mM) | | Substrate specificity |
|---|---|---|---|---|
| No | Mutation | C12-L-Asp | C12-L-Glu | C12-L-Glu/C12-L-Asp |
| WT | — | 0.76 | 0.06 | 0.08 |
| R18 | Y134F | 0.85 | 0.10 | 0.11 |
| R20 | Y134V | 0.96 | 0.08 | 0.08 |
| R30 | S161P | 0.75 | 0.14 | 0.18 |
| R32 | V174A | 0.66 | 0.11 | 0.16 |
| WT | — | 0.93 | 0.07 | 0.08 |
| R55 | T336S | 1.05 | 0.09 | 0.08 |
| R56 | M337G | 1.13 | 0.15 | 0.14 |
| R59 | A339G | 0.98 | 0.13 | 0.14 |
| R61 | S340A | 0.78 | 0.10 | 0.13 |
| WT | — | 1.41 | 0.09 | 0.06 |
| R39 | V231A | 0.98 | 0.18 | 0.19 |
| R68 | Y344G | 1.54 | 0.11 | 0.07 |
| R69 | Y344A | 1.74 | 0.12 | 0.07 |
| R70 | Y344V | 1.35 | 0.19 | 0.14 |
| R78 | S455T | 1.25 | 0.14 | 0.11 |
| R1002 | T122S/I123T | 1.81 | 0.10 | 0.05 |
| R1005 | R117P/Q533R | 0.08 | 0.14 | 1.74 |
| WT | — | 1.65 | 0.09 | 0.05 |
| R1_3-F11 | R350T/G379D | 2.16 | 0.16 | 0.08 |
| R1_5-H9 | V311A | 1.82 | 0.25 | 0.14 |
| R3_5-C8 | L137I | 2.84 | 0.19 | 0.07 |
| WT | — | 0.55 | 0.03 | 0.05 |
| R4_1-A6 | Q200E | 0.84 | 0.07 | 0.09 |
| R5_5-D3 | K388N | 0.71 | 0.08 | 0.11 |
| R5_5-E7 | I123T | 1.16 | 0.12 | 0.10 |
| R7_2-C2 | N101S | 0.72 | 0.05 | 0.07 |
| WT | — | 0.83 | 0.07 | 0.09 |
| R6_2-H7 | C335S/L390P | 0.88 | 0.11 | 0.13 |
| R6_5-B7 | V140I | 1.00 | 0.10 | 0.10 |
| R9_3-D4 | E483D | 1.00 | 0.09 | 0.09 |
| WT | — | 1.92 | 0.18 | 0.09 |
| 4 | C576A | 1.99 | 0.38 | 0.19 |
| WT | — | 2.29 | 0.15 | 0.07 |
| 7 | S161P/V174A | 1.67 | 0.64 | 0.38 |
| 8 | S161P/V231A | 1.69 | 0.69 | 0.41 |
| 10 | S161P/Y344V | 2.52 | 1.05 | 0.42 |
| 11 | V174A/V231A | 1.49 | 0.70 | 0.47 |
| 15 | V231A/Y344V | 1.63 | 0.35 | 0.21 |
| 18 | R117P/V174A/Q533R | 0.23 | 0.66 | 2.85 |
| 19 | R117P/V231A/Q533R | 0.38 | 1.43 | 3.74 |
| 20 | R117P/M337G/Q533R | 0.13 | 0.53 | 4.24 |
| 21 | R117P/Y344V/Q533R | 0.32 | 0.84 | 2.65 |
| 24 | Y344I | 2.14 | 0.17 | 0.08 |

TABLE 7-2

N-acylamino acid synthesis activity of each mutant AtGH3-6 to L-glutamic acid and L-aspartic acid as substrate (2)

| | | Product (mM) | | Substrate specificity |
|---|---|---|---|---|
| No. | Mutation | C12-L-Asp | C12-L-Glu | C12-L-Glu/C12-L-Asp |
| WT | — | 2.37 | 0.34 | 0.14 |
| 9 | S161P/M337G | 2.95 | 2.11 | 0.72 |
| 12 | V174A/M337G | 2.58 | 1.62 | 0.63 |
| 13 | V174A/Y344V | 2.40 | 0.68 | 0.28 |
| 14 | V231A/M337G | 1.92 | 1.12 | 0.58 |
| 17 | R117P/S161P/Q533R | 0.32 | 1.07 | 3.32 |
| WT | — | 2.11 | 0.23 | 0.11 |
| 16 | M337G/Y344V | 1.94 | 0.80 | 0.41 |
| WT | — | 1.85 | 0.08 | 0.04 |
| 30 | R117P/V174A/V231A/Q533R | 0.30 | 1.26 | 4.19 |
| 32 | R117P/V174A/Y344V/Q533R | 0.12 | 0.46 | 3.76 |
| WT | — | 1.78 | 0.10 | 0.06 |

TABLE 7-2-continued

N-acylamino acid synthesis activity of each mutant AtGH3-6 to L-glutamic acid and L-aspartic acid as substrate (2)

| | | Product (mM) | | Substrate specificity |
|---|---|---|---|---|
| No. | Mutation | C12-L-Asp | C12-L-Glu | C12-L-Glu/C12-L-Asp |
| 34 | R117P/V231A/Y344V/Q533R | 0.08 | 0.37 | 4.63 |
| WT | — | 2.28 | 0.24 | 0.10 |
| 26 | R117P/S161P/V174A/M337A/Q533R | 0.84 | 1.79 | 2.12 |
| 29 | R117P/S161P/Y344V/Q533R | 0.59 | 1.27 | 2.16 |
| 31 | R117P/V174A/M337G/Q533R | 1.22 | 2.20 | 1.81 |
| 33 | R117P/V231A/M337G/Q533R | 0.40 | 1.61 | 3.98 |
| WT | — | 2.20 | 0.26 | 0.12 |
| 27 | R117P/S161P/V231A/Q533R | 0.26 | 0.88 | 3.41 |
| 36 | R117P/S161P/V174A/V231A/M337G/Y344V/Q533R | 0.51 | 1.04 | 2.03 |
| WT | — | 2.02 | 0.15 | 0.08 |
| 31 | R117P/V174A/M337G/Q533R | 0.64 | 2.14 | 3.34 |
| 38 | R117P/V174A/V311A/M337G/Q533R | 0.70 | 2.47 | 3.55 |
| 39 | R117P/L137I/V174A/M337G/Q533R | 0.66 | 2.43 | 3.66 |
| 40 | R117P/V174A/Q200E/M337G/Q533R | 0.90 | 2.88 | 3.19 |
| WT | — | 1.47 | 0.15 | 0.10 |
| 31 | R117P/V174A/M337G/Q533R | 0.55 | 1.72 | 3.11 |
| 41 | R117P/V174A/M337G/K388N/Q533R | 0.91 | 2.26 | 2.47 |
| 46 | N101S/R117P/I123T/V174A/M337G/Q533R | 0.93 | 2.30 | 2.46 |
| 47 | R117P/V174A/M337G/Q533R/C576A | 0.99 | 2.49 | 2.51 |

TABLE 7-3

N-acylamino acid synthesis activity of each mutant AtGH3-6 to L-glutamic acid and L-aspartic acid as substrate (3)

| | | Product (mM) | | Substrate specificity |
|---|---|---|---|---|
| No. | Mutation | C12-L-Asp | C12-L-Glu | C12-L-Glu/C12-L-Asp |
| WT | — | 2.02 | 0.07 | 0.03 |
| 31 | R117P/V174A/M337G/Q533R | 0.68 | 1.26 | 1.86 |
| 37 | R117P/V174A/M337G/R350T/G379D/Q533R | 1.21 | 1.84 | 1.51 |
| 42 | R117P/I123T/V174A/M337G/Q533R | 1.43 | 2.14 | 1.50 |
| 43 | N101S/R117P/V174A/M337G/Q533R | 0.95 | 1.72 | 1.82 |
| 44 | R117P/I123T/V174A/Q200E/M337G/Q533R | 1.53 | 2.07 | 1.35 |
| 45 | N101S/R117P/V174A/Q200E/M337G/Q533R | 1.07 | 1.72 | 1.60 |
| 48 | R117P/V174A/Q200E/M337G/R350T/G379D/Q533R | 1.21 | 2.00 | 1.65 |
| 49 | R117P/I123T/V174A/M337G/R350T/G379D/Q533R | 1.80 | 2.38 | 1.32 |

TABLE 7-3-continued

N-acylamino acid synthesis activity of each mutant AtGH3-6 to L-glutamic acid and L-aspartic acid as substrate (3)

| | | Product (mM) | | Substrate specificity |
|---|---|---|---|---|
| No. | Mutation | C12-L-Asp | C12-L-Glu | C12-L-Glu/C12-L-Asp |
| 50 | N101S/R117P/V174A/M337G/R350T/G379D/Q533R | 1.36 | 2.25 | 1.66 |
| WT | — | 2.00 | 0.24 | 0.12 |
| 31 | R117P/V174A/M337G/Q533R | 0.83 | 2.01 | 2.43 |
| 49 | R117P/I123T/V174A/M337G/R350T/G379D/Q533R | 1.73 | 3.07 | 1.77 |
| 54 | N101S/R117P/I123T/V174A/M337G/R350T/G379D/Q533R | 1.41 | 3.01 | 2.13 |
| 55 | R117P/I123T/V174A/Q200E/M337G/R350T/G379D/Q533R | 1.38 | 2.83 | 2.05 |
| 56 | R117P/I123T/V174A/M337G/R350T/ G379D/Q533R/C576A | 2.23 | 3.28 | 1.47 |
| 57 | R117P/I123T/V174A/M337G/R350T/G379D/K388N/Q533R | 1.81 | 3.00 | 1.65 |

TABLE 7-4

N-acylamino acid synthesis activity of each mutant AtGH3-6 to L-glutamic acid and L-aspartic acid as substrate (4)

| | | Product (mM) | | Substrate specificity |
|---|---|---|---|---|
| No. | Mutation | C12-L-Asp | C12-L-Glu | C12-L-Glu/C12-L-Asp |
| WT | — | 1.66 | 0.10 | 0.06 |
| 31 | R117P/V174A/M337G/Q533R | 0.81 | 1.60 | 1.98 |
| 49 | R117P/I123T/V174A/M337G/R350T/G379D/Q533R | 1.89 | 2.61 | 1.38 |
| 56 | R117P/I123T/V174A/M337G/R350T/G379D/Q533R/C576A | 2.53 | 3.24 | 1.28 |
| 58 | N101S/R117P/I123T/V174A/M337G/R350T/G379D/Q533R/C576A | 2.12 | 2.92 | 1.38 |
| 59 | R117P/I123T/V174A/Q200E/M337G/R350T/G379D/Q533R/C576A | 2.31 | 3.05 | 1.32 |
| 60 | R117P/I123T/V174A/M337G/R350T/G379D/K388N/Q533R/C576A | 2.38 | 3.26 | 1.37 |
| 61 | N101S/R117P/I123T/V174A/Q200E/M337G/R350T/G379D/Q533R/C576A | 2.26 | 3.12 | 1.38 |
| 62 | N101S/R117P/I123T/V174A/M337G/R350T/G379D/K388N/Q533R/C576A | 2.48 | 3.11 | 1.25 |
| 63 | R117P/I123T/V174A/Q200E/M337G/R350T/G379D/K388N/Q533R/C576A | 2.44 | 3.23 | 1.33 |

TABLE 7-4-continued

| N-acylamino acid synthesis activity of each mutant AtGH3-6 to L-glutamic acid and L-aspartic acid as substrate (4) | | | | |
|---|---|---|---|---|
| | | Product (mM) | | Substrate specificity |
| No. | Mutation | C12-L-Asp | C12-L-Glu | C12-L-Glu/C12-L-Asp |
| 64 | N101S/R117P/I123T/V174A/Q200E/M337G/R350T/G379D/K388N/Q533R/C576A | 2.77 | 3.25 | 1.17 |

Example 5: Measurement of Activity of Mutant AtGH3-6 to Each Fatty Acid Substrate A 0.2 mL reaction solution having a pH of 8.0, the reaction solution containing 50 mM Tris-HCl, 5 mM L-glutamic acid, 5 mM fatty acid sodium (or fatty acid), 10 mM ATP, 10 mM $MgCl_2$, 1 mM DTT, and 50 μg/mL purified enzyme, was incubated at 25° C. for 24 hours. The sodium fatty acid (or fatty acid) to be added to the enzymatic reaction was dissolved in 20% (v/v) Triton X-100 to prepare a 25 mM solution, and the solution was added to the reaction solution so as to have a final concentration of 5 mM. After completion of the reaction, 0.8 mL of a reaction stop solution (1.4% (w/v) phosphoric acid, 75% (v/v) methanol) was added, and the supernatant after centrifugation was subjected to UPLC-MS analysis. A signal of the molecular weight of an assumed Nα-acyl-L-glutamic acid was extracted by an SIR method, a peak area value was confirmed, and the amount of production was quantified using a calibration curve of a sample. For quantification of C6-L-Glu and C8-L-Glu, C8-L-Glu was used, for quantification of C10-L-Glu, C10-L-Glu was used, and for quantification of Nα-acyl-L-Glu having an acyl group having a carbon chain length of C12 or more, C12-L-Glu was used as a standard sample. As the sodium fatty acid (or fatty acid), sodium caproate, sodium caprylate, sodium caprate, sodium laurate, sodium myristate, sodium palmitate, cis-5-dodecenoic acid, cis-9-tetradecenoic acid, or cis-9-hexadecenoic acid was used. A saturated fatty acid having x carbon atoms is represented by Cx, and an unsaturated fatty acid having x carbon atoms and y carbon-carbon double bonds is represented by Cx: y.

UPLC-MS analysis conditions are as follows:

Apparatus: ACQUITY UPLC (Waters)

Column: ACQUITY UPLC BEH C18 1.7 μm 2.1×50 mm Column (Waters)

Mobile phase A: 0.1% formic acid

Mobile phase B: acetonitrile

Gradient:

A: B 90:10 to 0:100 Gradient 1.8 min

A: B 0:100 Isocratic 0.6 min

A: B 0:100 to 90:10 Gradient 0.1 min

A: B 90:10 Isocratic 0.5 min

Flow rate: 0.6 ml/min

Injection amount: 2 μL

Column temperature: 40° C.

Ionization method: ESI-negative

TABLE 8

| MS ions detected by SIR method | |
|---|---|
| Nα-acyl-L-Glu | m/z $^-$ |
| C6-L-Glu | 244 |
| C8-L-Glu | 272 |
| C10-L-Glu | 300 |
| C12-L-Glu | 328 |
| C12:1-L-Glu | 326 |
| C14-L-Glu | 356 |
| C14:1-L-Glu | 354 |
| C16-L-Glu | 384 |
| C16:1-L-Glu | 382 |

As a result of UPLC-MS analysis, it was confirmed that the production amounts of various Nα-acyl-L-glutamic acids each having an acyl group having a carbon chain number of 8 or more were improved in the mutant AtGH3-6 as compared with the wild type AtGH3-6. WT in Table indicates wild type AtGH3-6.

TABLE 9

| N-acylamino acid synthesis activity of each mutant AtGH3-6 to each fatty acid substrate | | | | | | | | | | |
|---|---|---|---|---|---|---|---|---|---|---|
| Mutant | | Nα-acyl-L-Glu (mM) | | | | | | | | |
| No. | Mutation point | C6 | C8 | C10 | C12 | C12:1 | C14 | C14:1 | C16 | C16:1 |
| WT | — | 1.14 | 0.30 | 0.35 | 0.50 | 1.03 | 0.64 | 0.17 | 0.07 | 2.21 |
| 31 | R117P/V174A/M337G/Q533R | 0.14 | 1.37 | 2.72 | 3.11 | 3.12 | 1.67 | 1.70 | 0.24 | 4.38 |
| 49 | R117P/I123T/V174A/M337G/R350T/G379D/Q533R | 0.22 | 1.47 | 3.12 | 3.12 | 3.61 | 1.52 | 1.95 | 0.12 | 4.01 |
| 56 | R117P/I123T/V174A/M337G/R350T/G379D/Q533R/C576A | 0.35 | 1.50 | 2.89 | 3.17 | 3.25 | 2.62 | 2.14 | 0.28 | 4.97 |
| 61 | N101S/R117P/I123T/V174A/Q200E/M337G/R350T/G379D/Q533R/C576A | 0.41 | 1.62 | 2.44 | 3.80 | 3.25 | 2.50 | 1.92 | 0.33 | 3.97 |

Example 6: Construction of Fatty Acid Producing Strain (*E. coli*)

As a strain that produces a fatty acid from a carbon source such as glucose, an acyl-CoA synthetase (fadD)-deleted/acyl-ACP thioesterase-enhanced *E. coli* strain (*E. coli* ΔfadD/pMW118-Ptac-UcTEopt) was constructed according to the following procedure.

(1) Synthesis of UcTE (acyl-ACP thioesterase derived from *Umbellularia californica*) gene Acyl-ACP thioesterase is known as a plant-derived enzyme involved in synthesis of a medium-chain fatty acid. This enzyme can be used to modify a chain length in bacterial fatty acid synthesis. Medium-chain acyl-ACP thioesterase (UcTE, GenBank: M94159) derived from California bay (*Umbellularia californica*) that predominantly produces lauric acid in oilseeds has been studied and has been used for lauric acid production in *E. coli* (Voelker and Davies, J. of Bacteriol. 1994; 176 (23): 7320-7327). Although it has been clarified that a transport peptide exists in an N-terminal region of UcTE (SEQ ID NO: 187), it has been indicated that the transport peptide is not essential for an enzymatic activity of UcTE (Feng et al. ACS Chem Biol. 2017; 12 (11): 2830-2836). Therefore, for construction of an expression plasmid of a UcTE gene, a truncated gene containing no transport peptide, that is, a gene encoding a protein having an amino acid sequence in which an initiating methionine is added to amino acid residues at positions 84 to 382 in the amino acid sequence of SEQ ID NO: 3, was used. The sequence of the truncated UcTE gene in which a codon is optimized for expression in *E. coli* is shown in SEQ ID NO: 4. For the UcTE gene in which a codon is optimized for expression in *E. coli*, gene synthesis was requested to Eurofins Genomics, and a plasmid in which a DNA fragment containing the gene was inserted into a pEX-K4J1 vector (pEX-K4J1-UcTEopt) was purchased.

(2) Construction of pMW118-Sce-Km plasmid

In order to obtain plasmids available in both *E. coli* and *P. ananatis*, an expression vector pMW118-Sce-Km was constructed. This plasmid contains a kan gene (kanamycin resistant marker) and a bla gene (ampicillin resistant marker). Based on a pMW118-placUV5-lacI plasmid (Skorokhodova et al., Biotechnologiya (Russian). 2004; 5:3-21), the pMW118-Sce-Km plasmid (FIG. 1) was constructed. A kan gene (kanamycin resistant marker) encoding aminoglycoside phosphotransferase and a DNA fragment containing an RBS thereof were PCR-amplified using pUC-4K (GenBank/EMBL accession number X06404, Pharmacia) as a template (Mashko et al., Biotekhnologiya. 2001; 5:3-20). Primers used are as follows.

TABLE 10

Primer for amplification of DNA fragment containing kan gene and RBS thereof

| Primer No. | Nucleotide sequence (5' to 3') | SEQ ID NO |
|---|---|---|
| P1 | TCTGATCTAGATAGGGATAACAGGGTAATCAACCAATTAACCAATTCTGATTAGAA | 155 |
| P2 | GGAAAGGATCCGCGGCCGCCACGTTGTGTCTCAAAATCTC | 156 |

TABLE 10-continued

The obtained DNA fragment was inserted into BamHI and XbaI sites of the pMW118-placUV5-lacI plasmid by a ligation reaction with T4 DNA ligase (Thermo Fisher Scientific). *E. coli* TG1 was transformed with this ligation reaction solution and grown on an LB agar medium containing 50 mg/L kanamycin, and then pMW118-Sce-Km was extracted from a kanamycin resistant strain. The structure of the plasmid was confirmed by sequence analysis (FIG. 1).

(3) Construction of pMW118-Ptac-UcTEopt Plasmid

A DNA fragment containing a truncated UcTEopt gene which was fused to RBS (RBST7) derived from a T7 phage and to which a restriction enzyme site was added was PCR-amplified using a pEX-K4J1-UcTEopt plasmid as a template. Primers used are as follows.

TABLE 11

Primer for amplification of DNA fragment containing RBST7 and truncated UcTEopt gene

| Primer No. | Nucleotide sequence (5' to 3') | SEQ ID NO |
|---|---|---|
| P3 | TTTTTTCTAGAAATAATTTTGTTTAACTTTAAGAAGGAGATATACCATGCTAGAGTGGAAACCGAAACCG | 157 |
| P4 | TTTTTGGATCCTCGAGTTAAACGCGAGGTTCCGCAG | 158 |

A DNA fragment to which a restriction enzyme site was added and which contained a Ptac promoter was PCR-amplified using a chromosomal DNA (Katashkina et al. Molecular Biology. 2005; 39 (5): 719-726) into which a Ptac promoter was introduced as a template. Primers used are as follows.

TABLE 12

Primer for amplification of DNA fragment containing Ptac promoter

| Primer No. | Nucleotide sequence (5' to 3') | SEQ ID NO |
|---|---|---|
| P5 | TTTTTAGATCTCCCTGTTGACAATTAATCATCGG | 159 |
| P6 | CTGTTTCTAGATCCTGTGTGAAATTGTTATCCGC | 160 |

The obtained DNA fragment containing RBST7 and a truncated UcTEopt gene and the obtained DNA fragment containing a Ptac promoter were treated with XbaI, and both DNA fragments were ligated using T4 DNA ligase (Thermo Fisher Scientific). A DNA fragment containing Ptac-RBST7-UcTEopt (SEQ ID NO: 6) to which BglII and an EcoRI sites were added was PCR-amplified using this ligation reaction solution as a template. Primers used are as follows.

TABLE 13

| Primer for amplification of DNA fragment containing Ptac-RBST7-UcTEopt | | |
|---|---|---|
| Primer No. | Nucleotide sequence (5' to 3') | SEQ ID NO |
| P5 | TTTTTAGATCTCCCTGTTGACAATTAATCATCGG | 161 |
| P7 | TTTTTGAATTCGAGCTCGGTACCAATAATTTTGT TTAACTTTAAGAAGGAGATATACC | 162 |

Figure 2:
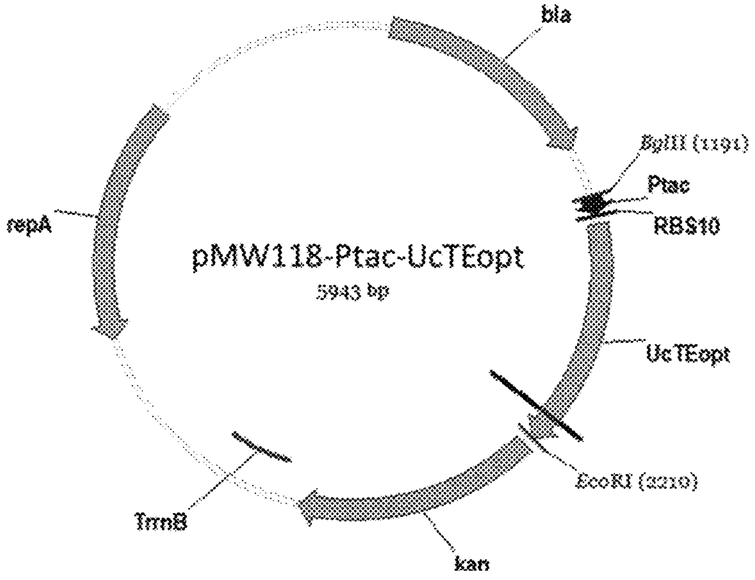
FIG. 2 is a diagram illustrating a structure of a plasmid pMW118-Ptac-UcTEopt.

The obtained DNA fragment was inserted into BglII and EcoRI sites of pMW118-Sce-Km by a ligation reaction with T4 DNA ligase (Thermo Fisher Scientific). *E. coli* TG1 was transformed with this ligation reaction solution and grown on an LB agar medium containing 50 mg/L kanamycin, and then a pMW118-Ptac-UcTEopt plasmid was extracted from a kanamycin resistant strain. The structure of the plasmid was confirmed by sequence analysis (FIG. 2).

(4) Construction of *E. coli* AfadD/pMW118-Ptac-UcTEopt (Fatty Acid Producing Strain)

For construction of a fatty acid producing strain of *E. coli, E. coli* K-12 MG1655 (F-lambda-ilvG-rfb-50 rph-ATCC 47076) was used as a base strain. In order to block a fatty acid degradation pathway, in-frame deletion of a fadD gene was performed. Using a PCR-amplified DNA fragment containing λattL-kan-λattR to which a 40 bp region homologous to the fadD gene was added, deletion by a λ-Red method was performed in a similar manner to a previously reported method (Katashkina et al., BMC Mol Biol. 2009; 10:34). After electroporation, a strain was grown on an LB agar medium with 50 mg/L kanamycin. The DNA fragment used to replace the fadD gene with λattL-kan-λattR was PCR-amplified using genome DNA into which a λattL-kan-λattR cassette was introduced (Katashkina et al., BMC Mol Biol. 2009; 10:34) as a template. Primers used are as follows.

TABLE 14

| Primer for amplification of DNA fragment containing λattL-kan-λattR (DNA fragment for fadD gene deletion) | | |
|---|---|---|
| Primer No. | Nucleotide sequence (5' to 3') | SEQ ID NO |
| P9 | TGAGCTGACGGCGGCAAAAAGTCACCAGTGACTCTTCG GTTGAAGCCTGCTTTTTTATACTAAGTTGG | 163 |
| P10 | CAACCTGCGTTTGTGAATATGGGGGAGGTAATGACCTT CCCGCTCAAGTTAGTATAAAAAAGCTGAAC | 164 |

The obtained *E. coli* MG1655 AfadD:: λattL-kan-λattR was confirmed by PCR. Primers used are as follows.

TABLE 15

| Primer for confirming deletion of fadD gene | | |
|---|---|---|
| Primer No. | Nucleotide sequence (5' to 3') | SEQ ID NO |
| P11 | TGCGATGACGACGAACACGC | 165 |
| P12 | GATTAACCGGCGTCTGACGAC | 166 |

From the obtained strain, a kanamycin resistant marker (kan gene) was removed by a previously reported phage λInt/Xis-dependent method (Katashkina et al., BMC Mol Biol. 2009; 10:34). Removal of the marker from a chromosome was confirmed by PCR. Primers used are as follows.

TABLE 16

| Primer for confirming removal of kanamycin resistant marker (kan gene) | | |
|---|---|---|
| Primer No. | Nucleotide sequence (5' to 3') | SEQ ID NO |
| P11 | TGCGATGACGACGAACACGC | 167 |
| P12 | GATTAACCGGCGTCTGACGAC | 168 |

The obtained strain (*E. coli* MG1655 λfadD::λattB) was transformed with a pMW118-Ptac-UcTEopt plasmid by an electroporation method to obtain *E. coli* ΔfadD/pMW118-Ptac-UcTEopt as a fatty acid producing strain.

Example 7: Construction of Fatty Acid Producing Strain (*P. ananatis*)

As a strain that produces a fatty acid from a carbon source such as glucose, a fadD-deleted/gcd-deleted/acyl-ACP thioesterase-enhanced *P. ananatis* strain (*P. ananatis* SC17 (0) ΔfadD Δgcd/pMW118-PlacUV5-lacI-UcTEopt) was constructed according to the following procedure.

(1) Construction of pMW118-PlacUV5-lacI-UcTEopt Plasmid

A DNA fragment containing RBST7 and a truncated UcTEopt gene was PCR-amplified using the pMW118-Ptac-UcTEopt plasmid described in Example 6 as a template. Primers used are as follows.

TABLE 17

| Primer for amplification of DNA fragment containing RBST7 and truncated UcTEopt gene | | |
|---|---|---|
| Primer No. | Nucleotide sequence (5' to 3') | SEQ ID NO |
| P4 | TTTTTGGATCCTCGAGTTAAACGCGAGGTTCCGCAG | 169 |
| P8 | TTTTTGAGCTCGAATTCTTAAACGCGAGGTTCCGCAG | 170 |

Figure 3:
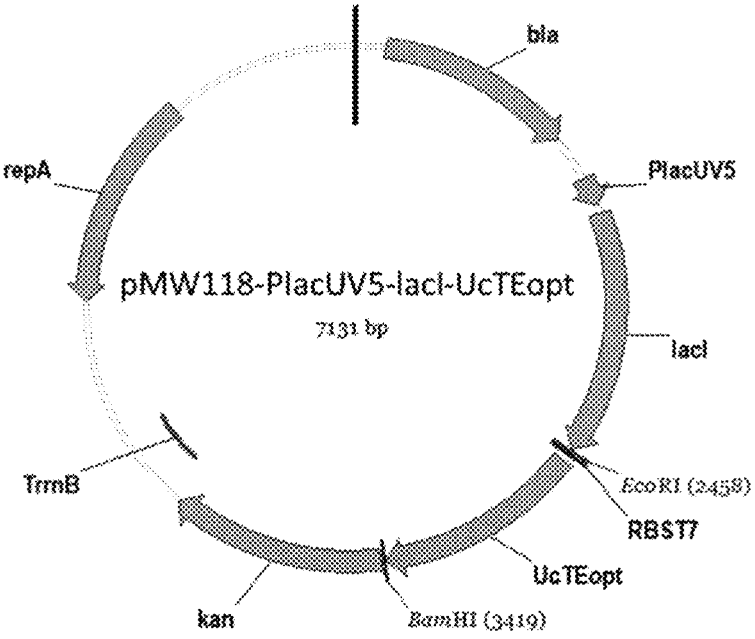
FIG. 3 is a diagram illustrating a structure of a plasmid pMW118-PlacUV5-lacI-UcTEopt.

The obtained DNA fragment was inserted into EcoRI and BamHI sites of a pMW118-Sce-Km plasmid by a ligation reaction with T4 DNA ligase (Thermo Fisher Scientific). *E. coli* TG1 was transformed with this ligation reaction solution and grown on an LB agar medium containing 50 mg/L kanamycin, and then a pMW118-PlacUV5-lacI-UcTEopt plasmid was extracted from a kanamycin resistant strain. The structure of the plasmid was confirmed by sequence analysis (FIG. 3).

(2) Construction of *P. ananatis* SC17 (0) ΔfadD Δgcd/pMW118-PlacUV5-lacI-UcTEopt For construction of a fatty acid producing strain of *P. ananatis, P. ananatis* SC17 (0) (Katashkina J I et al., BMC Mol Biol. 2009; 10:34) was used as a base strain. In order to block a fatty acid degradation pathway, in-frame deletion of a fadD gene (PAJ_1453) was performed. Using a PCR-amplified DNA fragment containing λattL-kan-λattR to which a 40 bp region homologous to the fadD gene was added, deletion by a λ-Red method was performed in a similar manner to a previously reported method (Katashkina et al., BMC Mol Biol. 2009; 10:34). After electroporation, a strain was grown on an LB agar medium with 50 mg/L kanamycin. The DNA fragment used to replace the fadD gene with λattL-kan-λattR was PCR-amplified using genome DNA into which a λattL-kan-λattR cassette was introduced (Katashkina et al., BMC Mol Biol. 2009; 10:34) as a template. Primers used are as follows.

TABLE 18

Primer for amplification of DNA fragment containing λattL-kan-λattR (DNA fragment for fadD gene deletion)

| Primer No. | Nucleotide sequence (5' to 3') | SEQ ID NO |
|---|---|---|
| P13 | CTGACGACGACAGTGATCGAGCAGCTCTTCTTTGGTC AGCTGAAGCCTGCTTTTTTATACTAAGTTGG | 171 |
| P14 | CTCTGGTTGATCTGTTTGAGCAGGCCGTTTCCCGTTAC GCCGCTCAAGTTAGTATAAAAAAGCTGAAC | 172 |

The obtained *P. ananatis* SC17 (0) ΔfadD::λattL-kan-λattR was confirmed by PCR. Primers used are as follows.

TABLE 19

Primer for confirming deletion of fadD gene

| Primer No. | Nucleotide sequence (5' to 3') | SEQ ID NO |
|---|---|---|
| P15 | CAAATGCGATTGTCGAGGCG | 173 |
| P16 | CCGGCGTTCAACCTGAATCC | 174 |

From the obtained strain, a kanamycin resistant marker (kan gene) was removed by a previously reported phage λInt/Xis-dependent method (Katashkina et al., BMC Mol Biol. 2009; 10:34). Removal of the marker from a chromosome was confirmed by PCR. Primers used are as follows.

TABLE 20

Primer for confirming removal of kanamycin resistant marker (kan gene)

| Primer No. | Nucleotide sequence (5' to 3') | SEQ ID NO |
|---|---|---|
| P15 | CAAATGCGATTGTCGAGGCG | 175 |
| P16 | CCGGCGTTCAACCTGAATCC | 176 |

The obtained strain was named as *P. ananatis* SC17 (0) ΔfadD::λattB.

Next, deletion of a god gene (PAJ_3473) was performed. Genome DNA (Katashkina et al., Biotekhnologiya. 2019; 35 (2): 3-15) isolated from *P. ananatis* SC17 (0) Δgcd::λattR-attLϕ80-kan-attRϕ80 using Wizard genomic DNA Purification Kit (Promega) was electroporated into the *P. ananatis* SC17 (0) ΔfadD::λattB strain according to a previously reported method (Katashkina et al., BMC Mol Biol. 2009; 10:34). The introduction of a Δgcd::λattR-attLϕ80-kan-attRϕ80 cassette was confirmed using the following primers.

TABLE 21

Primer for confirming deletion of gcd gene

| Primer No. | Nucleotide sequence (5' to 3') | SEQ ID NO |
|---|---|---|
| P17 | AGGGCAGATAGCAGGCATAA | 177 |
| P18 | TCTGATTGTTTTCCTGAGTTTTC | 178 |

The obtained strain was named as *P. ananatis* SC17 (0) ΔfadD::λattB Δgcd::λattR-attLϕ80-kan-attRλ80. From this strain, a kanamycin resistant marker (kan gene) was removed by a previously reported method using a pAH129-cat helper plasmid (Andreeva et al., FEMS Microbiol Lett. 2011; 318 (1): 55-60). Removal of the marker was confirmed by PCR. Primers used are as follows.

TABLE 22

Primer for confirming removal of kanamycin resistant marker (kan gene)

| Primer No. | Nucleotide sequence (5' to 3') | SEQ ID NO |
|---|---|---|
| P17 | AGGGCAGATAGCAGGCATAA | 179 |
| P18 | TCTGATTGTTTTCCTGAGTTTTC | 180 |

The obtained strain (*P. ananatis* SC17 (0) ΔfadD::λattB Δgcd::λattR-attBϕ80) was transformed with a pMW118-PlacUV5-lacI-UcTEopt plasmid by an electroporation method and grown on an LB agar medium containing 50 to 200 mg/L kanamycin to obtain *P. ananatis* SC17 (0) ΔfadD Δgcd/pMW118-PlacUV5-lacI-UcTEopt as a fatty acid producing strain.

Example 8: Synthesis of Lauric Acid from Glucose Using Fatty Acid Producing Strain Each of the fatty acid producing strains constructed in Examples 6 and 7 was inoculated into a K-medium agar medium (K-medium: LB medium to which 0.5 x M9 salt and 5 g/L D-glucose were added) containing 50 mg/L kanamycin and incubated at 30° C. for 16 hours. The strains evaluated are as follows.

TABLE 23

Fatty acid producing strain used for evaluating synthesis of lauric acid (fatty acid producing strains constructed in Examples 6 and 7)

| Strain No. | Host | Plasmid |
|---|---|---|
| 1 | *E. coli* ΔfadD | pMW118-Ptac-UcTEopt |
| 2 | *P. ananatis* ΔfadDΔgcd | pMW118-PlacUV5-lacI-UcTEopt |

The obtained bacterial cells were inoculated into 50 mL of an evaluation medium, and cultured by shaking using 500 mL of Ultra Yield (trademark) Flask (THOMSON) at 30° C. and 220 rpm. When Strain No. 2 was cultured, 1 mM IPTG was added to the medium. The composition of the evaluation medium is as follows.

TABLE 24

Composition of evaluation medium of fatty acid producing strain

| Raw material name | Concentration |
|---|---|
| D-glucose | 40 g/L |
| $MgSO_4$•$7H_2O$ | 1 g/L |
| $(NH_4)_2SO_4$ | 16 g/L |
| $KH_2PO_4$ | 0.3 g/L |
| KCl | 1 g/L |
| MES | 10 g/L |
| D-pantothenic acid calcium salt | 10 mg/L |
| betaine | 1 g/L |
| Bacto ™ Tryptone | 1 g/L |
| Bacto ™ Yeast Extract | 1 g/L |
| $FeSO_4$•$7H_2O$ | 10 mg/L |
| $MnSO_4$•$5H_2O$ | 10 mg/L |
| L-Lys•HCl | 125 mg/L |
| L-Met | 100 mg/L |
| 2,6-diaminopimelic acid (DAP) | 100 mg/L |
| $CaCO_3$ | 30 g/L |
| kanamycin monosulfate | 50 mg/L |

After completion of the culture, 1 mL of the culture solution was well mixed and centrifuged to obtain bacterial cells. To the bacterial cells, 1 mL of 1.4% (w/v) phosphoric acid, 75% (v/v) methanol (containing 1000 ppm tridecylic acid as an internal standard) was added, and the resulting mixture was mixed with a vortex mixer for three minutes. The supernatant obtained by the centrifugation was subjected to GC and GC-MS analysis.

GC analysis conditions are as follows.

Apparatus: GC-2010 (SHIMADZU)

Column: DB-FFAP 30 m, ID 0.25 mm, film 0.25 μm (Agilent Technologies)

Injection amount: 1 μL

Injection method: Split 50:1

Inlet temperature: 280° C.

Column oven: 190° C. (5 min)–8° C./min–250° C. (7.5 min)

Carrier gas: He, linear velocity, 35 cm/sec

Detector: FID, 300° C.

GC-MS analysis conditions are as follows.

Apparatus: Network GC System (6890N, Agilent Technologies)

Mass Selective Detector (5973, Agilent Technologies)

Column: DB-FFAP 30 m, ID 0.25 mm, film 0.25 μm (Agilent Technologies)

Injection amount: 1 μL

Injection method: Split 50:1

Inlet temperature: 280° C.

Column oven: 190° C. (5 min)–8° C./min–250° ° C. (7.5 min)

Carrier gas: He, linear velocity, 39 cm/see

MS temperature: 230° C. (ion source), 150° C. (quadrupole)

Scan range: m/z 30-350

The amounts of various fatty acids were quantified from area values of peaks obtained by GC analysis. A sample was prepared by dissolving various fatty acids in 1.4% (w/v) phosphoric acid, 75% (v/v) methanol (containing 1000 ppm tridecylic acid as an internal standard). Correction between samples was performed by comparison with a peak area value of tridecylic acid as an internal standard, and the amounts of various fatty acids per culture solution were calculated. As a result of the analysis, production of various fatty acids containing lauric acid as a main component was confirmed in Strain Nos. 1 and 2. The produced various fatty acids were identified by retention time in GC analysis and GC-MS analysis.

TABLE 25

Production amounts of various fatty acids produced by fatty acid producing strain

| | | Fatty acid (g/L) | | | | | | |
|---|---|---|---|---|---|---|---|---|
| Strain No. | Strain sp. | C12 | C12:1 | C14 | C14:1 | C16 | C16:1 | C18:1 |
| 1 | *E. coli* | 1.5 ± 0.1 | 0.2 ± 0.0 | 0.2 ± 0.0 | 0.2 ± 0.0 | ND | ND | ND |
| 2 | *P. ananatis* | 1.2 ± 0.2 | 0.2 ± 0.0 | 0.2 ± 0.0 | 0.3 ± 0.0 | 0.1 ± 0.0 | 0.1 ± 0.0 | 0.2 ± 0.0 |

ND: not detected

Example 9: Construction of N-Acylamino Acid Producing Strain

As a strain that produces an N-acylamino acid from a carbon source such as glucose, a strain in which a wild type AtGH3-6 or a mutant AtGH3-6 expression unit was introduced into each of the fatty acid producing strains constructed in Examples 6 and 7 was constructed according to the following procedure.

For a promoter PphoC_SDatc sequence (SEQ ID NO: 5), DNA synthesis was requested to Thermo Fisher Scientific, and a plasmid in which a DNA fragment containing the sequence was inserted into EcoRI and NdeI sites was purchased. A DNA fragment containing PphoC_SDatc was PCR-amplified using this plasmid as a template. PCR was performed using PrimeSTAR Max DNA Polymerase (Takara Bio Inc.) under the following conditions.

1 cycle 98° C., 30 sec 30 cycles 98° C., 10 sec

60° C., 15 sec

72° C., 5 sec 1 cycle 72° C., 5 min

4° C., hold

Primers used are as follows.

TABLE 26

| Primer for amplification of DNA fragment containing PphoC_SDatc | |
|---|---|
| Nucleotide sequence (5' to 3') | SEQ ID NO |
| CCATGATTACGAATTCATTTTTTCAATGTG | 181 |
| ATGGATTCCTCCTTACGGTGTTATATGTCC | 182 |

A DNA fragment containing a wild type or mutant AtGH3-6 gene was PCR-amplified using pET-28a-AtGH3-6 or pET-28a-AtGH3-6 ID31, pET-28a-AtGH3-6 ID49, pET-28a-AtGH3-6 ID56, or pET-28a-AtGH3-6 ID61 constructed in Example 1 (ID indicates Mutant No.) as a template. PCR was performed using PrimeSTAR Max DNA Polymerase (Takara Bio Inc.) under the following conditions.

1 cycle 98° C., 30 sec 30 cycles 98° C., 10 sec

60° C., 15 sec

72° C., 10 sec 1 cycle 72° C., 5 min

4° C., hold

Primers used are as follows.

TABLE 27

| Primers for amplification of DNA fragment containing wild type or mutant AtGH3-6 gene | |
|---|---|
| Nucleotide sequence (5' to 3') | SEQ ID NO |
| TAAGGAGGAATCCATATGCCGGAAGCACCA | 183 |
| GATCCCCGGGTACCGAGCTCCTCGAGTTAATTACT | 184 |

A PCR product containing PphoC_SDatc, a PCR product containing a wild type or mutant AtGH3-6 gene, and pHSG398 (Takara Bio Inc.) treated with EcoRI and SacI were separated from each other by agarose gel electrophoresis, then a DNA having a target size was extracted from the agarose gel, and an In-Fusion reaction was performed using In-Fusion (registered trademark) HD Cloning Kit (Takara Bio Inc.). *E. coli* JM109 was transformed with the reaction solution, and a target plasmid (plasmid containing PphoC_SDate and AtGH3-6 expression units) was extracted from a chloramphenicol resistant strain. This plasmid was defined as pHSG398-PphoC-AtGH3-6 (SDatc), pHSG398-PphoC-AtGH3-6 ID31 (SDatc), pHSG398-PphoC-AtGH3-6 ID49 (SDatc), pHSG398-PphoC-AtGH3-6 ID56 (SDatc), or pHSG398-PphoC-AtGH3-6 ID61 (SDatc). Each of the fatty acid producing strains constructed in Examples 6 and 7 (*E. coli* ΔfadD/pMW118-Ptac-UcTEopt and *P. ananatis* ΔfadD Δgcd/pMW118-PlacUV5-lacI-UcTEopt) was transformed with the obtained target plasmid and pHSG398 (negative control) to obtain a transformant having the plasmid from kanamycin and chloramphenicol resistant strains. The obtained transformant was defined as an N-acylamino acid producing strain. The strains constructed are as follows.

TABLE 28

| N-acylamino acid producing strain | | | |
|---|---|---|---|
| Strain No. | Host | Plasmid (1) | Plasmid (2) |
| 3 | *E. coli* | pMW118- | pHSG398 |
| 4 | ΔfadD | Ptac-UcTEopt | pHSG398-PphoC-AtGH3-6 (SDatc) |
| 5 | | | pHSG398-PphoC-AtGH3-6 ID31 (SDatc) |
| 6 | | | pHSG398-PphoC-AtGH3-6 ID49 (SDatc) |
| 7 | | | pHSG398-PphoC-AtGH3-6 ID56 (SDatc) |
| 8 | | | pHSG398-PphoC-AtGH3-6 ID61 (SDatc) |
| 9 | *P.* | pMW118- | pHSG398 |
| 10 | *ananatis* ΔfadD | PlacUV5-lacI- | pHSG398-PphoC-AtGH3-6 (SDatc) |
| 11 | Δged | UcTEopt | pHSG398-PphoC-AtGH3-6 ID31 (SDatc) |
| 12 | | | pHSG398-PphoC-AtGH3-6 ID49 (SDatc) |
| 13 | | | pHSG398-PphoC-AtGH3-6 ID56 (SDatc) |
| 14 | | | pHSG398-PphoC-AtGH3-6 ID61 (SDatc) |

Example 10: Synthesis of Nα-Lauroyl-L-Glutamic Acid from Glucose Using N-Acylamino Acid Producing Strain The N-acylamino acid producing strain constructed in Example 9 was inoculated into an LB agar medium containing 50 mg/L kanamycin and 25 mg/L chloramphenicol and incubated at 30° C. for 16 hours. The obtained bacterial cells were inoculated into 3 mL of an evaluation medium, and cultured by shaking using a test tube at 30° C. and 120 rpm for 48 hours. When Strain Nos. 9 to 14 were cultured, 1 mM IPTG was added to the medium. The composition of the evaluation medium is as follows.

TABLE 29

| Composition of evaluation medium of N-acylamino acid producing strain | |
|---|---|
| Raw material name | Concentration |
| D-glucose | 40 g/L |
| $MgSO_4 \cdot 7H_2O$ | 1 g/L |
| $(NH_4)_2SO_4$ | 16 g/L |
| $KH_2PO_4$ | 0.3 g/L |
| KCl | 1 g/L |
| MES | 10 g/L |
| D-pantothenic acid calcium salt | 10 mg/L |
| betaine | 1 g/L |
| Bacto ™ Tryptone | 1 g/L |
| Bacto ™ Yeast Extract | 1 g/L |
| $FeSO_4 \cdot 7H_2O$ | 10 mg/L |
| $MnSO_4 \cdot 5H_2O$ | 10 mg/L |
| L-Lys•HCl | 125 mg/L |

TABLE 29-continued

| Composition of evaluation medium of N-acylamino acid producing strain | |
|---|---|
| Raw material name | Concentration |
| L-Met | 100 mg/L |
| 2,6-diaminopimelic acid (DAP) | 100 mg/L |
| $CaCO_3$ | 30 g/L |
| kanamycin monosulfate | 50 mg/L |
| chloroamphenicol | 25 mg/L |

After completion of the culture, the culture solution was well mixed. To 100 μL of the culture solution, 900 μL of 1.4% (w/v) phosphoric acid, 75% (v/v) methanol was added, and the resulting mixture was mixed with a vortex mixer for three minutes. The supernatant obtained by centrifugation was appropriately diluted with 1.4% (w/v) phosphoric acid, 75% (v/v) methanol, and subjected to UPLC-MS analysis. UPLC-MS analysis conditions are as described in Example 5.

As a result of UPLC-MS analysis, when the negative control (pHSG398) and the wild type AtGH3-6 were expressed, various Nα-acyl-L-glutamic acids were hardly produced, but when the mutant AtGH3-6 (IDs 31, 49, 56, and 61) was expressed, it was confirmed that various Nα-acyl-L-glutamic acids were produced. In Table, Control indicates the negative control and WT indicates the wild type AtGH3-6.

TABLE 30

Production amounts of various Nα-acyl-L-glutamic acids produced by each N-acylamino acid producing strain

| Strain No. 番 号 | Strain | | Nα-acyl-L-Glu (g/L) C10 | C12 | C12:1 | C14 | C14:1 | C16 | C16:1 |
|---|---|---|---|---|---|---|---|---|---|
| 3 | *E. coli* | Control | 0.0000 | 0.0001 | 0.0000 | 0.0000 | 0.0000 | 0.0000 | 0.0000 |
| 4 | | WT | 0.0000 | 0.0001 | 0.0001 | 0.0000 | 0.0000 | 0.0000 | 0.0001 |
| 5 | | ID31 | 0.0012 | 0.1296 | 0.0682 | 0.0003 | 0.0053 | 0.0001 | 0.0003 |
| 6 | | ID49 | 0.0019 | 0.1474 | 0.0863 | 0.0009 | 0.0086 | 0.0003 | 0.0012 |
| 7 | | ID56 | 0.0036 | 0.1942 | 0.1188 | 0.0017 | 0.0211 | 0.0006 | 0.0018 |
| 8 | | ID61 | 0.0028 | 0.1745 | 0.1059 | 0.0012 | 0.0149 | 0.0003 | 0.0014 |
| 9 | *P. ananatis* | Control | 0.0000 | 0.0022 | 0.0000 | 0.0000 | 0.0000 | 0.0000 | 0.0000 |
| 10 | | WT | 0.0011 | 0.0345 | 0.0183 | 0.0007 | 0.0008 | 0.0000 | 0.0003 |
| 11 | | ID31 | 0.0073 | 0.7553 | 0.1953 | 0.0104 | 0.1003 | 0.0001 | 0.0016 |
| 12 | | ID49 | 0.0075 | 0.7029 | 0.2248 | 0.0341 | 0.1200 | 0.0008 | 0.0132 |
| 13 | | ID56 | 0.0069 | 0.7486 | 0.1905 | 0.0125 | 0.0892 | 0.0004 | 0.0054 |
| 14 | | ID61 | 0.0042 | 0.7613 | 0.1522 | 0.0143 | 0.0806 | 0.0004 | 0.0069 |

Example 11: Synthesis of Nα-Lauroyl-L-Aspartic Acid from Glucose Using N-Acylamino Acid Producing Strain The N-acylamino acid producing strain constructed in Example 9 was inoculated into an LB agar medium containing 50 mg/L kanamycin and 25 mg/L chloramphenicol and incubated at 30° C. for 16 hours. The obtained bacterial cells were inoculated into 3 mL of an evaluation medium, and cultured by shaking using a test tube at 30° C. and 120 rpm for 48 hours. When Strain Nos. 9 to 14 were cultured, 1 mM IPTG was added to the medium. For the composition of the evaluation medium, 10 g/L L-aspartic acid was added to the composition described in Example 10.

After completion of the culture, the culture solution was well mixed. To 100 μL of the culture solution, 900 μL of 1.4% (w/v) phosphoric acid, 75% (v/v) methanol was added, and the resulting mixture was mixed with a vortex mixer for three minutes. The supernatant obtained by centrifugation was appropriately diluted with 1.4% (w/v) phosphoric acid, 75% (v/v) methanol, and subjected to UPLC-MS analysis. UPLC-MS analysis was performed as described in Example 5, and SIR detection was performed as follows. For quantification of C10-L-Asp, C10-L-Asp was used as a standard sample, and for quantification of Nα-acyl-L-Asp having an acyl group having a carbon chain length of C12 or more, C12-L-Asp was used as a standard sample.

TABLE 31

| MS ion detected by SIR method | |
|---|---|
| Nα-acyl-L-Asp | $m/z^-$ |
| C10-L-Asp | 286 |
| C12-L-Asp | 314 |
| C12:1-L-Asp | 312 |
| C14-L-Asp | 342 |
| C14:1-L-Asp | 340 |
| C16-L-Asp | 370 |
| C16:1-L-Asp | 368 |

As a result of UPLC-MS analysis, in the negative control (pHSG398), various Nα-acyl-L-aspartic acids were hardly produced, but when the wild type AtGH3-6 or the mutant AtGH3-6 (IDs 31, 49, 56, and 61) was expressed, it was confirmed that various Nα-acyl-L-aspartic acid acids were produced. In Table, Control indicates the negative control and WT indicates the wild type AtGH3-6.

TABLE 32

| Production amounts of various Nα-acyl-L-aspartic acids produced by each N-acylamino acid producing strain | | | | | | | | | |
|---|---|---|---|---|---|---|---|---|---|
| Strain | | | Nα-acyl-L-Asp (g/L) | | | | | | |
| No. | Strain | | C10 | C12 | C12:1 | C14 | C14:1 | C16 | C16:1 |
| 3 | *E. coli* | Control | 0.0000 | 0.0000 | 0.0000 | 0.0000 | 0.0000 | 0.0000 | 0.0000 |
| 4 | | WT | 0.0000 | 0.0003 | 0.0001 | 0.0001 | 0.0002 | 0.0001 | 0.0008 |
| 5 | | ID31 | 0.0000 | 0.0012 | 0.0005 | 0.0000 | 0.0001 | 0.0000 | 0.0001 |
| 6 | | ID49 | 0.0001 | 0.0025 | 0.0012 | 0.0001 | 0.0003 | 0.0000 | 0.0001 |
| 7 | | ID56 | 0.0001 | 0.0007 | 0.0017 | 0.0002 | 0.0006 | 0.0000 | 0.0002 |
| 8 | | ID61 | 0.0000 | 0.0022 | 0.0008 | 0.0001 | 0.0003 | 0.0000 | 0.0001 |
| 9 | *P. ananatis* | Control | 0.0000 | 0.0001 | 0.0000 | 0.0000 | 0.0000 | 0.0000 | 0.0000 |
| 10 | | WT | 0.0087 | 0.1560 | 0.0912 | 0.0036 | 0.0566 | 0.0003 | 0.0054 |
| 11 | | ID31 | 0.0002 | 0.0816 | 0.0255 | 0.0008 | 0.0065 | 0.0001 | 0.0010 |
| 12 | | ID49 | 0.0006 | 0.1178 | 0.0341 | 0.0028 | 0.0140 | 0.0002 | 0.0042 |
| 13 | | ID56 | 0.0002 | 0.0939 | 0.0277 | 0.0015 | 0.0094 | 0.0001 | 0.0019 |
| 14 | | ID61 | 0.0006 | 0.1359 | 0.0375 | 0.0032 | 0.0171 | 0.0002 | 0.0046 |

Example 12: Evaluation of Foaming of Culture Solution of N-Acylamino Acid Producing Strain The N-acylamino acid producing strain constructed in Example 9 was inoculated into an LB agar medium containing 50 mg/L kanamycin and 25 mg/L chloramphenicol and incubated at 30° C. for 16 hours. The strains evaluated are as follows.

TABLE 33

| N-acylamino acid producing strain used for evaluation of foaming of culture solution (N-acylamino acid producing strain constructed in Example 9) | | | |
|---|---|---|---|
| Strain No. | Host | Plasmid (1) | Plasmid (2) |
| 3 | *E. coli* | pMW118- | pHSG398 |
| 4 | | Ptac- | pHSG398-PphoC-AtGH3-6 (SDatc) |
| 8 | ΔfadD | UcTEopt | pHSG398-PphoC-AtGH3-6 ID61 (SDatc) |
| 9 | *P.* | pMW118- | pHSG398 |
| 10 | *ananatis* | PlacUV5- | pHSG398-PphoC-AtGH3-6 (SDatc) |
| 14 | ΔfadD | lacI- | pHSG398-PphoC-AtGH3-6 ID61 |
| | Δgcd | UcTEopt | (SDatc) |

The obtained bacterial cells were inoculated into 50 mL of an evaluation medium, and cultured by shaking using 500 mL of Ultra Yield (trademark) Flask (THOMSON) at 30° C. and 220 rpm. When Strain Nos. 9, 10, and 14 were cultured, 1 mM IPTG was added to the medium. The composition of the evaluation medium is as described in Example 10.

After completion of the culture, the culture solution was well mixed and centrifuged to obtain a culture supernatant.

To 100 μL of the culture supernatant, 900 μL of 1.4% (w/v) phosphoric acid, 75% (v/v) methanol was added, and the resulting mixture was mixed with a vortex mixer for three minutes. The supernatant obtained by centrifugation was appropriately diluted with 1.4% (w/v) phosphoric acid, 75% (v/v) methanol, and subjected to UPLC-MS analysis. UPLC-MS analysis conditions are as described in Example 5.

As a result of UPLC-MS analysis, when the negative control (pHSG398) and the wild type AtGH3-6 were expressed, various Nα-acyl-L-glutamic acids were hardly produced, but when the mutant AtGH3-6 (ID 61) was expressed, it was confirmed that various Nα-acyl-L-glutamic acids were produced. In Table, Control indicates the negative control, WT indicates the wild type AtGH3-6, and total indicates the total concentration of Nα-acyl-L-glutamic acids of C10, C12, C12: 1, C14, C14: 1, C16, and C16: 1 each having an acyl group.

TABLE 34

| Production amounts of various Nα-acyl-L-glutamic acids produced by each N-acylamino acid producing strain in culture supernatant | | | | | | | | | | |
|---|---|---|---|---|---|---|---|---|---|---|
| Strain No. | | | Nα-acyl-L-Glu (g/L) | | | | | | | |
| 番号 | strain | | C10 | C12 | C12:1 | C14 | C14:1 | C16 | C16:1 | total |
| 3 | *E. coli* | Control | 0.000 | 0.001 | 0.000 | 0.000 | 0.000 | 0.000 | 0.000 | 0.001 |
| 4 | | WT | 0.000 | 0.001 | 0.001 | 0.000 | 0.000 | 0.000 | 0.000 | 0.002 |
| 8 | | ID61 | 0.003 | 0.094 | 0.094 | 0.001 | 0.014 | 0.000 | 0.001 | 0.205 |
| 9 | *P. ananatis* | Control | 0.000 | 0.001 | 0.000 | 0.000 | 0.000 | 0.000 | 0.000 | 0.001 |
| 10 | | WT | 0.001 | 0.009 | 0.011 | 0.000 | 0.002 | 0.000 | 0.000 | 0.024 |
| 14 | | ID61 | 0.003 | 0.672 | 0.177 | 0.032 | 0.092 | 0.001 | 0.013 | 0.990 |

In order to evaluate foaming of the obtained culture supernatants, the pH of 4 mL of each of the culture supernatants was adjusted to 5.0 with HCl, and then ultrapure water was added thereto to make the volume thereof 5 mL. As a control, a solution was prepared in which Nα-lauroyl-L-glutamic acid (AMISOFT (registered trademark) LA-D) was dissolved in ultrapure water, and the pH thereof was adjusted to 5.0 with NaOH. Furthermore, a solution was prepared in which an Nα-lauroyl-L-glutamic acid (AMISOFT (registered trademark) LA-D) solution was added to 4 mL of the culture supernatant of the negative control (pHSG398), the pH thereof was adjusted to 5.0 with HCl, and then ultrapure water was added thereto to make the volume thereof 5 mL.

2 mL of each sample was put in a screw tube (total length 105 mm, mouth inner diameter ϕ 10.0 mm, body diameter ϕ 16.5 mm) and incubated in a water bath at 35° C. for 10 minutes. Thereafter, the screw tube was held in the hand and shaken up and down for 10 seconds, and the height of foam immediately after shaking was measured.

As a result, stronger foaming was confirmed in a case where the mutant AtGH3-6 (ID 61) was expressed as compared with a case where the negative control (pHSG 398) or the wild type AtGH3-6 was expressed. Therefore, this indicates that the Nα-acyl-L-glutamic acid produced by the N-acylamino acid producing strain is available as a surfactant application. In Table, Control indicates the negative control, WT indicates the wild type AtGH3-6, and total Nα-acyl-L-Glu indicates the total concentration of Nα-acyl-L-glutamic acids of C10, C12, C12: 1, C14, C14: 1, C16, and C16: 1 each having an acyl group.

TABLE 35

Height of foam after culture supernatant of each N-acylamino acid producing strain is shaken

| Sample No. | Strain No. | Strain | | Total Nα-acyl-L-Glu (g/L) in sample | Height of foam (mm) |
|---|---|---|---|---|---|
| 1 | 3 | *E. coli* | Control | 0.00 | 1.0 ± 0.0 |
| 2 | 4 | | WT | 0.00 | 4.0 ± 0.0 |
| 3 | 8 | | ID61 | 0.16 | 16.5 ± 0.5 |
| 4 | C12-L-Glu solution (control) | | | 0.16 | 10.5 ± 2.5 |
| 5 | Sample No. 1 + C12-l-Glu solution (control) | | | 0.16 | 5.5 ± 1.5 |
| 6 | 9 | *P. ananatis* | Control | 0.00 | 4.5 ± 2.5 |
| 7 | 10 | | WT | 0.02 | 4.0 ± 2.0 |
| 8 | 14 | | ID61 | 0.79 | 33.0 ± 0.0 |
| 9 | C12-L-Glu solution (control) | | | 0.79 | 11.0 ± 1.0 |
| 10 | Sample No. 6 + C12-l-Glu solution (control) | | | 0.79 | 16.0 ± 1.0 |

INDUSTRIAL APPLICABILITY

The present invention is useful for production of an N-acyl-amino group-containing compound that can be used for a cosmetic material (particularly a surfactant) and the like.

Sequence Listing Free Text

SEQ ID NOs: 1 and 2 represent the amino acid sequence of AtGH3-6 and a nucleotide sequence encoding the amino acid sequence in which a codon is optimized for expression in *Escherichia coli*, respectively.

SEQ ID NOs: 3 and 4 represent an amino acid sequence of medium-chain acyl-ACP thioesterase (UcTE, GenBank: M94159) derived from California bay (*Umbellularia californica*) (amino acids 1 to 83 each represent a transport peptide) and a nucleotide sequence encoding an amino acid sequence in which an initiating methionine is added to amino acid residues at positions 84 to 382 in the amino acid sequence (a codon is optimized for expression in *Escherichia coli*), respectively.

SEQ ID NO: 5 represents a nucleotide sequence of PphoC_SDatc.

SEQ ID NO: 6 represents a nucleotide sequence of Ptac-RBST7-UcTEopt (nucleotides 7 to 71 each represent a Ptac promoter, nucleotides 82 to 110 each represent RBST7, and nucleotides 117 to 1019 each represent a UcTEopt gene).

SEQ ID NOs: 7 to 184 each represent a nucleotide sequence of a primer.

SEQ ID NOs: 185 and 186 represent an amino acid sequence of the mutant AtGH3-6 and a nucleotide sequence encoding the amino acid sequence in which a codon is optimized for expression in *Escherichia coli*, respectively.

SEQ ID NO: 187 represents an amino acid sequence of a transport peptide of UcTE.

The invention claimed is:

1. A modified enzyme comprising a mutation selected from the group consisting of N101S, I123T, Y134F, Y134V, L137I, V140I, S161P, V174A, Q200E, V231A, V311A, T336S, M337G, A339G, S340A, Y344A, Y344G, Y344V, K388N, E483D, C576A and combinations thereof in an amino acid sequence selected from the group consisting of:

(A) the amino acid sequence of SEQ ID NO: 1;

(B) the amino acid sequence of (A), but comprising a further mutation comprising substitution, deletion, insertion, or addition of one to thirty amino acid residues; and (C) the amino acid sequence of (A), but comprising additional mutations of one or more amino acid residues and having 95% or more identity to the amino acid sequence of (A), and wherein said modified enzyme has an N-acylation activity comprising:

(i) an N-acylation activity to L-glutamic acid and/or L-aspartic acid; and/or (ii) a substrate specificity to L-glutamic acid;

wherein the N-acylation activity is improved over a non-modified enzyme consisting of the amino acid sequence of SEQ ID NO: 1.

2. The modified enzyme according to claim 1, further comprising an additional mutation selected from the group consisting of R117P, T122S, C335S, M337A, Y344I, R350T, G379D, L390P, S455T, Q533R, and combinations thereof.

3. The modified enzyme according to claim 1, wherein the N-acylation activity is to L-glutamic acid or L-aspartic acid.

4. A method for producing an N-acyl-amino group-containing compound or a salt thereof, the method comprising:

reacting an amino group-containing compound and a carboxyl group-containing compound in the presence of the modified enzyme of claim 1.

5. The method according to claim 4, wherein the modified enzyme is a purified enzyme.

6. The method according to claim 4, wherein said reacting is performed using a transformed microorganism that produces the modified enzyme, or a treated product thereof.

7. The method according to claim 6, wherein the transformed microorganism comprises at least one of the following genetic modifications:

(1) enhancement of ability to supply a fatty acid;

(2) enhancement of ability to supply an amino acid;

(3) enhancement of ability to supply ATP; and (4) deficiency or attenuation of an N-acylamino acid degrading enzyme.

8. The method according to claim 6, wherein the amino group-containing compound and the carboxyl group-containing compound are produced in the transformed microorganism by culturing the transformed microorganism in the presence of a carbon source.

9. A method for producing an N-acyl-amino group-containing compound in which an amino group-containing compound and a carboxyl group-containing compound are bonded to each other by an amide bond, or a salt thereof, the method comprising culturing, in the presence of a carbon source, a microorganism comprising at least one of the following genetic modifications:

(1) enhancement of ability to supply a fatty acid;

(2) enhancement of ability to supply an amino acid;

(3) enhancement of ability to supply ATP; and (4) deficiency or attenuation of an N-acylamino acid degrading enzyme, and wherein said microorganism comprises an expression unit comprising a polynucleotide encoding the modified enzyme of claim 1.

10. The method according to claim 9, wherein the enhancement of ability to supply a fatty acid is:

(a) deficiency or attenuation of acyl CoA synthetase; and/or (b) enhancement of acyl-ACP thioesterase.

11. The method according to claim 10, wherein the acyl-ACP thioesterase has a thioesterase activity to lauroyl-ACP.

12. The method according to claim 10, wherein the acyl-ACP thioesterase is selected from:

(i) a protein comprising:

(i-1) the amino acid sequence of SEQ ID NO: 3 or (i-2) the amino acid sequence consisting of amino acid residues at positions 84 to 382 in the amino acid sequence of SEQ ID NO: 3;

(ii) a protein comprising an amino acid sequence comprising substitution, deletion, insertion, or addition of one or several amino acids in (ii-1) the amino acid sequence of SEQ ID NO: 3 or (ii-2) the amino acid sequence consisting of amino acid residues at positions 84 to 382 in the amino acid sequence of SEQ ID NO: 3, and having an acyl-ACP thioesterase activity; and (iii) a protein comprising an amino acid sequence having 90% or more identity to (iii-1) the amino acid sequence of SEQ ID NO: 3 or (iii-2) the amino acid sequence consisting of amino acid residues at positions 84 to 382 in the amino acid sequence of SEQ ID NO: 3, and having acyl-ACP thioesterase activity.

13. The method according to claim 9, wherein the carbon source is a saccharide.

14. The method according to claim 13, wherein the saccharide is glucose.

15. The method according to claim 9, wherein the microorganism is a bacterium belonging to the family Enterobacteriaceae.

16. The method according to claim 15, wherein the bacterium belonging to the family Enterobacteriaceae is a bacterium belonging to the genus *Escherichia* or a bacterium belonging to the genus *Pantoea*.

17. The method according to claim 16, wherein the bacterium belonging to the genus *Escherichia* is *Escherichia coli*, and the bacterium belonging to the genus *Pantoea* is *Pantoea ananatis*.

18. The method according to claim 4, wherein the carboxyl group-containing compound is a fatty acid.

19. The method according to claim 18, wherein the fatty acid is a fatty acid having 8 to 18 carbon atoms.

20. The method according to claim 18, wherein the fatty acid is a fatty acid having 12 carbon atoms.

21. The method according to claim 18, wherein the fatty acid is a saturated fatty acid.

22. The method according to claim 4, wherein the amino group-containing compound is an amino acid, and the enzyme has an N-acylation activity to the amino acid.

23. The method according to claim 22, wherein the amino acid is L-glutamic acid or L-aspartic acid.

24. The method according to claim 4, wherein the carboxyl group-containing compound is lauric acid, and the N-acyl-amino group-containing compound is No-lauroyl-L-glutamic acid or No-lauroyl-L-aspartic acid.

25. The modified enzyme according to claim 1, wherein the mutation is selected from the group consisting of N101S, 1123T, Y134F, L137I, S161P, V174A, Q200E, V231A, V311A, M337G, A339G, S340A, Y344V, K388N, C576A, and combinations thereof.

26. The modified enzyme according to claim 25, further comprising an additional mutation selected from the group consisting of R117P, T122S, Y134V, V140I, C335S, T336S, M337A, Y344A, Y344G, Y344I, R350T, G379D, L390P, S455T, E483D, Q533R, and combinations thereof.

27. The modified enzyme according to claim 1, wherein the amino acid sequence of (B) comprises substitution, deletion, insertion, or addition of one to twenty amino acids, and the amino acid of (C) comprises an amino acid sequence having 97% or more identity to the amino acid sequence shown in SEQ ID NO: 1.

* * * * *

SEQUENCE LISTING

```
<160> NUMBER OF SEQ ID NOS: 187

<210> SEQ ID NO 1
<211> LENGTH: 612
<212> TYPE: PRT
<213> ORGANISM: Arabidopsis thaliana

<400> SEQUENCE: 1

Met Pro Glu Ala Pro Lys Ile Ala Ala Leu Glu Val Ser Asp Glu Ser
1               5                   10                  15

Leu Ala Glu Lys Asn Lys Asn Lys Leu Gln Phe Ile Glu Asp Val Thr
            20                  25                  30

Thr Asn Ala Asp Asp Val Gln Arg Arg Val Leu Glu Glu Ile Leu Ser
        35                  40                  45

Arg Asn Ala Asp Val Glu Tyr Leu Lys Arg His Gly Leu Glu Gly Arg
    50                  55                  60

Thr Asp Arg Glu Thr Phe Lys His Ile Met Pro Val Val Thr Tyr Glu
65                  70                  75                  80

Asp Ile Gln Pro Glu Ile Asn Arg Ile Ala Asn Gly Asp Lys Ser Gln
```

-continued

```
                85                  90                  95

Val Leu Cys Ser Asn Pro Ile Ser Glu Phe Leu Thr Ser Ser Gly Thr
            100                 105                 110

Ser Gly Gly Glu Arg Lys Leu Met Pro Thr Ile Glu Glu Glu Leu Asp
        115                 120                 125

Arg Arg Ser Leu Leu Tyr Ser Leu Leu Met Pro Val Met Asp Gln Phe
    130                 135                 140

Val Pro Gly Leu Asp Lys Gly Lys Gly Met Tyr Phe Leu Phe Ile Lys
145                 150                 155                 160

Ser Glu Ser Lys Thr Pro Gly Gly Leu Pro Ala Arg Pro Val Leu Thr
                165                 170                 175

Ser Tyr Tyr Lys Ser Ser His Phe Lys Asn Arg Pro Tyr Asp Pro Tyr
            180                 185                 190

Thr Asn Tyr Thr Ser Pro Asn Gln Thr Ile Leu Cys Ser Asp Ser Tyr
        195                 200                 205

Gln Ser Met Tyr Ser Gln Met Leu Cys Gly Leu Cys Gln His Lys Glu
    210                 215                 220

Val Leu Arg Val Gly Ala Val Phe Ala Ser Gly Phe Ile Arg Ala Ile
225                 230                 235                 240

Lys Phe Leu Glu Lys His Trp Pro Glu Leu Ala Arg Asp Ile Arg Thr
                245                 250                 255

Gly Thr Leu Ser Ser Glu Ile Thr Asp Ser Ser Val Arg Glu Ala Val
            260                 265                 270

Gly Glu Ile Leu Lys Pro Asp Pro Lys Leu Ala Asp Phe Val Glu Ser
        275                 280                 285

Glu Cys Arg Lys Thr Ser Trp Gln Gly Ile Ile Thr Arg Leu Trp Pro
    290                 295                 300

Asn Thr Lys Tyr Val Asp Val Ile Val Thr Gly Thr Met Ser Gln Tyr
305                 310                 315                 320

Ile Pro Thr Leu Asp Tyr Tyr Ser Asn Gly Leu Pro Leu Val Cys Thr
                325                 330                 335

Met Tyr Ala Ser Ser Glu Cys Tyr Phe Gly Val Asn Leu Arg Pro Leu
            340                 345                 350

Cys Lys Pro Ser Glu Val Ser Tyr Thr Leu Ile Pro Asn Met Ala Tyr
        355                 360                 365

Phe Glu Phe Leu Pro Val His Arg Asn Ser Gly Val Thr Ser Ser Ile
    370                 375                 380

Ser Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
                405                 410                 415

Tyr Ala Gly Leu Tyr Arg Tyr Arg Val Gly Asp Val Leu Ser Val Ala
            420                 425                 430

Gly Phe Lys Asn Asn Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
                485                 490                 495

Tyr Val Leu Phe Trp Glu Leu Cys Leu Asn Gly Asn Thr Pro Ile Pro
            500                 505                 510
```

```
Pro Ser Val Phe Glu Asp Cys Cys Leu Thr Ile Glu Glu Ser Leu Asn
        515                 520                 525

Ser Val Tyr Arg Gln Gly Arg Val Ser Asp Lys Ser Ile Gly Pro Leu
    530                 535                 540

Glu Ile Lys Met Val Glu Ser Gly Thr Phe Asp Lys Leu Met Asp Tyr
545                 550                 555                 560

Ala Ile Ser Leu Gly Ala Ser Ile Asn Gln Tyr Lys Thr Pro Arg Cys
                565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Ser Pro Gly His Lys Gln
        595                 600                 605

Trp Gly Ser Asn
    610


<210> SEQ ID NO 2
<211> LENGTH: 1839
<212> TYPE: DNA
<213> ORGANISM: Arabidopsis thaliana

<400> SEQUENCE: 2

atgccggaag caccaaaaat cgcagcctta gaagtcagtg atgagagcct ggctgagaaa      60

aacaaaaaca agctgcaatt tatcgaagat gttaccacca acgctgacga tgtgcaacgt     120

cgcgttctgg aagaaattct gagtcgtaat gcggacgtag aatatctgaa acgccatggt     180

ctggaaggcc gaaccgatcg cgagaccttc aagcacatca tgccggttgt gacgtacgaa     240

gatatccaac ccgaaatcaa ccgtattgcg aatggcgaca aatcgcaggt tctgtgttcg     300

aacccgataa gcgagtttct caccagttcc ggtacctcag gcggagaacg caaacttatg     360

ccgacgatcg aggaagaact ggatcgtcgg agtctgctgt actcactcct tatgcccgtc     420

atggatcagt ttgttccggg gttagataaa gggaaaggga tgtacttcct cttcatcaag     480

tcggaatcga aaacccctgg tggtctgcct gcacgtcccg tcctgacctc gtattacaag     540

tcctctcact tcaagaatcg accttacgat ccgtatacca actataccag tccgaatcag     600

acgatcttgt gttccgactc ctaccaatcg atgtacagcc agatgctttg cggtctgtgt     660

cagcacaaag aagtgctgcg tgttggcgcg gtttttgcca gcgggtttat tcgcgcaatc     720

aaatttctgg agaaacactg gccggaattg gcgcgcgaca ttcgcacagg cactctgagc     780

agcgaaatta cggattccag cgttcgcgaa gcagtgggcg agattctgaa acccgatcct     840

aaactggcgg atttcgtcga aagtgaatgt cgcaaaacat cttggcaggg aattattacg     900

cggctatggc caaataccaa atatgttgac gtgattgtca ctggcaccat gagccagtac     960

attccgacac ttgactatta ctcgaacggc ttaccgttag tctgcacgat gtatgcgagc    1020

agtgaatgct actttggagt gaatctcagg ccactatgca aaccatctga agtatcttac    1080

acccttatcc cgaacatggc ctatttcgag ttccttccgg tccatcgtaa ctcaggcgta    1140

actagcagca ttagcttgcc taaagcactg accgaaaaag aacaacagga gttagtagat    1200

ctggtagacg tgaagctggg ccaggaatat gagttagtcg tcacaacgta tgccggtctg    1260

tatcggtatc gcgtgggtga tgtgctgagt gtagccggat tcaaaaataa tgctccgcag    1320

tttagcttta tctgccgtaa aaacgtggtt ctctccattg actctgacaa gacggatgaa    1380

gtggaattgc aaaatgctgt gaaaaacgcc gtaacgcatc tggttccgtt tgatgcctca    1440

ctgtcagaat atacctcgta tgcggatact tcttctattc caggtcatta cgtgctgttc    1500
```

-continued

```
tgggaattgt gtctgaatgg caacactccg atacctccgt ctgtgtttga ggattgctgc   1560

ttgaccattg aagagagctt aaatagcgtg tatcgccaag gccgtgtgtc cgacaaaagc   1620

attggtccac tggagatcaa gatggtggaa tcgggtactt ttgataagtt gatggattat   1680

gcgatttctt taggcgcgtc catcaaccag tacaaaacac caagatgcgt caaattcgcg   1740

ccgattatcg agctcctgaa ctcacgtgtg gttgacagct atttttcccc caaatgtccg   1800

aaatggtcac cggggcataa acagtggggt agtaattaa                          1839
```

```
<210> SEQ ID NO 3
<211> LENGTH: 382
<212> TYPE: PRT
<213> ORGANISM: Umbellularia californica

<400> SEQUENCE: 3

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
            260                 265                 270

Leu Thr Pro Arg Trp Asn Asp Leu Asp Val Asn Gln His Val Asn Asn
        275                 280                 285

Leu Lys Tyr Val Ala Trp Val Phe Glu Thr Val Pro Asp Ser Ile Phe
    290                 295                 300

Glu Ser His His Ile Ser Ser Phe Thr Leu Glu Tyr Arg Arg Glu Cys
```

-continued

```
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
            340                 345                 350

Ser Glu Val Leu Arg Ala Arg Thr Glu Trp Arg Pro Lys Leu Thr Asp
        355                 360                 365

Ser Phe Arg Gly Ile Ser Val Ile Pro Ala Glu Pro Arg Val
    370                 375                 380


<210> SEQ ID NO 4
<211> LENGTH: 903
<212> TYPE: DNA
<213> ORGANISM: Artificial sequence
<220> FEATURE:
<223> OTHER INFORMATION: codon optimization for expression in E. coli

<400> SEQUENCE: 4

atgctagagt ggaaaccgaa accgaaactg ccgcagctgt tagacgatca ctttggcttg     60

catggcttgg tctttcgccg cacgtttgcc attcgcagct atgaggtagg tcccgatcgc    120

agtacctcga ttcttgccgt tatgaaccac atgcaagaag ctaccttgaa ccatgcgaaa    180

tcagtgggca tcttagggga tgggtttggt accaccctgg aaatgtccaa acgcgacctg    240

atgtgggtgg tgcgtcgtac gcatgttgca gttgaacgtt accctacttg gggtgatacc    300

gttgaggtgg aatgctggat tggcgctagc ggcaataacg gtatgcgtcg ggatttcctt    360

gtccgggatt gtaaaaccgg ggaaattctt acccgctgta cgtcactctc agtgctgatg    420

aacacccgta ctcgtcgcct gagtaccatt ccggacgaag ttcgcggtga aattggtcca    480

gcgttcattg acaatgtggc agtcaaagat gacgagatca agaaactgca gaaactcaac    540

gattcaacgg ccgattacat ccaaggcggc ctcacgccac gctggaatga cctggatgtg    600

aatcagcacg tcaacaacct gaagtacgtt gcgtgggtct ttgaaacggt accggattcg    660

atctttgaga gccatcacat tagtagcttc accctcgaat atcgtcgtga atgtacacgc    720

gatagtgtac ttcgtagcct gaccaccgtg agtggtggtt cttcggaagc aggcttggta    780

tgcgaccatc tgctgcaact ggaaggcgga tcggaagtgc tgcgtgctcg cactgaatgg    840

cgtccgaaac tgacagatag ctttcgcgga atctcggtga ttcctgcgga acctcgcgtt    900

taa                                                                  903


<210> SEQ ID NO 5
<211> LENGTH: 98
<212> TYPE: DNA
<213> ORGANISM: Escherichia coli

<400> SEQUENCE: 5

atttttcaa tgtgatttta acttttactt ccagatgact ataatgtgac taaaaacaaa     60

accattgttc tggacatata acaccgtaag gaggaatc                             98


<210> SEQ ID NO 6
<211> LENGTH: 1025
<212> TYPE: DNA
<213> ORGANISM: Artificial sequence
<220> FEATURE:
<223> OTHER INFORMATION: plasmid

<400> SEQUENCE: 6

agatctccct gttgacaatt aatcatcggc tctataatgt gtggaatcgt gagcggataa     60
```

-continued caatttcaca caggatctag aaataatttt gtttaacttt aagaaggaga tataccatgc 120
tagagtggaa accgaaaccg aaactgccgc agctgttaga cgatcacttt ggcttgcatg 180
gcttggtctt tcgccgcacg tttgccattc gcagctatga ggtaggtccc gatcgcagta 240
cctcgattct tgccgttatg aaccacatgc aagaagctac cttgaaccat gcgaaatcag 300
tgggcatctt aggggatggg tttggtacca ccctggaaat gtccaaacgc gacctgatgt 360
gggtggtgcg tcgtacgcat gttgcagttg aacgttaccc tacttggggt gataccgttg 420
aggtggaatg ctggattggc gctagcggca ataacggtat gcgtcgggat ttccttgtcc 480
gggattgtaa aaccggggaa attcttaccc gctgtacgtc actctcagtg ctgatgaaca 540
cccgtactcg tcgcctgagt accattccgg acgaagttcg cggtgaaatt ggtccagcgt 600
tcattgacaa tgtggcagtc aaagatgacg agatcaagaa actgcagaaa ctcaacgatt 660
caacggccga ttacatccaa ggcggcctca cgccacgctg gaatgacctg gatgtgaatc 720
agcacgtcaa caacctgaag tacgttgcgt gggtctttga aacggtaccg gattcgatct 780
ttgagagcca tcacattagt agcttcaccc tcgaatatcg tcgtgaatgt acacgcgata 840
gtgtacttcg tagcctgacc accgtgagtg gtggttcttc ggaagcaggc ttggtatgcg 900
accatctgct gcaactggaa ggcggatcgg aagtgctgcg tgctcgcact gaatggcgtc 960
cgaaactgac agatagcttt cgcggaatct cggtgattcc tgcggaacct cgcgtttaag 1020
aattc 1025

<210> SEQ ID NO 7
<211> LENGTH: 33
<212> TYPE: DNA
<213> ORGANISM: Artificial sequence
<220> FEATURE:
<223> OTHER INFORMATION: primer

<400> SEQUENCE: 7
cgtcggagtc tgctgttttc actccttatg ccc 33

<210> SEQ ID NO 8
<211> LENGTH: 33
<212> TYPE: DNA
<213> ORGANISM: Artificial sequence
<220> FEATURE:
<223> OTHER INFORMATION: primer

<400> SEQUENCE: 8
gggcataagg agtgaaaaca gcagactccg acg 33

<210> SEQ ID NO 9
<211> LENGTH: 33
<212> TYPE: DNA
<213> ORGANISM: Artificial sequence
<220> FEATURE:
<223> OTHER INFORMATION: primer

<400> SEQUENCE: 9
cgtcggagtc tgctggtgtc actccttatg ccc 33

<210> SEQ ID NO 10
<211> LENGTH: 33
<212> TYPE: DNA
<213> ORGANISM: Artificial sequence
<220> FEATURE:
<223> OTHER INFORMATION: primer

<400> SEQUENCE: 10
gggcataagg agtgacacca gcagactccg acg 33

<210> SEQ ID NO 11
<211> LENGTH: 33
<212> TYPE: DNA
<213> ORGANISM: Artificial sequence
<220> FEATURE:
<223> OTHER INFORMATION: primer

<400> SEQUENCE: 11
ttcctcttca tcaagccgga atcgaaaacc cct 33

<210> SEQ ID NO 12
<211> LENGTH: 33
<212> TYPE: DNA
<213> ORGANISM: Artificial sequence
<220> FEATURE:
<223> OTHER INFORMATION: primer

<400> SEQUENCE: 12
aggggttttc gattccggct tgatgaagag gaa 33

<210> SEQ ID NO 13
<211> LENGTH: 33
<212> TYPE: DNA
<213> ORGANISM: Artificial sequence
<220> FEATURE:
<223> OTHER INFORMATION: primer

<400> SEQUENCE: 13
ctgcctgcac gtcccgcgct gacctcgtat tac 33

<210> SEQ ID NO 14
<211> LENGTH: 33
<212> TYPE: DNA
<213> ORGANISM: Artificial sequence
<220> FEATURE:
<223> OTHER INFORMATION: primer

<400> SEQUENCE: 14
gtaatacgag gtcagcgcgg gacgtgcagg cag 33

<210> SEQ ID NO 15
<211> LENGTH: 33
<212> TYPE: DNA
<213> ORGANISM: Artificial sequence
<220> FEATURE:
<223> OTHER INFORMATION: primer

<400> SEQUENCE: 15
ctgcgtgttg gcgcggcgtt tgccagcggg ttt 33

<210> SEQ ID NO 16
<211> LENGTH: 33
<212> TYPE: DNA
<213> ORGANISM: Artificial sequence
<220> FEATURE:
<223> OTHER INFORMATION: primer

<400> SEQUENCE: 16
aaacccgctg gcaaacgccg cgccaacacg cag 33

<210> SEQ ID NO 17
<211> LENGTH: 33

-continued

<212> TYPE: DNA
<213> ORGANISM: Artificial sequence
<220> FEATURE:
<223> OTHER INFORMATION: primer

<400> SEQUENCE: 17
ttaccgttag tctgcagcat gtatgcgagc agt 33

<210> SEQ ID NO 18
<211> LENGTH: 33
<212> TYPE: DNA
<213> ORGANISM: Artificial sequence
<220> FEATURE:
<223> OTHER INFORMATION: primer

<400> SEQUENCE: 18
actgctcgca tacatgctgc agactaacgg taa 33

<210> SEQ ID NO 19
<211> LENGTH: 33
<212> TYPE: DNA
<213> ORGANISM: Artificial sequence
<220> FEATURE:
<223> OTHER INFORMATION: primer

<400> SEQUENCE: 19
ccgttagtct gcacgggcta tgcgagcagt gaa 33

<210> SEQ ID NO 20
<211> LENGTH: 33
<212> TYPE: DNA
<213> ORGANISM: Artificial sequence
<220> FEATURE:
<223> OTHER INFORMATION: primer

<400> SEQUENCE: 20
ttcactgctc gcatagcccg tgcagactaa cgg 33

<210> SEQ ID NO 21
<211> LENGTH: 33
<212> TYPE: DNA
<213> ORGANISM: Artificial sequence
<220> FEATURE:
<223> OTHER INFORMATION: primer

<400> SEQUENCE: 21
gtctgcacga tgtatggcag cagtgaatgc tac 33

<210> SEQ ID NO 22
<211> LENGTH: 33
<212> TYPE: DNA
<213> ORGANISM: Artificial sequence
<220> FEATURE:
<223> OTHER INFORMATION: primer

<400> SEQUENCE: 22
gtagcattca ctgctgccat acatcgtgca gac 33

<210> SEQ ID NO 23
<211> LENGTH: 33
<212> TYPE: DNA
<213> ORGANISM: Artificial sequence
<220> FEATURE:
<223> OTHER INFORMATION: primer

<400> SEQUENCE: 23
tgcacgatgt atgcggcgag tgaatgctac ttt 33

<210> SEQ ID NO 24
<211> LENGTH: 33
<212> TYPE: DNA
<213> ORGANISM: Artificial sequence
<220> FEATURE:
<223> OTHER INFORMATION: primer

<400> SEQUENCE: 24
aaagtagcat tcactcgccg catacatcgt gca 33

<210> SEQ ID NO 25
<211> LENGTH: 33
<212> TYPE: DNA
<213> ORGANISM: Artificial sequence
<220> FEATURE:
<223> OTHER INFORMATION: primer

<400> SEQUENCE: 25
gcgagcagtg aatgcggctt tggagtgaat ctc 33

<210> SEQ ID NO 26
<211> LENGTH: 33
<212> TYPE: DNA
<213> ORGANISM: Artificial sequence
<220> FEATURE:
<223> OTHER INFORMATION: primer

<400> SEQUENCE: 26
gagattcact ccaaagccgc attcactgct cgc 33

<210> SEQ ID NO 27
<211> LENGTH: 33
<212> TYPE: DNA
<213> ORGANISM: Artificial sequence
<220> FEATURE:
<223> OTHER INFORMATION: primer

<400> SEQUENCE: 27
gcgagcagtg aatgcgcgtt tggagtgaat ctc 33

<210> SEQ ID NO 28
<211> LENGTH: 33
<212> TYPE: DNA
<213> ORGANISM: Artificial sequence
<220> FEATURE:
<223> OTHER INFORMATION: primer

<400> SEQUENCE: 28
gagattcact ccaaacgcgc attcactgct cgc 33

<210> SEQ ID NO 29
<211> LENGTH: 33
<212> TYPE: DNA
<213> ORGANISM: Artificial sequence
<220> FEATURE:
<223> OTHER INFORMATION: primer

<400> SEQUENCE: 29
gcgagcagtg aatgcgtgtt tggagtgaat ctc 33

<210> SEQ ID NO 30
<211> LENGTH: 33
<212> TYPE: DNA
<213> ORGANISM: Artificial sequence -continued
<220> FEATURE:
<223> OTHER INFORMATION: primer

<400> SEQUENCE: 30
gagattcact ccaaacacgc attcactgct cgc 33

<210> SEQ ID NO 31
<211> LENGTH: 33
<212> TYPE: DNA
<213> ORGANISM: Artificial sequence
<220> FEATURE:
<223> OTHER INFORMATION: primer

<400> SEQUENCE: 31
gttctctcca ttgacaccga caagacggat gaa 33

<210> SEQ ID NO 32
<211> LENGTH: 33
<212> TYPE: DNA
<213> ORGANISM: Artificial sequence
<220> FEATURE:
<223> OTHER INFORMATION: primer

<400> SEQUENCE: 32
ttcatccgtc ttgtcggtgt caatggagag aac 33

<210> SEQ ID NO 33
<211> LENGTH: 36
<212> TYPE: DNA
<213> ORGANISM: Artificial sequence
<220> FEATURE:
<223> OTHER INFORMATION: primer

<400> SEQUENCE: 33
cgcaaactta tgccgagcac cgaggaagaa ctggat 36

<210> SEQ ID NO 34
<211> LENGTH: 36
<212> TYPE: DNA
<213> ORGANISM: Artificial sequence
<220> FEATURE:
<223> OTHER INFORMATION: primer

<400> SEQUENCE: 34
atccagttct tcctcggtgc tcggcataag tttgcg 36

<210> SEQ ID NO 35
<211> LENGTH: 33
<212> TYPE: DNA
<213> ORGANISM: Artificial sequence
<220> FEATURE:
<223> OTHER INFORMATION: primer

<400> SEQUENCE: 35
acctcaggcg gagaaccgaa acttatgccg acg 33

<210> SEQ ID NO 36
<211> LENGTH: 33
<212> TYPE: DNA
<213> ORGANISM: Artificial sequence
<220> FEATURE:
<223> OTHER INFORMATION: primer

<400> SEQUENCE: 36
cgtcggcata agtttcggtt ctccgcctga ggt 33

-continued

<210> SEQ ID NO 37
<211> LENGTH: 33
<212> TYPE: DNA
<213> ORGANISM: Artificial sequence
<220> FEATURE:
<223> OTHER INFORMATION: primer

<400> SEQUENCE: 37
aatagcgtgt atcgccgtgg ccgtgtgtcc gac 33

<210> SEQ ID NO 38
<211> LENGTH: 33
<212> TYPE: DNA
<213> ORGANISM: Artificial sequence
<220> FEATURE:
<223> OTHER INFORMATION: primer

<400> SEQUENCE: 38
gtcggacaca cggccacggc gatacacgct att 33

<210> SEQ ID NO 39
<211> LENGTH: 33
<212> TYPE: DNA
<213> ORGANISM: Artificial sequence
<220> FEATURE:
<223> OTHER INFORMATION: primer

<400> SEQUENCE: 39
tacaaaacac caagagcggt caaattcgcg ccg 33

<210> SEQ ID NO 40
<211> LENGTH: 33
<212> TYPE: DNA
<213> ORGANISM: Artificial sequence
<220> FEATURE:
<223> OTHER INFORMATION: primer

<400> SEQUENCE: 40
cggcgcgaat ttgaccgctc ttggtgtttt gta 33

<210> SEQ ID NO 41
<211> LENGTH: 33
<212> TYPE: DNA
<213> ORGANISM: Artificial sequence
<220> FEATURE:
<223> OTHER INFORMATION: primer

<400> SEQUENCE: 41
ttcctcttca tcaagccgga atcgaaaacc cct 33

<210> SEQ ID NO 42
<211> LENGTH: 33
<212> TYPE: DNA
<213> ORGANISM: Artificial sequence
<220> FEATURE:
<223> OTHER INFORMATION: primer

<400> SEQUENCE: 42
aggggttttc gattccggct tgatgaagag gaa 33

<210> SEQ ID NO 43
<211> LENGTH: 33
<212> TYPE: DNA
<213> ORGANISM: Artificial sequence
<220> FEATURE:
<223> OTHER INFORMATION: primer -continued

<400> SEQUENCE: 43
ttcctcttca tcaagccgga atcgaaaacc cct 33

<210> SEQ ID NO 44
<211> LENGTH: 33
<212> TYPE: DNA
<213> ORGANISM: Artificial sequence
<220> FEATURE:
<223> OTHER INFORMATION: primer

<400> SEQUENCE: 44
aggggttttc gattccggct tgatgaagag gaa 33

<210> SEQ ID NO 45
<211> LENGTH: 33
<212> TYPE: DNA
<213> ORGANISM: Artificial sequence
<220> FEATURE:
<223> OTHER INFORMATION: primer

<400> SEQUENCE: 45
ttcctcttca tcaagccgga atcgaaaacc cct 33

<210> SEQ ID NO 46
<211> LENGTH: 33
<212> TYPE: DNA
<213> ORGANISM: Artificial sequence
<220> FEATURE:
<223> OTHER INFORMATION: primer

<400> SEQUENCE: 46
aggggttttc gattccggct tgatgaagag gaa 33

<210> SEQ ID NO 47
<211> LENGTH: 33
<212> TYPE: DNA
<213> ORGANISM: Artificial sequence
<220> FEATURE:
<223> OTHER INFORMATION: primer

<400> SEQUENCE: 47
ttcctcttca tcaagccgga atcgaaaacc cct 33

<210> SEQ ID NO 48
<211> LENGTH: 33
<212> TYPE: DNA
<213> ORGANISM: Artificial sequence
<220> FEATURE:
<223> OTHER INFORMATION: primer

<400> SEQUENCE: 48
aggggttttc gattccggct tgatgaagag gaa 33

<210> SEQ ID NO 49
<211> LENGTH: 33
<212> TYPE: DNA
<213> ORGANISM: Artificial sequence
<220> FEATURE:
<223> OTHER INFORMATION: primer

<400> SEQUENCE: 49
ctgcctgcac gtcccgcgct gacctcgtat tac 33

<210> SEQ ID NO 50

<211> LENGTH: 33
<212> TYPE: DNA
<213> ORGANISM: Artificial sequence
<220> FEATURE:
<223> OTHER INFORMATION: primer

<400> SEQUENCE: 50
gtaatacgag gtcagcgcgg gacgtgcagg cag 33

<210> SEQ ID NO 51
<211> LENGTH: 33
<212> TYPE: DNA
<213> ORGANISM: Artificial sequence
<220> FEATURE:
<223> OTHER INFORMATION: primer

<400> SEQUENCE: 51
ccgttagtct gcacgggcta tgcgagcagt gaa 33

<210> SEQ ID NO 52
<211> LENGTH: 33
<212> TYPE: DNA
<213> ORGANISM: Artificial sequence
<220> FEATURE:
<223> OTHER INFORMATION: primer

<400> SEQUENCE: 52
ttcactgctc gcatagcccg tgcagactaa cgg 33

<210> SEQ ID NO 53
<211> LENGTH: 33
<212> TYPE: DNA
<213> ORGANISM: Artificial sequence
<220> FEATURE:
<223> OTHER INFORMATION: primer

<400> SEQUENCE: 53
gcgagcagtg aatgcgtgtt tggagtgaat ctc 33

<210> SEQ ID NO 54
<211> LENGTH: 33
<212> TYPE: DNA
<213> ORGANISM: Artificial sequence
<220> FEATURE:
<223> OTHER INFORMATION: primer

<400> SEQUENCE: 54
gagattcact ccaaacacgc attcactgct cgc 33

<210> SEQ ID NO 55
<211> LENGTH: 33
<212> TYPE: DNA
<213> ORGANISM: Artificial sequence
<220> FEATURE:
<223> OTHER INFORMATION: primer

<400> SEQUENCE: 55
ccgttagtct gcacgggcta tgcgagcagt gaa 33

<210> SEQ ID NO 56
<211> LENGTH: 33
<212> TYPE: DNA
<213> ORGANISM: Artificial sequence
<220> FEATURE:
<223> OTHER INFORMATION: primer

<400> SEQUENCE: 56

-continued ttcactgctc gcatagcccg tgcagactaa cgg 33

<210> SEQ ID NO 57
<211> LENGTH: 33
<212> TYPE: DNA
<213> ORGANISM: Artificial sequence
<220> FEATURE:
<223> OTHER INFORMATION: primer

<400> SEQUENCE: 57
gcgagcagtg aatgcgtgtt tggagtgaat ctc 33

<210> SEQ ID NO 58
<211> LENGTH: 33
<212> TYPE: DNA
<213> ORGANISM: Artificial sequence
<220> FEATURE:
<223> OTHER INFORMATION: primer

<400> SEQUENCE: 58
gagattcact ccaaacacgc attcactgct cgc 33

<210> SEQ ID NO 59
<211> LENGTH: 33
<212> TYPE: DNA
<213> ORGANISM: Artificial sequence
<220> FEATURE:
<223> OTHER INFORMATION: primer

<400> SEQUENCE: 59
gcgagcagtg aatgcgtgtt tggagtgaat ctc 33

<210> SEQ ID NO 60
<211> LENGTH: 33
<212> TYPE: DNA
<213> ORGANISM: Artificial sequence
<220> FEATURE:
<223> OTHER INFORMATION: primer

<400> SEQUENCE: 60
gagattcact ccaaacacgc attcactgct cgc 33

<210> SEQ ID NO 61
<211> LENGTH: 33
<212> TYPE: DNA
<213> ORGANISM: Artificial sequence
<220> FEATURE:
<223> OTHER INFORMATION: primer

<400> SEQUENCE: 61
ttcctcttca tcaagccgga atcgaaaacc cct 33

<210> SEQ ID NO 62
<211> LENGTH: 33
<212> TYPE: DNA
<213> ORGANISM: Artificial sequence
<220> FEATURE:
<223> OTHER INFORMATION: primer

<400> SEQUENCE: 62
aggggttttc gattccggct tgatgaagag gaa 33

<210> SEQ ID NO 63
<211> LENGTH: 33
<212> TYPE: DNA

<213> ORGANISM: Artificial sequence
<220> FEATURE:
<223> OTHER INFORMATION: primer

<400> SEQUENCE: 63
ctgcctgcac gtcccgcgct gacctcgtat tac 33

<210> SEQ ID NO 64
<211> LENGTH: 33
<212> TYPE: DNA
<213> ORGANISM: Artificial sequence
<220> FEATURE:
<223> OTHER INFORMATION: primer

<400> SEQUENCE: 64
gtaatacgag gtcagcgcgg gacgtgcagg cag 33

<210> SEQ ID NO 65
<211> LENGTH: 33
<212> TYPE: DNA
<213> ORGANISM: Artificial sequence
<220> FEATURE:
<223> OTHER INFORMATION: primer

<400> SEQUENCE: 65
ctgcgtgttg gcgcggcgtt tgccagcggg ttt 33

<210> SEQ ID NO 66
<211> LENGTH: 33
<212> TYPE: DNA
<213> ORGANISM: Artificial sequence
<220> FEATURE:
<223> OTHER INFORMATION: primer

<400> SEQUENCE: 66
aaacccgctg gcaaacgccg cgccaacacg cag 33

<210> SEQ ID NO 67
<211> LENGTH: 33
<212> TYPE: DNA
<213> ORGANISM: Artificial sequence
<220> FEATURE:
<223> OTHER INFORMATION: primer

<400> SEQUENCE: 67
ccgttagtct gcacgggcta tgcgagcagt gaa 33

<210> SEQ ID NO 68
<211> LENGTH: 33
<212> TYPE: DNA
<213> ORGANISM: Artificial sequence
<220> FEATURE:
<223> OTHER INFORMATION: primer

<400> SEQUENCE: 68
ttcactgctc gcatagcccg tgcagactaa cgg 33

<210> SEQ ID NO 69
<211> LENGTH: 33
<212> TYPE: DNA
<213> ORGANISM: Artificial sequence
<220> FEATURE:
<223> OTHER INFORMATION: primer

<400> SEQUENCE: 69
gcgagcagtg aatgcgtgtt tggagtgaat ctc 33

<210> SEQ ID NO 70
<211> LENGTH: 33
<212> TYPE: DNA
<213> ORGANISM: Artificial sequence
<220> FEATURE:
<223> OTHER INFORMATION: primer

<400> SEQUENCE: 70
gagattcact ccaaacacgc attcactgct cgc 33

<210> SEQ ID NO 71
<211> LENGTH: 27
<212> TYPE: DNA
<213> ORGANISM: Artificial sequence
<220> FEATURE:
<223> OTHER INFORMATION: primer

<400> SEQUENCE: 71
gaatgcattt ttggagtgaa tctcagg 27

<210> SEQ ID NO 72
<211> LENGTH: 27
<212> TYPE: DNA
<213> ORGANISM: Artificial sequence
<220> FEATURE:
<223> OTHER INFORMATION: primer

<400> SEQUENCE: 72
tccaaaaatg cattcactgc tcgcata 27

<210> SEQ ID NO 73
<211> LENGTH: 33
<212> TYPE: DNA
<213> ORGANISM: Artificial sequence
<220> FEATURE:
<223> OTHER INFORMATION: primer

<400> SEQUENCE: 73
ctgcgtgttg gcgcggcgtt tgccagcggg ttt 33

<210> SEQ ID NO 74
<211> LENGTH: 33
<212> TYPE: DNA
<213> ORGANISM: Artificial sequence
<220> FEATURE:
<223> OTHER INFORMATION: primer

<400> SEQUENCE: 74
aaacccgctg gcaaacgccg cgccaacacg cag 33

<210> SEQ ID NO 75
<211> LENGTH: 33
<212> TYPE: DNA
<213> ORGANISM: Artificial sequence
<220> FEATURE:
<223> OTHER INFORMATION: primer

<400> SEQUENCE: 75
gcgagcagtg aatgcgtgtt tggagtgaat ctc 33

<210> SEQ ID NO 76
<211> LENGTH: 33
<212> TYPE: DNA
<213> ORGANISM: Artificial sequence
<220> FEATURE:

-continued

<223> OTHER INFORMATION: primer

<400> SEQUENCE: 76
gagattcact ccaaacacgc attcactgct cgc 33

<210> SEQ ID NO 77
<211> LENGTH: 33
<212> TYPE: DNA
<213> ORGANISM: Artificial sequence
<220> FEATURE:
<223> OTHER INFORMATION: primer

<400> SEQUENCE: 77
gcgagcagtg aatgcgtgtt tggagtgaat ctc 33

<210> SEQ ID NO 78
<211> LENGTH: 33
<212> TYPE: DNA
<213> ORGANISM: Artificial sequence
<220> FEATURE:
<223> OTHER INFORMATION: primer

<400> SEQUENCE: 78
gagattcact ccaaacacgc attcactgct cgc 33

<210> SEQ ID NO 79
<211> LENGTH: 33
<212> TYPE: DNA
<213> ORGANISM: Artificial sequence
<220> FEATURE:
<223> OTHER INFORMATION: primer

<400> SEQUENCE: 79
gtccatcgta actcagacgt aactagcagc att 33

<210> SEQ ID NO 80
<211> LENGTH: 33
<212> TYPE: DNA
<213> ORGANISM: Artificial sequence
<220> FEATURE:
<223> OTHER INFORMATION: primer

<400> SEQUENCE: 80
aatgctgcta gttacgtctg agttacgatg gac 33

<210> SEQ ID NO 81
<211> LENGTH: 33
<212> TYPE: DNA
<213> ORGANISM: Artificial sequence
<220> FEATURE:
<223> OTHER INFORMATION: primer

<400> SEQUENCE: 81
tttggagtga atctcacgcc actatgcaaa cca 33

<210> SEQ ID NO 82
<211> LENGTH: 33
<212> TYPE: DNA
<213> ORGANISM: Artificial sequence
<220> FEATURE:
<223> OTHER INFORMATION: primer

<400> SEQUENCE: 82
tggtttgcat agtggcgtga gattcactcc aaa 33

<210> SEQ ID NO 83
<211> LENGTH: 33
<212> TYPE: DNA
<213> ORGANISM: Artificial sequence
<220> FEATURE:
<223> OTHER INFORMATION: primer

<400> SEQUENCE: 83
accaaatatg ttgacgcgat tgtcactggc acc 33

<210> SEQ ID NO 84
<211> LENGTH: 33
<212> TYPE: DNA
<213> ORGANISM: Artificial sequence
<220> FEATURE:
<223> OTHER INFORMATION: primer

<400> SEQUENCE: 84
ggtgccagtg acaatcgcgt caacatattt ggt 33

<210> SEQ ID NO 85
<211> LENGTH: 33
<212> TYPE: DNA
<213> ORGANISM: Artificial sequence
<220> FEATURE:
<223> OTHER INFORMATION: primer

<400> SEQUENCE: 85
ctgctgtact cactcattat gcccgtcatg gat 33

<210> SEQ ID NO 86
<211> LENGTH: 33
<212> TYPE: DNA
<213> ORGANISM: Artificial sequence
<220> FEATURE:
<223> OTHER INFORMATION: primer

<400> SEQUENCE: 86
atccatgacg ggcataatga gtgagtacag cag 33

<210> SEQ ID NO 87
<211> LENGTH: 33
<212> TYPE: DNA
<213> ORGANISM: Artificial sequence
<220> FEATURE:
<223> OTHER INFORMATION: primer

<400> SEQUENCE: 87
tataccagtc cgaatgagac gatcttgtgt tcc 33

<210> SEQ ID NO 88
<211> LENGTH: 33
<212> TYPE: DNA
<213> ORGANISM: Artificial sequence
<220> FEATURE:
<223> OTHER INFORMATION: primer

<400> SEQUENCE: 88
ggaacacaag atcgtctcat tcggactggt ata 33

<210> SEQ ID NO 89
<211> LENGTH: 33
<212> TYPE: DNA
<213> ORGANISM: Artificial sequence
<220> FEATURE:
<223> OTHER INFORMATION: primer -continued

<400> SEQUENCE: 89
aaacttatgc cgacgaccga ggaagaactg gat 33

<210> SEQ ID NO 90
<211> LENGTH: 33
<212> TYPE: DNA
<213> ORGANISM: Artificial sequence
<220> FEATURE:
<223> OTHER INFORMATION: primer

<400> SEQUENCE: 90
atccagttct tcctcggtcg tcggcataag ttt 33

<210> SEQ ID NO 91
<211> LENGTH: 33
<212> TYPE: DNA
<213> ORGANISM: Artificial sequence
<220> FEATURE:
<223> OTHER INFORMATION: primer

<400> SEQUENCE: 91
caggttctgt gttcgagccc gataagcgag ttt 33

<210> SEQ ID NO 92
<211> LENGTH: 33
<212> TYPE: DNA
<213> ORGANISM: Artificial sequence
<220> FEATURE:
<223> OTHER INFORMATION: primer

<400> SEQUENCE: 92
aaactcgctt atcgggctcg aacacagaac ctg 33

<210> SEQ ID NO 93
<211> LENGTH: 33
<212> TYPE: DNA
<213> ORGANISM: Artificial sequence
<220> FEATURE:
<223> OTHER INFORMATION: primer

<400> SEQUENCE: 93
aaacttatgc cgacgaccga ggaagaactg gat 33

<210> SEQ ID NO 94
<211> LENGTH: 33
<212> TYPE: DNA
<213> ORGANISM: Artificial sequence
<220> FEATURE:
<223> OTHER INFORMATION: primer

<400> SEQUENCE: 94
atccagttct tcctcggtcg tcggcataag ttt 33

<210> SEQ ID NO 95
<211> LENGTH: 33
<212> TYPE: DNA
<213> ORGANISM: Artificial sequence
<220> FEATURE:
<223> OTHER INFORMATION: primer

<400> SEQUENCE: 95
caggttctgt gttcgagccc gataagcgag ttt 33

<210> SEQ ID NO 96
<211> LENGTH: 33

-continued

<212> TYPE: DNA
<213> ORGANISM: Artificial sequence
<220> FEATURE:
<223> OTHER INFORMATION: primer

<400> SEQUENCE: 96
aaactcgctt atcgggctcg aacacagaac ctg 33

<210> SEQ ID NO 97
<211> LENGTH: 33
<212> TYPE: DNA
<213> ORGANISM: Artificial sequence
<220> FEATURE:
<223> OTHER INFORMATION: primer

<400> SEQUENCE: 97
caggttctgt gttcgagccc gataagcgag ttt 33

<210> SEQ ID NO 98
<211> LENGTH: 33
<212> TYPE: DNA
<213> ORGANISM: Artificial sequence
<220> FEATURE:
<223> OTHER INFORMATION: primer

<400> SEQUENCE: 98
aaactcgctt atcgggctcg aacacagaac ctg 33

<210> SEQ ID NO 99
<211> LENGTH: 33
<212> TYPE: DNA
<213> ORGANISM: Artificial sequence
<220> FEATURE:
<223> OTHER INFORMATION: primer

<400> SEQUENCE: 99
tataccagtc cgaatgagac gatcttgtgt tcc 33

<210> SEQ ID NO 100
<211> LENGTH: 33
<212> TYPE: DNA
<213> ORGANISM: Artificial sequence
<220> FEATURE:
<223> OTHER INFORMATION: primer

<400> SEQUENCE: 100
ggaacacaag atcgtctcat tcggactggt ata 33

<210> SEQ ID NO 101
<211> LENGTH: 33
<212> TYPE: DNA
<213> ORGANISM: Artificial sequence
<220> FEATURE:
<223> OTHER INFORMATION: primer

<400> SEQUENCE: 101
aaacttatgc cgacgaccga ggaagaactg gat 33

<210> SEQ ID NO 102
<211> LENGTH: 33
<212> TYPE: DNA
<213> ORGANISM: Artificial sequence
<220> FEATURE:
<223> OTHER INFORMATION: primer

<400> SEQUENCE: 102

-continued atccagttct tcctcggtcg tcggcataag ttt 33

<210> SEQ ID NO 103
<211> LENGTH: 33
<212> TYPE: DNA
<213> ORGANISM: Artificial sequence
<220> FEATURE:
<223> OTHER INFORMATION: primer

<400> SEQUENCE: 103
caggttctgt gttcgagccc gataagcgag ttt 33

<210> SEQ ID NO 104
<211> LENGTH: 33
<212> TYPE: DNA
<213> ORGANISM: Artificial sequence
<220> FEATURE:
<223> OTHER INFORMATION: primer

<400> SEQUENCE: 104
aaactcgctt atcgggctcg aacacagaac ctg 33

<210> SEQ ID NO 105
<211> LENGTH: 33
<212> TYPE: DNA
<213> ORGANISM: Artificial sequence
<220> FEATURE:
<223> OTHER INFORMATION: primer

<400> SEQUENCE: 105
caggttctgt gttcgagccc gataagcgag ttt 33

<210> SEQ ID NO 106
<211> LENGTH: 33
<212> TYPE: DNA
<213> ORGANISM: Artificial sequence
<220> FEATURE:
<223> OTHER INFORMATION: primer

<400> SEQUENCE: 106
aaactcgctt atcgggctcg aacacagaac ctg 33

<210> SEQ ID NO 107
<211> LENGTH: 33
<212> TYPE: DNA
<213> ORGANISM: Artificial sequence
<220> FEATURE:
<223> OTHER INFORMATION: primer

<400> SEQUENCE: 107
tataccagtc cgaatgagac gatcttgtgt tcc 33

<210> SEQ ID NO 108
<211> LENGTH: 33
<212> TYPE: DNA
<213> ORGANISM: Artificial sequence
<220> FEATURE:
<223> OTHER INFORMATION: primer

<400> SEQUENCE: 108
ggaacacaag atcgtctcat tcggactggt ata 33

<210> SEQ ID NO 109
<211> LENGTH: 33
<212> TYPE: DNA
<213> ORGANISM: Artificial sequence
<220> FEATURE:
<223> OTHER INFORMATION: primer

<400> SEQUENCE: 109
tacaaaacac caagagcggt caaattcgcg ccg 33

<210> SEQ ID NO 110
<211> LENGTH: 33
<212> TYPE: DNA
<213> ORGANISM: Artificial sequence
<220> FEATURE:
<223> OTHER INFORMATION: primer

<400> SEQUENCE: 110
cggcgcgaat ttgaccgctc ttggtgtttt gta 33

<210> SEQ ID NO 111
<211> LENGTH: 33
<212> TYPE: DNA
<213> ORGANISM: Artificial sequence
<220> FEATURE:
<223> OTHER INFORMATION: primer

<400> SEQUENCE: 111
ttcctcttca tcaagccgga atcgaaaacc cct 33

<210> SEQ ID NO 112
<211> LENGTH: 33
<212> TYPE: DNA
<213> ORGANISM: Artificial sequence
<220> FEATURE:
<223> OTHER INFORMATION: primer

<400> SEQUENCE: 112
aggggttttc gattccggct tgatgaagag gaa 33

<210> SEQ ID NO 113
<211> LENGTH: 33
<212> TYPE: DNA
<213> ORGANISM: Artificial sequence
<220> FEATURE:
<223> OTHER INFORMATION: primer

<400> SEQUENCE: 113
ttcctcttca tcaagccgga atcgaaaacc cct 33

<210> SEQ ID NO 114
<211> LENGTH: 33
<212> TYPE: DNA
<213> ORGANISM: Artificial sequence
<220> FEATURE:
<223> OTHER INFORMATION: primer

<400> SEQUENCE: 114
aggggttttc gattccggct tgatgaagag gaa 33

<210> SEQ ID NO 115
<211> LENGTH: 33
<212> TYPE: DNA
<213> ORGANISM: Artificial sequence
<220> FEATURE:
<223> OTHER INFORMATION: primer

<400> SEQUENCE: 115
ttcctcttca tcaagccgga atcgaaaacc cct 33

<210> SEQ ID NO 116
<211> LENGTH: 33
<212> TYPE: DNA
<213> ORGANISM: Artificial sequence
<220> FEATURE:
<223> OTHER INFORMATION: primer

<400> SEQUENCE: 116
aggggttttc gattccggct tgatgaagag gaa 33

<210> SEQ ID NO 117
<211> LENGTH: 33
<212> TYPE: DNA
<213> ORGANISM: Artificial sequence
<220> FEATURE:
<223> OTHER INFORMATION: primer

<400> SEQUENCE: 117
ccgttagtct gcacgggcta tgcgagcagt gaa 33

<210> SEQ ID NO 118
<211> LENGTH: 33
<212> TYPE: DNA
<213> ORGANISM: Artificial sequence
<220> FEATURE:
<223> OTHER INFORMATION: primer

<400> SEQUENCE: 118
ttcactgctc gcatagcccg tgcagactaa cgg 33

<210> SEQ ID NO 119
<211> LENGTH: 33
<212> TYPE: DNA
<213> ORGANISM: Artificial sequence
<220> FEATURE:
<223> OTHER INFORMATION: primer

<400> SEQUENCE: 119
ccgttagtct gcacgggcta tgcgagcagt gaa 33

<210> SEQ ID NO 120
<211> LENGTH: 33
<212> TYPE: DNA
<213> ORGANISM: Artificial sequence
<220> FEATURE:
<223> OTHER INFORMATION: primer

<400> SEQUENCE: 120
ttcactgctc gcatagcccg tgcagactaa cgg 33

<210> SEQ ID NO 121
<211> LENGTH: 23
<212> TYPE: DNA
<213> ORGANISM: Artificial sequence
<220> FEATURE:
<223> OTHER INFORMATION: primer

<400> SEQUENCE: 121
tagcttgcct aatgcactga ccg 23

<210> SEQ ID NO 122
<211> LENGTH: 23
<212> TYPE: DNA
<213> ORGANISM: Artificial sequence
<220> FEATURE:
<223> OTHER INFORMATION: primer -continued

<400> SEQUENCE: 122
cggtcagtgc attaggcaag cta 23

<210> SEQ ID NO 123
<211> LENGTH: 33
<212> TYPE: DNA
<213> ORGANISM: Artificial sequence
<220> FEATURE:
<223> OTHER INFORMATION: primer

<400> SEQUENCE: 123
tacaaaacac caagagcggt caaattcgcg ccg 33

<210> SEQ ID NO 124
<211> LENGTH: 33
<212> TYPE: DNA
<213> ORGANISM: Artificial sequence
<220> FEATURE:
<223> OTHER INFORMATION: primer

<400> SEQUENCE: 124
cggcgcgaat ttgaccgctc ttggtgtttt gta 33

<210> SEQ ID NO 125
<211> LENGTH: 23
<212> TYPE: DNA
<213> ORGANISM: Artificial sequence
<220> FEATURE:
<223> OTHER INFORMATION: primer

<400> SEQUENCE: 125
tagcttgcct aatgcactga ccg 23

<210> SEQ ID NO 126
<211> LENGTH: 23
<212> TYPE: DNA
<213> ORGANISM: Artificial sequence
<220> FEATURE:
<223> OTHER INFORMATION: primer

<400> SEQUENCE: 126
cggtcagtgc attaggcaag cta 23

<210> SEQ ID NO 127
<211> LENGTH: 33
<212> TYPE: DNA
<213> ORGANISM: Artificial sequence
<220> FEATURE:
<223> OTHER INFORMATION: primer

<400> SEQUENCE: 127
caggttctgt gttcgagccc gataagcgag ttt 33

<210> SEQ ID NO 128
<211> LENGTH: 33
<212> TYPE: DNA
<213> ORGANISM: Artificial sequence
<220> FEATURE:
<223> OTHER INFORMATION: primer

<400> SEQUENCE: 128
aaactcgctt atcgggctcg aacacagaac ctg 33

<210> SEQ ID NO 129

-continued

<211> LENGTH: 33
<212> TYPE: DNA
<213> ORGANISM: Artificial sequence
<220> FEATURE:
<223> OTHER INFORMATION: primer

<400> SEQUENCE: 129
tataccagtc cgaatgagac gatcttgtgt tcc 33

<210> SEQ ID NO 130
<211> LENGTH: 33
<212> TYPE: DNA
<213> ORGANISM: Artificial sequence
<220> FEATURE:
<223> OTHER INFORMATION: primer

<400> SEQUENCE: 130
ggaacacaag atcgtctcat tcggactggt ata 33

<210> SEQ ID NO 131
<211> LENGTH: 28
<212> TYPE: DNA
<213> ORGANISM: Artificial sequence
<220> FEATURE:
<223> OTHER INFORMATION: primer

<400> SEQUENCE: 131
cgacgaccga ggaagaactg gatcgtcg 28

<210> SEQ ID NO 132
<211> LENGTH: 28
<212> TYPE: DNA
<213> ORGANISM: Artificial sequence
<220> FEATURE:
<223> OTHER INFORMATION: primer

<400> SEQUENCE: 132
tcagtgcatt aggcaagcta atgctgct 28

<210> SEQ ID NO 133
<211> LENGTH: 28
<212> TYPE: DNA
<213> ORGANISM: Artificial sequence
<220> FEATURE:
<223> OTHER INFORMATION: primer

<400> SEQUENCE: 133
tgcctaatgc actgaccgaa aaagaaca 28

<210> SEQ ID NO 134
<211> LENGTH: 28
<212> TYPE: DNA
<213> ORGANISM: Artificial sequence
<220> FEATURE:
<223> OTHER INFORMATION: primer

<400> SEQUENCE: 134
cttcctcggt cgtcggcata agtttgcg 28

<210> SEQ ID NO 135
<211> LENGTH: 28
<212> TYPE: DNA
<213> ORGANISM: Artificial sequence
<220> FEATURE:
<223> OTHER INFORMATION: primer

<400> SEQUENCE: 135
gttcgagccc gataagcgag tttctcac 28

<210> SEQ ID NO 136
<211> LENGTH: 28
<212> TYPE: DNA
<213> ORGANISM: Artificial sequence
<220> FEATURE:
<223> OTHER INFORMATION: primer

<400> SEQUENCE: 136
agatcgtctc attcggactg gtatagtt 28

<210> SEQ ID NO 137
<211> LENGTH: 28
<212> TYPE: DNA
<213> ORGANISM: Artificial sequence
<220> FEATURE:
<223> OTHER INFORMATION: primer

<400> SEQUENCE: 137
cgaatgagac gatcttgtgt tccgactc 28

<210> SEQ ID NO 138
<211> LENGTH: 28
<212> TYPE: DNA
<213> ORGANISM: Artificial sequence
<220> FEATURE:
<223> OTHER INFORMATION: primer

<400> SEQUENCE: 138
ttatcgggct cgaacacaga acctgcga 28

<210> SEQ ID NO 139
<211> LENGTH: 28
<212> TYPE: DNA
<213> ORGANISM: Artificial sequence
<220> FEATURE:
<223> OTHER INFORMATION: primer

<400> SEQUENCE: 139
gttcgagccc gataagcgag tttctcac 28

<210> SEQ ID NO 140
<211> LENGTH: 28
<212> TYPE: DNA
<213> ORGANISM: Artificial sequence
<220> FEATURE:
<223> OTHER INFORMATION: primer

<400> SEQUENCE: 140
tcagtgcatt aggcaagcta atgctgct 28

<210> SEQ ID NO 141
<211> LENGTH: 28
<212> TYPE: DNA
<213> ORGANISM: Artificial sequence
<220> FEATURE:
<223> OTHER INFORMATION: primer

<400> SEQUENCE: 141
tgcctaatgc actgaccgaa aaagaaca 28

<210> SEQ ID NO 142
<211> LENGTH: 28
<212> TYPE: DNA

<213> ORGANISM: Artificial sequence
<220> FEATURE:
<223> OTHER INFORMATION: primer

<400> SEQUENCE: 142
ttatcgggct cgaacacaga acctgcga 28

<210> SEQ ID NO 143
<211> LENGTH: 28
<212> TYPE: DNA
<213> ORGANISM: Artificial sequence
<220> FEATURE:
<223> OTHER INFORMATION: primer

<400> SEQUENCE: 143
cgaatgagac gatcttgtgt tccgactc 28

<210> SEQ ID NO 144
<211> LENGTH: 28
<212> TYPE: DNA
<213> ORGANISM: Artificial sequence
<220> FEATURE:
<223> OTHER INFORMATION: primer

<400> SEQUENCE: 144
tcagtgcatt aggcaagcta atgctgct 28

<210> SEQ ID NO 145
<211> LENGTH: 28
<212> TYPE: DNA
<213> ORGANISM: Artificial sequence
<220> FEATURE:
<223> OTHER INFORMATION: primer

<400> SEQUENCE: 145
tgcctaatgc actgaccgaa aaagaaca 28

<210> SEQ ID NO 146
<211> LENGTH: 28
<212> TYPE: DNA
<213> ORGANISM: Artificial sequence
<220> FEATURE:
<223> OTHER INFORMATION: primer

<400> SEQUENCE: 146
agatcgtctc attcggactg gtatagtt 28

<210> SEQ ID NO 147
<211> LENGTH: 28
<212> TYPE: DNA
<213> ORGANISM: Artificial sequence
<220> FEATURE:
<223> OTHER INFORMATION: primer

<400> SEQUENCE: 147
gttcgagccc gataagcgag tttctcac 28

<210> SEQ ID NO 148
<211> LENGTH: 28
<212> TYPE: DNA
<213> ORGANISM: Artificial sequence
<220> FEATURE:
<223> OTHER INFORMATION: primer

<400> SEQUENCE: 148
agatcgtctc attcggactg gtatagtt 28

<210> SEQ ID NO 149
<211> LENGTH: 28
<212> TYPE: DNA
<213> ORGANISM: Artificial sequence
<220> FEATURE:
<223> OTHER INFORMATION: primer

<400> SEQUENCE: 149
cgaatgagac gatcttgtgt tccgactc 28

<210> SEQ ID NO 150
<211> LENGTH: 28
<212> TYPE: DNA
<213> ORGANISM: Artificial sequence
<220> FEATURE:
<223> OTHER INFORMATION: primer

<400> SEQUENCE: 150
tcagtgcatt aggcaagcta atgctgct 28

<210> SEQ ID NO 151
<211> LENGTH: 28
<212> TYPE: DNA
<213> ORGANISM: Artificial sequence
<220> FEATURE:
<223> OTHER INFORMATION: primer

<400> SEQUENCE: 151
tgcctaatgc actgaccgaa aaagaaca 28

<210> SEQ ID NO 152
<211> LENGTH: 28
<212> TYPE: DNA
<213> ORGANISM: Artificial sequence
<220> FEATURE:
<223> OTHER INFORMATION: primer

<400> SEQUENCE: 152
ttatcgggct cgaacacaga acctgcga 28

<210> SEQ ID NO 153
<211> LENGTH: 20
<212> TYPE: DNA
<213> ORGANISM: Artificial sequence
<220> FEATURE:
<223> OTHER INFORMATION: primer

<400> SEQUENCE: 153
taatacgact cactataggg 20

<210> SEQ ID NO 154
<211> LENGTH: 21
<212> TYPE: DNA
<213> ORGANISM: Artificial sequence
<220> FEATURE:
<223> OTHER INFORMATION: primer

<400> SEQUENCE: 154
atgctagtta ttgctcagcg g 21

<210> SEQ ID NO 155
<211> LENGTH: 56
<212> TYPE: DNA
<213> ORGANISM: Artificial sequence
<220> FEATURE:

-continued

<223> OTHER INFORMATION: primer

<400> SEQUENCE: 155
tctgatctag atagggataa cagggtaatc aaccaattaa ccaattctga ttagaa 56

<210> SEQ ID NO 156
<211> LENGTH: 40
<212> TYPE: DNA
<213> ORGANISM: Artificial sequence
<220> FEATURE:
<223> OTHER INFORMATION: primer

<400> SEQUENCE: 156
ggaaaggatc cgcggccgcc acgttgtgtc tcaaaatctc 40

<210> SEQ ID NO 157
<211> LENGTH: 70
<212> TYPE: DNA
<213> ORGANISM: Artificial sequence
<220> FEATURE:
<223> OTHER INFORMATION: primer

<400> SEQUENCE: 157 tttttctag aaataatttt gtttaacttt aagaaggaga tataccatgc tagagtggaa 60
accgaaaccg 70

<210> SEQ ID NO 158
<211> LENGTH: 36
<212> TYPE: DNA
<213> ORGANISM: Artificial sequence
<220> FEATURE:
<223> OTHER INFORMATION: primer

<400> SEQUENCE: 158
tttttggatc ctcgagttaa acgcgaggtt ccgcag 36

<210> SEQ ID NO 159
<211> LENGTH: 34
<212> TYPE: DNA
<213> ORGANISM: Artificial sequence
<220> FEATURE:
<223> OTHER INFORMATION: primer

<400> SEQUENCE: 159
tttttagatc tccctgttga caattaatca tcgg 34

<210> SEQ ID NO 160
<211> LENGTH: 34
<212> TYPE: DNA
<213> ORGANISM: Artificial sequence
<220> FEATURE:
<223> OTHER INFORMATION: primer

<400> SEQUENCE: 160
ctgtttctag atcctgtgtg aaattgttat ccgc 34

<210> SEQ ID NO 161
<211> LENGTH: 34
<212> TYPE: DNA
<213> ORGANISM: Artificial sequence
<220> FEATURE:
<223> OTHER INFORMATION: primer

<400> SEQUENCE: 161
tttttagatc tccctgttga caattaatca tcgg 34

-continued

<210> SEQ ID NO 162
<211> LENGTH: 58
<212> TYPE: DNA
<213> ORGANISM: Artificial sequence
<220> FEATURE:
<223> OTHER INFORMATION: primer

<400> SEQUENCE: 162
tttttgaatt cgagctcggt accaataatt ttgtttaact ttaagaagga gatatacc 58

<210> SEQ ID NO 163
<211> LENGTH: 68
<212> TYPE: DNA
<213> ORGANISM: Artificial sequence
<220> FEATURE:
<223> OTHER INFORMATION: primer

<400> SEQUENCE: 163
tgagctgacg gcggcaaaaa gtcaccagtg actcttcggt tgaagcctgc ttttttatac 60
taagttgg 68

<210> SEQ ID NO 164
<211> LENGTH: 68
<212> TYPE: DNA
<213> ORGANISM: Artificial sequence
<220> FEATURE:
<223> OTHER INFORMATION: primer

<400> SEQUENCE: 164
caacctgcgt ttgtgaatat gggggaggta atgaccttcc cgctcaagtt agtataaaaa 60
agctgaac 68

<210> SEQ ID NO 165
<211> LENGTH: 20
<212> TYPE: DNA
<213> ORGANISM: Artificial sequence
<220> FEATURE:
<223> OTHER INFORMATION: primer

<400> SEQUENCE: 165
tgcgatgacg acgaacacgc 20

<210> SEQ ID NO 166
<211> LENGTH: 21
<212> TYPE: DNA
<213> ORGANISM: Artificial sequence
<220> FEATURE:
<223> OTHER INFORMATION: primer

<400> SEQUENCE: 166
gattaaccgg cgtctgacga c 21

<210> SEQ ID NO 167
<211> LENGTH: 20
<212> TYPE: DNA
<213> ORGANISM: Artificial sequence
<220> FEATURE:
<223> OTHER INFORMATION: primer

<400> SEQUENCE: 167
tgcgatgacg acgaacacgc 20

<210> SEQ ID NO 168

<211> LENGTH: 21
<212> TYPE: DNA
<213> ORGANISM: Artificial sequence
<220> FEATURE:
<223> OTHER INFORMATION: primer

<400> SEQUENCE: 168
gattaaccgg cgtctgacga c 21

<210> SEQ ID NO 169
<211> LENGTH: 36
<212> TYPE: DNA
<213> ORGANISM: Artificial sequence
<220> FEATURE:
<223> OTHER INFORMATION: primer

<400> SEQUENCE: 169
tttttggatc ctcgagttaa acgcgaggtt ccgcag 36

<210> SEQ ID NO 170
<211> LENGTH: 37
<212> TYPE: DNA
<213> ORGANISM: Artificial sequence
<220> FEATURE:
<223> OTHER INFORMATION: primer

<400> SEQUENCE: 170
tttttgagct cgaattctta aacgcgaggt tccgcag 37

<210> SEQ ID NO 171
<211> LENGTH: 68
<212> TYPE: DNA
<213> ORGANISM: Artificial sequence
<220> FEATURE:
<223> OTHER INFORMATION: primer

<400> SEQUENCE: 171
ctgacgacga cagtgatcga gcagctcttc tttggtcagc tgaagcctgc ttttttatac 60
taagttgg 68

<210> SEQ ID NO 172
<211> LENGTH: 68
<212> TYPE: DNA
<213> ORGANISM: Artificial sequence
<220> FEATURE:
<223> OTHER INFORMATION: primer

<400> SEQUENCE: 172
ctctggttga tctgtttgag caggccgttt cccgttacgc cgctcaagtt agtataaaaa 60
agctgaac 68

<210> SEQ ID NO 173
<211> LENGTH: 20
<212> TYPE: DNA
<213> ORGANISM: Artificial sequence
<220> FEATURE:
<223> OTHER INFORMATION: primer

<400> SEQUENCE: 173
caaatgcgat tgtcgaggcg 20

<210> SEQ ID NO 174
<211> LENGTH: 20
<212> TYPE: DNA
<213> ORGANISM: Artificial sequence
<220> FEATURE:
<223> OTHER INFORMATION: primer

<400> SEQUENCE: 174
ccggcgttca acctgaatcc 20

<210> SEQ ID NO 175
<211> LENGTH: 20
<212> TYPE: DNA
<213> ORGANISM: Artificial sequence
<220> FEATURE:
<223> OTHER INFORMATION: primer

<400> SEQUENCE: 175
caaatgcgat tgtcgaggcg 20

<210> SEQ ID NO 176
<211> LENGTH: 20
<212> TYPE: DNA
<213> ORGANISM: Artificial sequence
<220> FEATURE:
<223> OTHER INFORMATION: primer

<400> SEQUENCE: 176
ccggcgttca acctgaatcc 20

<210> SEQ ID NO 177
<211> LENGTH: 20
<212> TYPE: DNA
<213> ORGANISM: Artificial sequence
<220> FEATURE:
<223> OTHER INFORMATION: primer

<400> SEQUENCE: 177
agggcagata gcaggcataa 20

<210> SEQ ID NO 178
<211> LENGTH: 23
<212> TYPE: DNA
<213> ORGANISM: Artificial sequence
<220> FEATURE:
<223> OTHER INFORMATION: primer

<400> SEQUENCE: 178
tctgattgtt ttcctgagtt ttc 23

<210> SEQ ID NO 179
<211> LENGTH: 20
<212> TYPE: DNA
<213> ORGANISM: Artificial sequence
<220> FEATURE:
<223> OTHER INFORMATION: primer

<400> SEQUENCE: 179
agggcagata gcaggcataa 20

<210> SEQ ID NO 180
<211> LENGTH: 23
<212> TYPE: DNA
<213> ORGANISM: Artificial sequence
<220> FEATURE:
<223> OTHER INFORMATION: primer

<400> SEQUENCE: 180
tctgattgtt ttcctgagtt ttc 23

<210> SEQ ID NO 181
<211> LENGTH: 30
<212> TYPE: DNA
<213> ORGANISM: Artificial sequence
<220> FEATURE:
<223> OTHER INFORMATION: primer

<400> SEQUENCE: 181
ccatgattac gaattcattt tttcaatgtg 30

<210> SEQ ID NO 182
<211> LENGTH: 30
<212> TYPE: DNA
<213> ORGANISM: Artificial sequence
<220> FEATURE:
<223> OTHER INFORMATION: primer

<400> SEQUENCE: 182
atggattcct ccttacggtg ttatatgtcc 30

<210> SEQ ID NO 183
<211> LENGTH: 30
<212> TYPE: DNA
<213> ORGANISM: Artificial sequence
<220> FEATURE:
<223> OTHER INFORMATION: primer

<400> SEQUENCE: 183
taaggaggaa tccatatgcc ggaagcacca 30

<210> SEQ ID NO 184
<211> LENGTH: 35
<212> TYPE: DNA
<213> ORGANISM: Artificial sequence
<220> FEATURE:
<223> OTHER INFORMATION: primer

<400> SEQUENCE: 184
gatccccggg taccgagctc ctcgagttaa ttact 35

<210> SEQ ID NO 185
<211> LENGTH: 612
<212> TYPE: PRT
<213> ORGANISM: Artificial sequence
<220> FEATURE:
<223> OTHER INFORMATION: mutant

<400> SEQUENCE: 185

Met Pro Glu Ala Pro Lys Ile Ala Ala Leu Glu Val Ser Asp Glu Ser
1 5 10 15

Leu Ala Glu Lys Asn Lys Asn Lys Leu Gln Phe Ile Glu Asp Val Thr
20 25 30

Thr Asn Ala Asp Asp Val Gln Arg Arg Val Leu Glu Glu Ile Leu Ser
35 40 45

Arg Asn Ala Asp Val Glu Tyr Leu Lys Arg His Gly Leu Glu Gly Arg
50 55 60

Thr Asp Arg Glu Thr Phe Lys His Ile Met Pro Val Val Thr Tyr Glu
65 70 75 80

Asp Ile Gln Pro Glu Ile Asn Arg Ile Ala Asn Gly Asp Lys Ser Gln
85 90 95

Val Leu Cys Ser Asn Pro Ile Ser Glu Phe Leu Thr Ser Ser Gly Thr
100 105 110

-continued

```
Ser Gly Gly Glu Pro Lys Leu Met Pro Thr Ile Glu Glu Glu Leu Asp
        115                 120                 125

Arg Arg Ser Leu Leu Tyr Ser Leu Leu Met Pro Val Met Asp Gln Phe
    130                 135                 140

Val Pro Gly Leu Asp Lys Gly Lys Gly Met Tyr Phe Leu Phe Ile Lys
145                 150                 155                 160

Pro Glu Ser Lys Thr Pro Gly Gly Leu Pro Ala Arg Pro Ala Leu Thr
                165                 170                 175

Ser Tyr Tyr Lys Ser Ser His Phe Lys Asn Arg Pro Tyr Asp Pro Tyr
            180                 185                 190

Thr Asn Tyr Thr Ser Pro Asn Gln Thr Ile Leu Cys Ser Asp Ser Tyr
        195                 200                 205

Gln Ser Met Tyr Ser Gln Met Leu Cys Gly Leu Cys Gln His Lys Glu
    210                 215                 220

Val Leu Arg Val Gly Ala Ala Phe Ala Ser Gly Phe Ile Arg Ala Ile
225                 230                 235                 240

Lys Phe Leu Glu Lys His Trp Pro Glu Leu Ala Arg Asp Ile Arg Thr
                245                 250                 255

Gly Thr Leu Ser Ser Glu Ile Thr Asp Ser Ser Val Arg Glu Ala Val
            260                 265                 270

Gly Glu Ile Leu Lys Pro Asp Pro Lys Leu Ala Asp Phe Val Glu Ser
        275                 280                 285

Glu Cys Arg Lys Thr Ser Trp Gln Gly Ile Ile Thr Arg Leu Trp Pro
    290                 295                 300

Asn Thr Lys Tyr Val Asp Val Ile Val Thr Gly Thr Met Ser Gln Tyr
305                 310                 315                 320

Ile Pro Thr Leu Asp Tyr Tyr Ser Asn Gly Leu Pro Leu Val Cys Thr
                325                 330                 335

Gly Tyr Ala Ser Ser Glu Cys Val Phe Gly Val Asn Leu Arg Pro Leu
            340                 345                 350

Cys Lys Pro Ser Glu Val Ser Tyr Thr Leu Ile Pro Asn Met Ala Tyr
        355                 360                 365

Phe Glu Phe Leu Pro Val His Arg Asn Ser Gly Val Thr Ser Ser Ile
    370                 375                 380

Ser Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
                405                 410                 415

Tyr Ala Gly Leu Tyr Arg Tyr Arg Val Gly Asp Val Leu Ser Val Ala
            420                 425                 430

Gly Phe Lys Asn Asn Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
                485                 490                 495

Tyr Val Leu Phe Trp Glu Leu Cys Leu Asn Gly Asn Thr Pro Ile Pro
            500                 505                 510

Pro Ser Val Phe Glu Asp Cys Cys Leu Thr Ile Glu Glu Ser Leu Asn
        515                 520                 525

Ser Val Tyr Arg Arg Gly Arg Val Ser Asp Lys Ser Ile Gly Pro Leu
```

-continued

```
    530                 535                 540

Glu Ile Lys Met Val Glu Ser Gly Thr Phe Asp Lys Leu Met Asp Tyr
545                 550                 555                 560

Ala Ile Ser Leu Gly Ala Ser Ile Asn Gln Tyr Lys Thr Pro Arg Cys
                565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Ser Pro Gly His Lys Gln
        595                 600                 605

Trp Gly Ser Asn
    610
```

<210> SEQ ID NO 186
<211> LENGTH: 1839
<212> TYPE: DNA
<213> ORGANISM: Artificial sequence
<220> FEATURE:
<223> OTHER INFORMATION: mutant

<400> SEQUENCE: 186

```
atgccggaag caccaaaaat cgcagcctta gaagtcagtg atgagagcct ggctgagaaa     60

aacaaaaaca agctgcaatt tatcgaagat gttaccacca acgctgacga tgtgcaacgt    120

cgcgttctgg aagaaattct gagtcgtaat gcggacgtag aatatctgaa acgccatggt    180

ctggaaggcc gaaccgatcg cgagaccttc aagcacatca tgccggttgt gacgtacgaa    240

gatatccaac ccgaaatcaa ccgtattgcg aatggcgaca aatcgcaggt tctgtgttcg    300

aacccgataa gcgagtttct caccagttcc ggtacctcag gcggagaacc gaaacttatg    360

ccgacgatcg aggaagaact ggatcgtcgg agtctgctgt actcactcct tatgcccgtc    420

atggatcagt ttgttccggg gttagataaa gggaaaggga tgtacttcct cttcatcaag    480

ccggaatcga aaacccctgg tggtctgcct gcacgtcccg cgctgacctc gtattacaag    540

tcctctcact tcaagaatcg accttacgat ccgtatacca actataccag tccgaatcag    600

acgatcttgt gttccgactc ctaccaatcg atgtacagcc agatgctttg cggtctgtgt    660

cagcacaaag aagtgctgcg tgttggcgcg gcgtttgcca gcgggtttat tcgcgcaatc    720

aaatttctgg agaaacactg gccggaattg gcgcgcgaca ttcgcacagg cactctgagc    780

agcgaaatta cggattccag cgttcgcgaa gcagtgggcg agattctgaa acccgatcct    840

aaactggcgg atttcgtcga aagtgaatgt cgcaaaacat cttggcaggg aattattacg    900

cggctatggc caaataccaa atatgttgac gtgattgtca ctggcaccat gagccagtac    960

attccgacac ttgactatta ctcgaacggc ttaccgttag tctgcacggg ctatgcgagc   1020

agtgaatgcg tgtttggagt gaatctcagg ccactatgca aaccatctga agtatcttac   1080

acccttatcc cgaacatggc ctatttcgag ttccttccgg tccatcgtaa ctcaggcgta   1140

actagcagca ttagcttgcc taaagcactg accgaaaaag aacaacagga gttagtagat   1200

ctggtagacg tgaagctggg ccaggaatat gagttagtcg tcacaacgta tgccggtctg   1260

tatcggtatc gcgtgggtga tgtgctgagt gtagccggat tcaaaaataa tgctccgcag   1320

tttagcttta tctgccgtaa aaacgtggtt ctctccattg actctgacaa gacggatgaa   1380

gtggaattgc aaaatgctgt gaaaaacgcc gtaacgcatc tggttccgtt tgatgcctca   1440

ctgtcagaat atacctcgta tgcggatact tcttctattc caggtcatta cgtgctgttc   1500

tgggaattgt gtctgaatgg caacactccg atacctccgt ctgtgtttga ggattgctgc   1560
```

-continued

```
ttgaccattg aagagagctt aaatagcgtg tatcgccgtg gccgtgtgtc cgacaaaagc   1620

attggtccac tggagatcaa gatggtggaa tcgggtactt ttgataagtt gatggattat   1680

gcgatttctt taggcgcgtc catcaaccag tacaaaacac caagatgcgt caaattcgcg   1740

ccgattatcg agctcctgaa ctcacgtgtg gttgacagct atttttcccc caaatgtccg   1800

aaatggtcac cggggcataa acagtggggt agtaattaa                          1839


<210> SEQ ID NO 187
<211> LENGTH: 83
<212> TYPE: PRT
<213> ORGANISM: Umbellularia californica

<400> SEQUENCE: 187

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn
```